(12) United States Patent
Davies et al.

(10) Patent No.: US 7,385,064 B1
(45) Date of Patent: Jun. 10, 2008

(54) CATALYSTS FOR USE IN ENANTIOSELECTIVE SYNTHESIS

(75) Inventors: Huw M. L. Davies, East Amherst, NY (US); Ravisekhara P. Reddy, Amherst, NY (US)

(73) Assignee: The Research Foundation of State University of New York, Amherst NY ( * ) Notice: Subject to any disclaimer, the term of this patent is extended or adjusted under 35 U.S.C. 154(b) by 0 days.

(21) Appl. No.: 11/606,782

(22) Filed: Nov. 30, 2006

Related U.S. Application Data

(60) Provisional application No. 60/741,025, filed on Nov. 30, 2005.

(51) Int. Cl.
C07F 15/00 (2006.01)
C07F 7/02 (2006.01)
C07F 9/02 (2006.01)
B01J 31/00 (2006.01)

(52) U.S. Cl. ............... 548/404; 556/136; 564/336; 564/340; 568/14; 568/15; 568/17; 502/166

(58) Field of Classification Search ............... 548/404; 556/136; 564/336, 340; 568/14, 15, 17; 502/166
See application file for complete search history.

(56) References Cited

U.S. PATENT DOCUMENTS

| | | | |
|---|---|---|---|
| 2,507,631 A | 5/1950 | Hartmann et al. | 260/294 |
| 2,957,880 A | 10/1960 | Rometsch et al. | 260/294 |
| 4,133,881 A | 1/1979 | Cale, Jr. et al. | 424/244 |
| 4,238,488 A | 12/1980 | Howe et al. | 424/248.55 |
| 4,866,048 A | 9/1989 | Calverley et al. | 514/167 |
| 5,036,053 A | 7/1991 | Himmelsbach et al. | 514/19 |
| 5,175,311 A | 12/1992 | Doyle | 549/302 |
| 5,296,595 A | 3/1994 | Doyle | 540/200 |
| 5,401,732 A | 3/1995 | Calverley et al. | 514/167 |
| 5,591,854 A | 1/1997 | Davies | 546/14 |
| 5,639,913 A | 6/1997 | Lidor et al. | 564/304 |
| 5,665,890 A | 9/1997 | Jacobsen et al. | 549/230 |

(Continued)

FOREIGN PATENT DOCUMENTS

GB 2 260 903 A 5/1993

(Continued)

OTHER PUBLICATIONS

Galvez et al., "Cobalt-Mediated Alklation of (4R) and (4S)-3-Acetoacetyl-4-benzyloxazolidin-2-ones. Preparation of Enantiopure Diphenylmethyl-, 9-Fluorenyl-and (1-Adamantyl)glycines," Tetrahedron Lett., 37(34):6197-6200 (1996).

(Continued)

*Primary Examiner*—Porfirio Nazario-Gonzalez
(74) *Attorney, Agent, or Firm*—Peter Rogalskyj, Esq.

(57) ABSTRACT

Disclosed are compounds having the following formula:

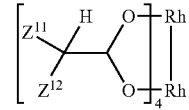

in which $Z^{11}$ is selected from a substituted or unsubstituted saturated adamantyl or other polycyclic group and a substituted or unsubstituted branched acyclic group containing at least 5 carbon atoms at least one of which is a tertiary carbon; and in which $Z^{12}$ is a cyclic imide. Methods of using these compounds as chiral catalysts for carbenoid reactions and for enantioselective C—H aminations are also described.

44 Claims, 1 Drawing Sheet

U.S. PATENT DOCUMENTS

| | | | |
|---|---|---|---|
| 5,760,055 A | 6/1998 | Davies | 514/304 |
| 6,410,746 B1 | 6/2002 | Davies | 548/403 |
| 6,762,304 B2 | 7/2004 | Davies | 546/268.1 |
| 6,962,891 B2 | 11/2005 | Davies et al. | 502/159 |
| 7,030,051 B2 | 4/2006 | Davies | 502/150 |
| 7,109,343 B2 | 9/2006 | Davies | 546/268.1 |

FOREIGN PATENT DOCUMENTS

| | | |
|---|---|---|
| WO | WO 00/64583 | 11/2000 |

OTHER PUBLICATIONS

Scherer et al., "7-Phosphono-z-Aryl-Norcaradiene," Chem. Ber., 105:3357-3381 (1972).

Carlsen et al., "A Greatly Improved Procedure for Ruthenium Tetroxide Catalyzed Oxidations of Organic Compounds," Org. Chem., 46(19):3936-3938 (1981).

Breslow et al., "Tosylamidation of Cyclohexane by a Cytochrome P-450 Model," J. Chem. Soc., Chem. Commun., (10):1400-1401 (1982).

Breslow et al., "Intramolecular Nitrene Carbon-Hydrogen Insertions Mediated by Transition-metal Complexes as Nitrogen Analogs of Cytochrome P-450 Reactions," J. Am. Chem. Soc., 105(22):6728-6729 (1983).

Callot et al., "Rhodium(II)2,4,6-Triarylbenzoates: Improved Catalysts for Syn Cyclopropanation of z-Olefins," Tetrahedron, 41(20):4495-4501 (1985).

Evans et al., "The Asymmetric Synthesis of -Lactam Antibiotics—I. Application of Chiral Oxazolidones in the Staudinger Reaction," Tetrahedron Lett., 26(32):3783-3786 (1985).

Tomioka et al., "Effect of the Phosphonate Group on the Reactivity of Carbenes. Neighbouring Phosphonate Group Participation,", J. Chem. Soc. Chem. Commun., (6):362-364 (1989).

Evans et al., "Cooper-Catalyzed Aziridination of Olefins by (N-(p-Toluenesulfonyl)imino)-phenyliodinane," J. Org. Chem., 56(24):6744-6746 (1991).

Li et al., "Asymmetric Alkene Aziridination with Readily Available Chiral Dilmine-Based Catalysts," J. Am. Chem. Soc., 115(12):5326-5327 (1993).

Barani et al., "Cs2CO3 or CaO as promoters of Ethyl N-{[(4-Methylphenyl)sulphonyl]oxy}carbamate in Amination Reactions," Tetrahedron, 50(38):11235-11238 (1994).

Davies et al., "Enantioselective Synthesis of Cyclopropylphosphonates Containing Quaternary Stereocenters Using a D2-Symmetric Chiral Catalyst Rh2(S-biTISP)2," Org. Lett., 6 (13):2117-2120 (1994).

Evans et al., "Development of the Copper-Catalyzed Olefin Aziridination Reaction," J. Am. Chem. Soc., 116(7):2742-2753 (1994).

Fukuyama et al., "2- and 4-Nitrobenzenesulfonamides: Exceptionally Versatile Means for Preparation of Secondary Amines and Protection of Amines," Tetrahedron Lett., 36(36):6373-6374 (1995).

Li et al., "Mechanism of the (Diimine)copper-Catalyzed Asymmetric Aziridination of Alkenes. Nitrene Transfer via Ligand-Accelerated Catalysis," J. Am. Chem. Soc., 117(21):5889-5890 (1995).

Lim et al., "Enantioselective Synthesis of a 1,2-Disubstituted Mitosene by a Copper-Catalyzed Intramolecular Carbon-Hydrogen Insertion Reaction of a Diazo Ester," J. Org. Chem., 60(8):2326-2327 (1995).

Ye et al., "Chemoselectivity and Stereoselectivity of Cyclisation of alpha-Diazocarbonyls Leading to Oxygen and Sulfur Heterocycles Catalysed by Chiral Rhodium and Copper Catalysts," J. Chem. Soc., Perkin Trans. 1, (11):1373-1379 (1995).

Galvez et al., "Cobalt-Mediated Alkylation of (4R) and (4S)-3-Acetoacetyl-4-benzyloxazolidin-2-ones. Preparation of Enantiopure Diphenylmethyl-, 9-Fluorenyl- and (1-Adamantyl)glycines," Tetrahedron Lett., 37(34):6197-6200 (1996).

Davies et al., "Asymmetric Cyclopropanations by Rhodium (II) N-(Arylsulfonyl)prolinate Catalyzed Decomposition of Vinyldiazomethanes in the Presence of Alkenes. Enantioselective Synthesis of the Four Stereoisomers of 2-Phenylcyclopropan-1-amino Acid," J. Am. Chem. Soc., 118(29):6897-6907 (1996).

Davies et al., "Asymmetric Intermolecular Carbenoid C-H Insertions Catalyzed by Rhodium(II) (S)-N-(p-Dodecylphenyl)sulfonylprolinate," J. Am. Chem. Soc., 119(38):9075-9076 (1997).

Ghosh et al., "A Convenient Enzymatic Route to Optically Active 1-Aminoindan-2-ol: Versatile Ligands for HIV-1 Protease Inhibitors and Asymmetric Syntheses," Synthesis, (5):541-544 (1997).

Nageli et al., "Rhodium(II)-Catalyzed CH Insertions with {[(4-Nitrophenyl)sulfon-yl]imino}phenyl- 3-iodane," Helv. Chim. Acta, 80(4):1087-1105 (1997).

Sodergren et al., "Readily Available Nitrene Precursors Increase the Scope of Evans' Asymmetric Aziridination of Olefins," Tetrahedron: Asymmetry, 8(21):3563-3565 (1997).

Au et al., "Ruthenium-Mediated Amidation of Saturated C-H bonds and Crystal Structure of a Bis(tosyl)amidoruthenium(III) Complex of 1,4,7-Trimethyl-1,4,7-triazacyclononane," Chem. Commun., (24):2677-2678 (1998).

Takacs et al., "Preparation of Chiral Oxazolidin-2-ones and Vicinal Amino Alcohols," J. Org. Chem., 63(68):2742-2748 (1998).

Axten et al., "Enantioselective Synthesis of D-threo-Methylphenidate," J. Am. Chem. Soc., 121(27):6511-6512 (1999).

Davies, "Dirhodium Tetra(N-arylsulfonylprolinates) as Chiral Catalysts For Asymmetric Transformations of Vinyl- and Aryldiazoacetates," Eur. J. Org. Chem., pp. 2459-2469 (1999).

Davies et al., "Catalytic Asymmetric Synthesis of Diarylacetates and 4,4-Diarylbutanoates. A Formal Asymmetric Synthesis of (+)-Sertraline," Org. Lett., 1(2):233-236 (1999).

Davies et al., "Catalytic Asymmetric Synthesis of Syn-Aldol Products from Intermolecular C-H Insertions Between Allyl Silyl Ethers and Methyl Aryldiazoacetates," Organic Letters, 1(3):383-385 (1999).

Davies et al., "Highly Regio-, Diastereo-, and Enantioselective C-H insertions of Methyl Aryldiazoacetates into Cyclic N-Boc-Protected Amines. Asymmetric Synthesis of Novel C2-Symmetric Amines and threo-Methylphenidate," J. Am. Chem. Soc., 121(27):6509-6510 (1999).

Dossetter et al., "Highly Enantio- and Diastereoselective Hetero-Diels-Alder Reactions Catalyzed by New Chiral Tridentate Chromium(III) Catalysts," Angew. Chem., Int. Ed., 38():2398- (1999).

Hou et al., "JM-PHOS Ligands: Second-Generation Phosphine Oxazolines for Asymmetric Catalysis," Org. Lett., 1(11):1745-1747 (1999).

Kitagaki et al., "Enantiocontrol in Tandem Carbonyl Ylide Formation and Intermolecular 1,3-Dipolar Cycloaddition of alpha-Diazo Ketones Mediated by Chiral Dirhodium(II) Carboxylate Catalyst," J. Am. Chem. Soc., 121(6):1417-1418 (1999).

Sibi et al., "Investigations of a Nucleophilic Alaninol Synthon Derived from Serine," J. Am. Chem. Soc., 121(33):7509-7516 (1999).

Zhou et al., "Asymmetric Amidation of Saturated C—H Bonds Catalysed by Chiral Ruthenium and Manganese Porphyrins," Chem. Commun., (23):2377-2378 (1999).

Au et al., "Amidation of Unfunctionalized Hydrocarbons Catalyzed by Ruthenium Cyclic Amine or Bipyridine Complexes," J. Org. Chem., 65(23):7858-7864 (2000).

Clariana et al., "Preparation of (R)-(1-Adamantyl)glycine and (R)-2-(1-Adamantyl)-2-aminoethanol: A Combination of Cobalt-Mediated -Ketoester Alkylation and Enzyme-based Aminoalcohol Resolution," Tetrahedron: Asymmetry, 11(22):4549-4557 (2000).

Davies et al., "Asymmmetric Catalytic C—H Activation Applied to the Synthesis of Syn-Aldol Products," Org. Lett., 2(26):4153-4156 (2000).

Davies et al., "Catalytic Asymmetric C—H Activation of Alkanes and Tetrahydrofuran," J. Am. Chem. Soc., 122(13):3063-3070 (2000).

Davies et al., "Effect of carbenoid Structure on the Reactions of Rhodium-stabilized Carbenoids with Cycloheptatriene," Tetrahedron Lett., 41(13):2035-2038 (2000).

Glos et al., "Aza-bis(oxazolines): New Chiral Ligands for Asymmetric Catalysis," Org. Lett., 2(14):2045-2048 (2000).

Hasegawa et al., "Facile Asymmetric Synthesis of -Amino Acids Employing Chiral Ligand-Mediated Asymmetric Addition Reactions of Phenyllithium with Imines," Tetrahedron 56(52):10153-10158 (2000).

Helmchen et al., "Phosphinooxazolines-A New Class of Versatile, Modular P,N-Ligands for Asymmetric Catalysis," Acc. Chem. Res., 33(6):336-345 (2000).

Johnson et al., "Chiral Bis(oxazoline) Copper(II) Complexes: Versatile Catalysts for Enantioselective Cycloaddition, Aldol, Michael, and Carbonyl Ene Reactions," Acc. Chem. Res., 33(6):325-335 (2000).

Muller et al., "Intermolecular Cyclopropanation versus CH Insertion in RhII-Catalyzed Carbenoid Reactions," Tetrahedron, 56(12):1725-1731 (2000).

Yu et al., "Amidation of Saturated C—H Bonds Catalyzed by Electron-Deficient Ruthenium and Manganese Porphyrins. A Highly Catalytic Nitrogen Atom Transfer Process," Org. Lett., 2(15):2233-2236 (2000).

Davies et al., "Asymmetric Intramolecular C—H Insertions of Aryldiazoacetates," Org. Lett., 3(10), 1475-1477 (2001).

Davies et al., "Catalytic Asymmetric C—H Activation of Silyl Enol Ethers as an Equivalent of an Asymmetric Michael Reaction," J. Am. Chem. Soc., 123(9):2070-2071 (2001).

Davies et al., "Recent Progress in Asymmetric Intermolecular C—H Activation by Rhodium Carbenoid Intermediates," J. Organomet. Chem., 617:47-55 (2001).

Espino et al., "A Rh-Catalyzed C—H Insertion Reaction for the Oxidative Conversion of Carbamates to Oxazolidinones," Angew. Chem., Int. Ed., 40(3):598-600 (2001).

Espino et al., "Synthesis of 1,3-Difunctionalized Amine Derivatives through Selective C—H Bond Oxidation," J. Am. Chem. Soc., 123(28):6935-6936 (2001).

Kohmura et al., "Mn(salen)-Catalyzed Enantioselective C—H Amination," Tetrahedron Lett., 42(19):3339-3342 (2001).

Schinnerl et al., "New Applications of Bis(oxazoline) Ligands in Catalysis: Asymmetric 1,2- and 1,4-Addition of ZnR2 to Carbonyl Compounds," Org. Lett., 3(26):4259-4262 (2001).

Takahashi et al., "Catalytic Asymmetric Synthesis of 1,1'-Spirobi[indan-3,3'-dione] via a Double Intramolecular C—H Insertion Process," Chem. Commun., (17):1604-1605 (2001).

Tsutsui et al., "Enantioselective Tandem Formation and [2,3]-Sigmatropic Rearrangement of Cyclic Propargylic Oxonium Ylides Catalyzed by Direhodium(II) Tetrakis[N-phthaloyl-(S)-tert-leucinate", Israel Journal of Chemistry, 41:283-295 (2001).

Chen et al., "A General, Highly Enantioselective Method for the Synthesis of D and L Aplha-Amino Acids and Allylic Amines," J. Am. Chem. Soc., 124(41):12225-12231 (2002).

Clariana et al., "2,2 '-Isopropylidenebis[(4R)-(1-adamantyl)-2-oxazoline] (Adam-Box). A new enantiopure C2-symmetrical ligand: enantioselective cyclopropanations, Diels—Alder reactions, and allylic oxidations," Tetrahedron: Asymmetry, 13(14):1551-1554 (2002).

Gillespie et al., "Enantioselective Aziridination Using Copper Complexes of Biaryl Schiff Bases," J. Org. Chem., 67(10):3450-3458 (2002).

Liang et al., "Amidation of Silyl Enol Ethers and Cholesteryl Acetates with Chiral Ruthenium(II) Schiff-Base Catalysts: Catalytic and Enantioselective Studies," Chem. Commun., (2):124-125(2002).

Liang et al., "Highly Diastereo- and Enantioselective Intra-molecular Amidation of Saturated C—H Bonds Catalyzed by Ruthenium Porphyrins," Agnew. Chem., Int. Ed., 41(18):3465-3468 (2002).

Liang et al., "Metalloporphyrin-Mediated Asymmetric Nitrogen-Atom Transfer to Hydrocarbons: Aziridination of Alkenes and Amidation of Saturated C—H Bonds Catalyzed by Chiral Ruthenium and Manganese Porphyrins," Chem.-Eur. J., 8(7):1563-1572 (2002).

Liang et al., "Rhodium(II,II) Dimer as an Efficient Catalyst for Aziridination of Sulfonamides and Amidation of Steroids," Org. Lett., 4(25):4507-4510 (2002).

Muller et al., "The Enantioselectivity and the Stereochemical Course of Copper-Catalyzed Intramolecular CH Insertions of Phenyliodonium Ylides," Helv. Chim. Acta, 85(2):483-494 (2002).

Ruck et al., "Asymmetric Catalysis of Hetero-Ene Reactions with Tridentate Schiff Base Chromium(III) Complexes," J. Am. Chem. Soc., 124(12):, 2882-2883 (2002).

Saito et al., "Enantio- and diastereoselective Synthesis of cis-2-Aryl-3-methoxycarbonyl-2,3-dihydrobenzofurans via the Rh(II)-Catalyzed C—H Insertion Process," Org. Lett., 4(22):3887-3890 (2002).

Sterling et al., "Novel Dual Inhibitors of AChE and MAO Derived from Hydroxy Aminoindan and Phenethylamine as Potential Treatment for Alzheimer's Disease," J. Med. Chem., 45(24):5260-5279 (2002).

Yamawaki et al., "Dirhodium(II) Tetrakis[N-tetrachlorophthaloyl-(S)-tert-leucinate]: A New Chiral Rh(II) Catalyst for Enantioselective Amidation of C—H Bonds," Tetrahedron Lett., 43(52):9561-9564 (2002).

Davies et al., "Catalytic Enantioselective C—H Activation by Means of Metal-Carbenoid-Induced C—H Insertion," Chem. Rev., 103(8):2861-2904 (2003).

Hinmann et al., "A Stereoselective Synthesis of (-)-Tetrodotoxin," J. Am. Chem. Soc., 125(38):11510-11511 (2003).

Kurosawa et al., "An Efficient Synthesis of Optically Active trans-2-Aryl-2,3-dihydrobenzofuran-3-carboxylic Acid Esters via C—H Insertion Reaction," Synlett, (7):1028-1030 (2003).

Kurosawa et al., "Stereocontrolled Total Synthesis of (-)-Ephedradine A (Orantine)," J. Am. Chem. Soc., 125(27):8112-8113 (2003).

Leung et al., "Nitrido Ruthenium Porphyrins: Synthesis, Characterization, and Amination Reactions with Hydrocarbon or Silyl Enol Ethers," Angew. Chem., Int. Ed., 42(3):340-343 (2003).

Muller et al., "Enantioselective Catalytic Aziridinations and Asymmetric Nitrene Insertions into CH Bonds," Chem. Rev., 103(8):2905-2920 (2003).

Omura et al., "Enantioselective Aziridination and Amination Using p-Toluenesulfonyl Azide in the Presence of Ru(salen)(CO) Complex," Chem. Lett., 32(4):354 (2003).

Perry et al., "Optically Active Iridium Imidazol-2-ylidene-oxazoline Complexes: Preparation and Use in Asymmetric Hydrogenation of Arylalkenes,") J. Am. Chem. Soc., 125(1):113-123 (2003).

Tsang et al., "An Enantiomerically Pure Adamantylimido Molybdenum Alkylidene Complex. An Effective New Catalyst for Enantioselective Olefin Metathesis," J. Am. Chem. Soc., 125(9), 2591-2596 (2003).

Tsutsui et al., "Dirhodium(II) tetrakis[N-tetrafluorophthaloyl-(S)-tert-leucinate]: An Exceptionally Effective Rh(II) Catalyst for Enantiotopically Selective Aromatic C—H Insertions of Diazo Ketoesters," Tetrahedron: Asymmetry, 14(7):817-821 (2003).

Wehn et al., "Stereochemical Models for Rh-Catalyzed Amination Reactions of Chiral Sulfamates,", Org. Lett., 5(25):4823-4826 (2003).

Yoon et al., "Privileged Chiral Catalysts," Science, 299(5613):1691-1693 (2003).

Espino et al., "Expanding the Scope of C—H Amination through Catalyst Design," J. Am. Chem. Soc., 126(47):15378-15379 (2004).

Fiori et al., "Rh-Catalyzed Amination of Ethereal C—H Bonds: A Versatile Strategy for the Synthesis of Complex Amines" Angew. Chem., Int. Ed., 43(33):4349-4352 (2004).

Fruit et al., "Intramolecular Asymmetric Amidations of Sulfonamides and Sulfamates Catalyzed by Chiral Dirhodium(II) Complexes," Helv. Chim. Acta, 87(7):1607-1615 (2004).

Kan et al., "Ns Strategies: A Highly Versatile Synthetic Method for Amines," Chem. Commun., (4):353-359 (2004).

Augeri et al., "Discovery and Preclinical Profile of Saxagliptin (BMS-477118): A Highly Potent, Long-Acting, Orally Active Dipeptidyl Peptidase IV Inhibitor for the Treatment of Type 2 Diabetes," J. Med. Chem., 48(15):5025-5037 (2005).

Davies et al., "Asymmetric Intermolecular C—H Functionalization of Benzyl Silyl Ethers Mediated by Chiral Auxiliary-Based Aryldiazoacetates and Chiral Dirhodium Catalysts," J. Org. Chem., 70(26), 10737-10742 (2005).

Davies et al., "Recent Advances in Catalytic Intramolecular C—H Aminations," Angew. Chem., Int. Ed., 44(23):3518-3520 (2005).

Espino et al., pp. 379-416 in Evans, ed., Modern Rhodium Catalyzed Organic Reactions; Wiley: New York (2005).

Lebel et al., "N-Tosyloxycarbamates as a Source of Metal Nitrenes: Rhodium-Catalyzed C—H Insertion and Aziridination Reactions," J. Am. Chem. Soc., 127(41):14198-14199 (2005).

Minami et al., "Highly Enantio- and Diastereoselective Construction of 1,2-Disubstituted Cyclopentane Compounds by Dirhodium(II) Tetrakis[N-phthaloyl-(S)-tert-leucinate]-Catalyzed CH Insertion Reactions of-Diazo Esters," Adv. Synth. Catal., 347(11-13):1483-1487 (2005).

Davies et al., "Direct Synthesis of Methyl 2-Diazo-4-Aryl-3-Butenoates and Their Application to the Enantioselective Synthesis of 4-Aryl-4-(1-Naphthyl)-2-Butenoates," Tetrahedron: Asymmetry, 17(4):665-673 (2006).

Davies et al., "Dirhodium Tetracarboxylate Derived from Adamantylglycine as a Chiral Catalysts for Enantioselective C—H Aminations," Organic Letters, 8(22):5013-5016 (2006).

Fleming et al., "A Synthesis of (+)-Saxitoxin," J. Am. Chem. Soc., 128(12):3926-3927 (2006).

Kim et al., "Expanding the Substrate Scope for C—H Amination Reactions: Oxidative Cyclization of Urea and Guanidine Derivatives," Org. Lett., 8(6):1073-1076 (2006).

Reddy et al., "Dirhodium Tetracarboxylate Derived from Adamantylglycine as a Chiral Catalyst for Carbenoid Reactions," Organic Letters, 8(16):3437-3440 (2006).

CATALYSTS FOR USE IN ENANTIOSELECTIVE SYNTHESIS

The present application claims the benefit of U.S. Provisional Patent Application Ser. No. 60/741,025, filed Nov. 30, 2005, which provisional patent application is hereby incorporated by reference.

The present invention was made with the support of the National Science Foundation Contract CHE0350536. The Federal Government may have certain rights in this invention.

FIELD OF THE INVENTION

The present invention relates generally to dirhodium catalysts and, more particularly, to dirhodium chiral catalysts for use in enantioselective synthesis.

BACKGROUND OF THE INVENTION

Donor/acceptor-substituted rhodium carbenoids such as 1 have been shown to be versatile intermediates in organic synthesis. These carbenoids are capable of extremely selective reactions, and when catalyzed by rhodium prolinates such as $Rh_2(S\text{-}DOSP)_4$ (2) the reactions are routinely highly enantioselective.

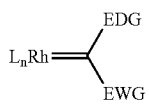

1

EDG = Aryl, vinyl, alkynyl
EWG = $CO_2Me$

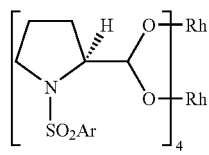

$Rh_2(S\text{-}DOSP)_4$

Ar = $p\text{-}C_{12}H_{25}C_6H_4$

One of the earliest explored reactions was the cyclopropanation chemistry of the donor/acceptor-substituted carbenoids. As illustrated in the reaction of the vinyldiazoacetate 3 with styrene, the reactions are highly diastereoselective, which is in marked contrast to the typical cyclopropanation chemistry of ethyl diazoacetate. The $Rh_2(S\text{-}DOSP)_4$ catalyzed reaction of 3 with styrene at −78° C. generates the cyclopropane 4 in 98% de and 98% ee.

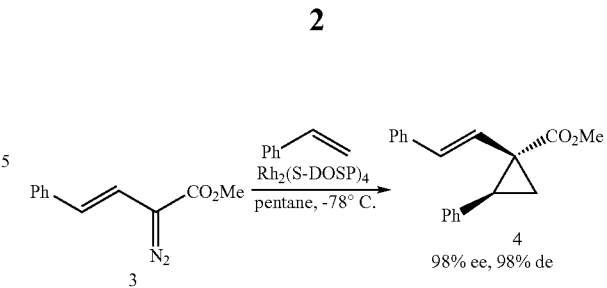

The reaction conditions have been recently optimized such that the cyclopropanations can be conducted with immobilized catalysts or with catalyst loadings as low as 0.001%. The optimum catalyst for the high turnover work was the bridged catalyst $Rh_2(S\text{-}biTISP)_4$.

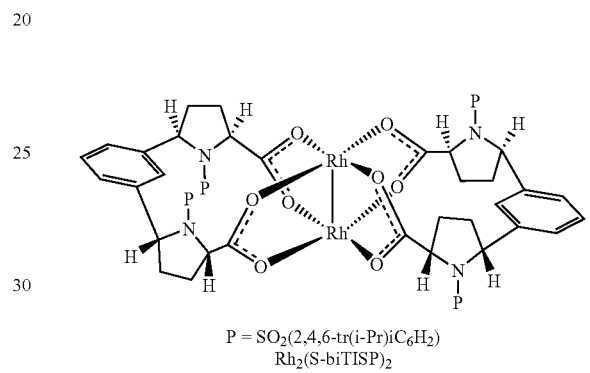

$P = SO_2(2,4,6\text{-}tr(i\text{-}Pr)iC_6H_2)$
$Rh_2(S\text{-}biTISP)_2$

A major breakthrough in the chemistry of the donor/acceptor-substituted carbenoids was the discovery that these carbenoids are very effective for selective intermolecular C—H insertions. This is a very powerful synthetic strategy for "C—H activation", and it is arguably the most practical and versatile method to date for catalytic asymmetric C—H functionalization. Prior to our work, the intramolecular C—H insertions were well established but the intermolecular version was not considered synthetically useful because the conventional carbenoids were too reactive and very prone to dimerization. These problems have now been solved by using the donor/acceptor-substituted carbenoids because they are more stabilized than the conventional carbenoids.

(3)

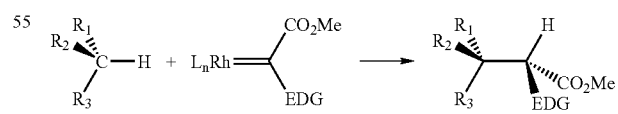

The C—H functionalization strategy offers an alternative to many of the classic reactions of organic synthesis. It can be considered as a surrogate to the aldol reaction, the Claisen rearrangement, the Mannich reaction, and the Michael addition, and, in all cases, excellent control of both relative and absolute stereochemistry is possible. Furthermore, the chemistry has been used in the direct synthesis of pharmaceutical targets such as (+)-cetiedil (5), (+)-indatraline (6), threo-methylphenidate (Ritalin) (7), and the lignan α-conidendrin (8).

5

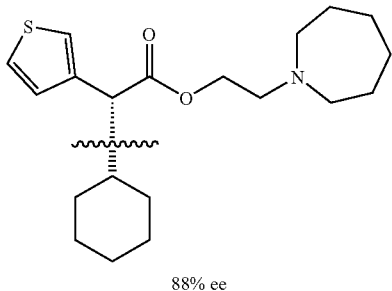

88% ee

6

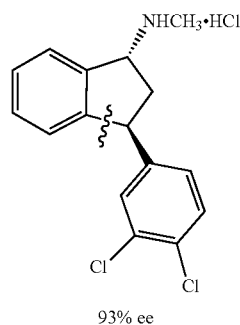

93% ee

7

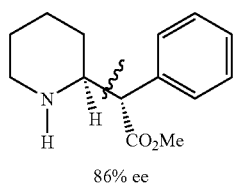

86% ee

8

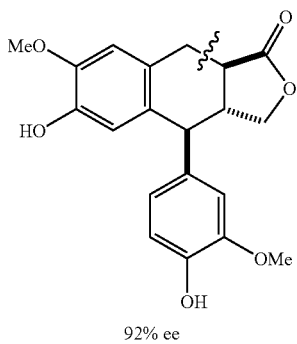

92% ee

The C—H activation chemistry is capable of spectacular chemoselectivity. C—H functionalization is favored at sites that stabilize developing positive charge on the carbon undergoing insertion, but this effect is counterbalanced by the steric influence of the carbenoid.

In all of the studies described above, the electron withdrawing group was a methyl ester. Even increasing the size of the methyl ester to a tert-butyl ester caused a dramatic drop in the enantioselectivity (from 90% ee to 50% ee, 74% ee to 9% ee). Therefore, it would be highly desirable to develop a new type of chiral catalyst that would be applicable to other types of electron withdrawing groups. The present invention is directed, in part, to addressing this need.

SUMMARY OF THE INVENTION

The present invention relates to a compound having the formula:

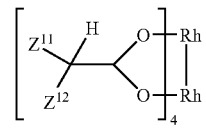

in which $Z^{11}$ is selected from a substituted or unsubstituted saturated polycyclic group and a substituted or unsubstituted branched acyclic group containing at least 5 carbon atoms at least one of which is a tertiary carbon; and in which $Z^{12}$ is a cyclic imide.

DETAILED DESCRIPTION OF THE INVENTION

Figure 1:
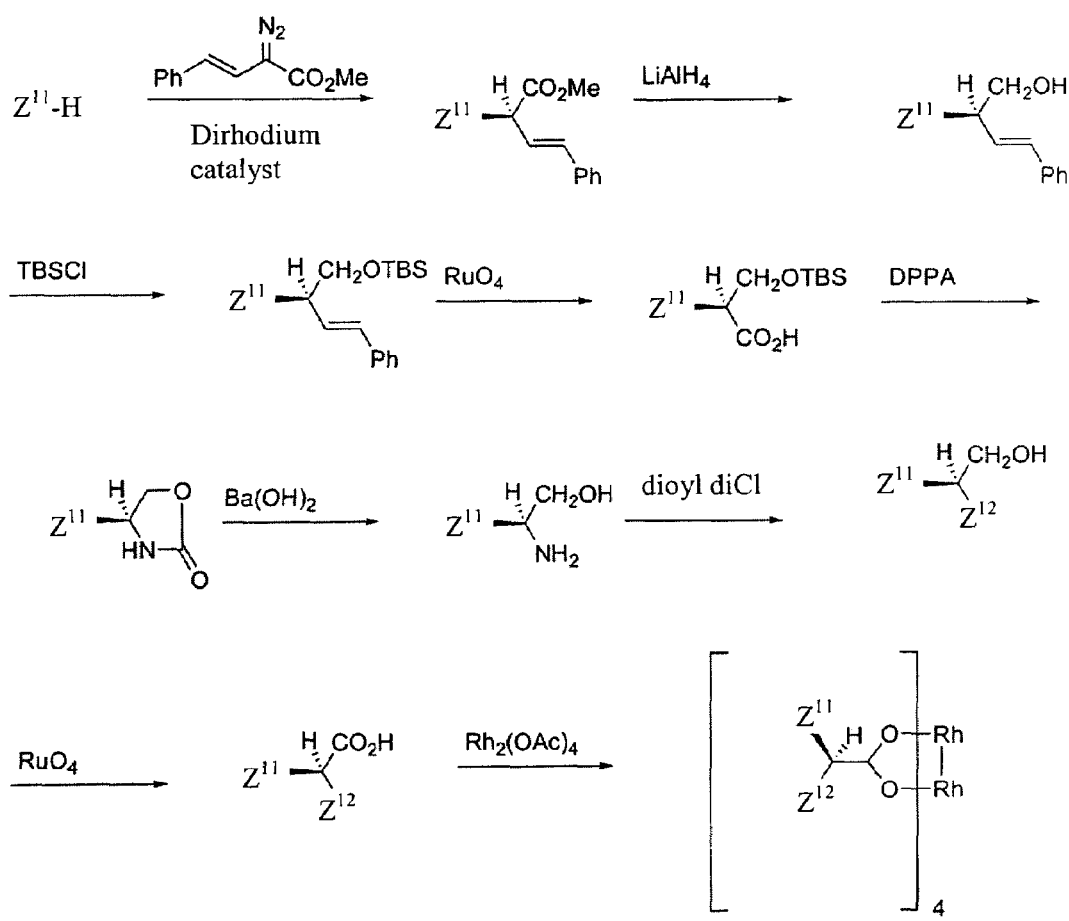
FIG. 1 is a reaction scheme for the preparation of compounds of the present invention.

As used herein, "alkyl" is meant to include linear alkyls, branched alkyls, and cycloalkyls, each of which can be substituted or unsubstituted. "Alkyl" is also meant to include lower linear alkyls (e.g., C1-C6 linear alkyls), such as methyl, ethyl, n-propyl, n-butyl, n-pentyl, and n-hexyl; lower branched alkyls (e.g., C3-C8 branched alkyls), such as isopropyl, t-butyl, 1-methylpropyl, 2-methylpropyl, 1-methylbutyl, 2-methylbutyl, 3-methylbutyl, 1,2-dimethylpropyl, 1,1-dimethylpropyl, 2,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 2-methyl-2-ethylpropyl, 2-methyl-1-ethylpropyl, and the like; and lower cycloalkyls (e.g., C3-C8 cycloalkyls), such as cyclopropyl, cyclobutyl, cyclopentyl, cyclohexyl, and the like. "Alkyl", as use herein, is meant to include unsubstituted alkyls, such as those set forth above, in which no atoms other than carbon and hydrogen are present. "Alkyl", as use herein, is also meant to include substituted alkyls. Suitable substituents include aryl groups (which may themselves be substituted), heterocyclic rings (saturated or unsaturated and optionally substituted), alkoxy groups (which is meant to include aryloxy groups (e.g., phenoxy groups)), amine groups (e.g., disubstituted with aryl or alkyl groups), carboxylic acid derivatives (e.g., carboxylic acid esters, amides, etc.), halogen atoms (e.g., Cl, Br, and I), and the like. Further, alkyl groups bearing one or more alkenyl or alkynyl substituents (e.g., a methyl group itself substituted with a prop-1-en-1-yl group to produce a but-2-en-1-yl substituent) is meant to be included in the meaning of "alkyl".

As used herein, "alkoxy" is meant to include groups having the formula —O—R, where R is an alkyl or aryl group. They include methoxy, ethoxy, propoxy, phenoxy, 4-methylphenoxy, and the like.

As used herein, "aryl" is meant to include aromatic rings, for example, aromatic rings having from 4 to 12 members, such as phenyl rings. These aromatic rings can optionally contain one or more heteroatoms (e.g., one or more of N, O, and S), and, thus, "aryl", as used herein, is meant to include heteroaryl moieties, such as pyridyl rings and furanyl rings. The aromatic rings can be optionally substituted. "Aryl" is also meant to include aromatic rings to which are fused one or more other aryl rings or non-aryl rings. For example, naphthyl groups, indole groups, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), amine groups (e.g., disubstituted with aryl or alkyl groups), carboxylic acid groups, carboxylic acid derivatives (e.g., carboxylic acid esters, amides, etc.), halogen atoms (e.g., Cl, Br, and I), and the like.

As used herein, "ring" refers to a homocyclic or heterocyclic ring which can be saturated or unsaturated, aromatic or non-aromatic. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems. In the case where the ring is saturated (i.e., in the case where each of the atoms making up the ring are joined by single bonds to other members of the ring), the ring may optionally include unsaturated (aromatic or nonaromatic) or saturated substituents.

In one aspect, the present invention relates to compounds having the formula ("Formula I"):

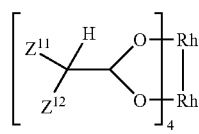

in which $Z^{11}$ is selected from a substituted or unsubstituted saturated polycyclic group or a substituted or unsubstituted branched acyclic group containing at least 5 carbon atoms at least one of which is a tertiary carbon; and in which $Z^{12}$ is a cyclic imide.

In Formula I and in all other formulae set forth in this document which contain one or more chiral centers and which do not specify the stereochemistry of a particular chiral center, such formulae are to be construed as encompassing all possible stereochemistries. Thus, for example, Formula I is meant to include (i) compounds in which the unspecified chiral center is entirely in the R configuration, (ii) compounds in which the unspecified chiral center is entirely in the S configuration, and (iii) racemic and other mixtures of (i) and (ii). Illustratively, compounds of Formula I are meant to include substantially chirally pure catalysts having one of the following formulae ("Formula II-A" and "Formula II-B", respectively):

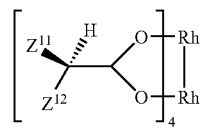

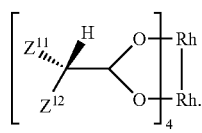

As used herein, "polycyclic group" is meant to include unbridged bicyclics, bridged bicyclics, unbridged tricyclics, bridged tricyclics, adamantyl, norbornyl, etc. As indicated above, these polycyclic groups can be unsubstituted or substituted, for example, with one, two, three, or more substituents selected, illustratively and independently, from alkyl groups (which may themselves be substituted), aryl groups (which may themselves be substituted) heterocyclic rings (saturated or unsaturated and optionally substituted), hydroxy groups, alkoxy groups (which is meant to include aryloxy groups (e.g., phenoxy groups)), carboxylic acid derivatives (e.g., carboxylic acid esters, amides, etc.), halogen atoms (e.g., F, Cl, Br, and I), and the like. Illustratively, suitable polycyclic groups for use as $Z^{11}$ in the compounds of Formulae I, II-A, and II-B include those having the formulae:

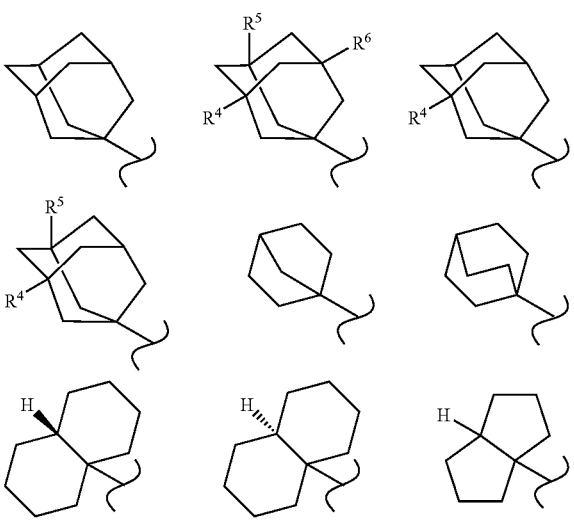

where each R (e.g., $R^4$, $R^4$ and/or $R^6$ can be any of the alkyl substituents recited hereinabove (e.g., selected from halogen, alkyl, aryl, alkoxy, hydroxy, carboxy ester, and carboxy amide). Illustratively, where there are two or more R groups, all the R groups can be the same (e.g., in the case where the formula contains an $R^4$ and an $R^5$, each of $R^4$ and $R^5$ can represent the same particular halogen, the same particular alkyl, the same particular aryl, the same particular alkoxy, hydroxy, the same particular carboxy ester, or the same particular carboxy amide). Alternatively, where there are two or more R groups, some or all of the R groups can be different (e.g., in the case where the formula contains an $R^4$ and an $R^5$, $R^4$ can be an alkyl and $R^5$ can be a different alkyl, or $R^4$ can be an alkyl and $R^5$ can be a halogen, or $R^4$ can be a halogen and $R^5$ can be a different halogen).

As used herein, "branched acyclic groups containing at least 5 carbon atoms at least one of which is a tertiary carbon" are meant to include —$CR^{51}R^{52}R^{53}$, where $R^{51}$, $R^{52}$, and $R^{53}$ are the same or different and at least one of (e.g., exactly one of, exactly two of, or all of) $R^{51}$, $R^{52}$, and $R^{53}$ is an alkyl containing 2 or more carbon atoms (e.g., in the case where at least one of $R^{51}$, $R^{52}$, and $R^{53}$ is a branched alkyl). In certain illustrative embodiments, at least one of (e.g., exactly one of, exactly two of, or all of) $R^{51}$, $R^{52}$, and $R^{53}$ is a branched alkyl, such as in the case where $R^{51}$ is a methyl group and where $R^{52}$ and $R^{53}$ are the same or different C3-C8 branched alkyl groups, as in the case where $R^{51}$ is a methyl group and where $R^{52}$ and $R^{53}$ are the same or different C3-C6 branched alkyl groups, as in the case where $R^{51}$ is a methyl group and where $R^{52}$ and $R^{53}$ are the same or different C3-C4 branched alkyl groups, and/or as in the case where $R^{51}$ is a methyl group and where $R^{52}$ and $R^{53}$ are isopropyl groups; such as in the case where $R^{51}$ and $R^{52}$ are the same or different C1-C2 alkyl groups and where $R^{13}$ is a C3-C8 branched alkyl group, as in the case where $R^{51}$ and $R^{52}$ are the same or different C1-C2 alkyl groups and where $R^{53}$ is a C3-C6 branched alkyl group, as in the case where $R^{51}$ and $R^{52}$ are the same or different C1-C2 alkyl groups and where $R^{53}$ is a C3-C4 branched alkyl group, and/or as in the case where $R^{51}$ and $R^{52}$ are the same or different C1-C2 alkyl groups and where $R^{53}$ is an isopropyl group. In other illustrative embodiments, at least one of (e.g., exactly one of, exactly two of, or all of) $R^{51}$, $R^{52}$, and $R^{53}$ is a C2-C8 linear alkyl, such as in the case where $R^{51}$ is a methyl group and where $R^{52}$ and $R^{53}$ are the same or different C2-C8 linear alkyl groups, as in the case where $R^{51}$ is a methyl group and where $R^2$ and $R^{53}$ are the same or different C2-C6 linear alkyl groups, as in the case where $R^{51}$ is a methyl group and where $R^{52}$ and $R^{53}$ are the same or different C2-C4 linear alkyl groups, as in the case where $R^{51}$ is a methyl group and where $R^{52}$ and $R^{53}$ are ethyl groups, and/or as in the case where $R^{51}$ is a methyl group and where $R^{52}$ and $R^{53}$ are n-propyl groups; such as in the case where $R^{51}$ and $R^{52}$ are the same or different C1-C2 alkyl groups and where $R^{53}$ is a C2-C8 linear alkyl group, as in the case where $R^{51}$ and $R^{52}$ are the same or different C1-C2 alkyl groups and where $R^{53}$ is a C2-C6 linear alkyl group, as in the case where $R^{51}$ and $R^{52}$ are the same or different C1-C2 alkyl groups and where $R^{53}$ is a C2-C4 linear alkyl group, as in the case where $R^{51}$ and $R^{52}$ are the same or different C1-C2 alkyl groups and where $R^{53}$ is an ethyl group, as in the case where $R^{51}$ and $R^{52}$ are methyl groups and where $R^{53}$ is an ethyl group, as in the case where $R^{51}$ and $R^{52}$ are the same or different C1-C2 alkyl groups and where $R^{53}$ is an n-propyl group, and/or as in the case where $R^{51}$ and $R^{52}$ are methyl groups and where $R^{53}$ is an n-propyl group. As indicated above, these branched acyclic groups can be unsubstituted or substituted, for example, with one, two, three, or more substituents selected, illustratively and independently, from aryl groups (which may themselves be substituted) heterocyclic rings (saturated or unsaturated and optionally substituted), hydroxy groups, alkoxy groups (which is meant to include aryloxy groups (e.g., phenoxy groups)), carboxylic acid derivatives (e.g., carboxylic acid esters, amides, etc.), halogen atoms (e.g., F, Cl, Br, and I), and the like.

As used herein, "cyclic imide" is meant to include cyclic imides having the formula:

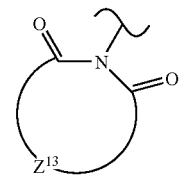

in which $Z^{13}$ represents the atoms needed to complete a substituted or unsubstituted ring or ring system, such as a 5-, 6-, 7-, or 8-membered ring or a 9-, 10-, 11-, 12-, 13-, 14-, 15-, or 16-membered ring system. Illustratively, $Z^{12}$ can be an unsubstituted phthalimide or other cyclic imides having at least one unsubstituted aryl group fused thereto. As further illustration, $Z^{12}$ can be a phthalimide that is substituted, such as with one or more halogen atoms (e.g., F, Cl, Br, or I); or $Z^{12}$ can be another cyclic imides having at least one aryl group fused thereto, in which at least some of the aryl group(s) are substituted, such as with one or more halogen atoms (e.g., F, Cl, Br, or I). For example, $Z^{12}$ can have the formula:

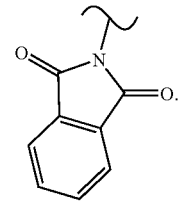

Alternatively, $Z^{12}$ has the formula:

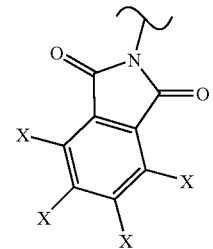

wherein each X represents a halogen atom (which is to be construed as meaning the same or different halogen atom), such as in the case where each X represents a fluorine atom, where each X represents a chlorine atom, where each X represents a bromine atom, or where each X represents a iodine atom. Still alternatively, $Z^{12}$ can have the formula:

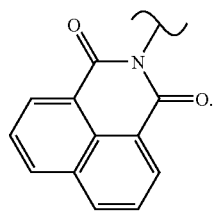

As yet further illustration, $Z^{12}$ an have the formula:

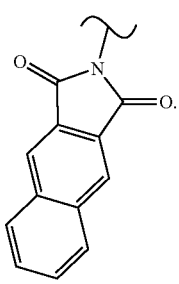

By way of illustration, the compounds of Formula I can have the following formula:

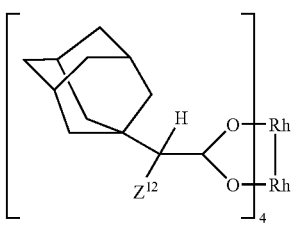

such as, for example, in the case where the compound is substantially chirally pure and has one of the following formulae:

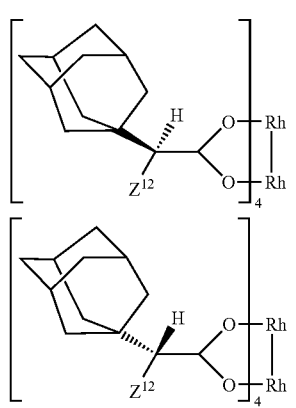

in which $Z^{12}$ is a cyclic imide, such as a cyclic imide having at least one substituted or unsubstituted aryl group fused thereto (e.g., a substituted or unsubstituted phthalimide).

As still further illustration, the compounds of Formula I can have one or more of the following formulae:

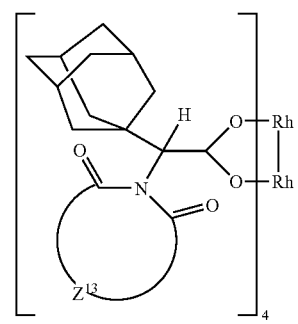

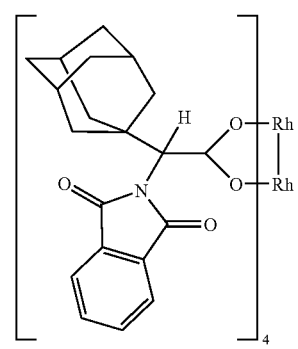

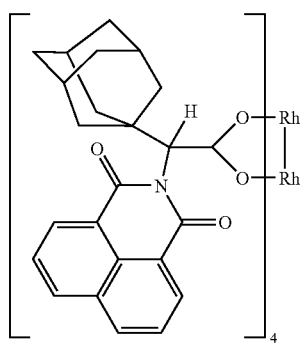

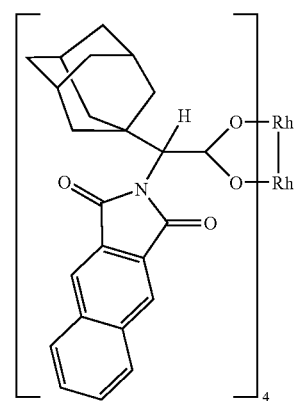

in which $Z^{13}$ is as discussed above, in which the adamantyl group is optionally substituted (e.g., with one of the substituents discussed above), and in which the phenyl ring(s) in the cyclic imide is optionally substituted (e.g., with one or more halogen atoms, such as Cl, Br, I, and the like).

As yet further illustration, the compounds of Formula I can be substantially chirally pure and have one or more of the following formulae:

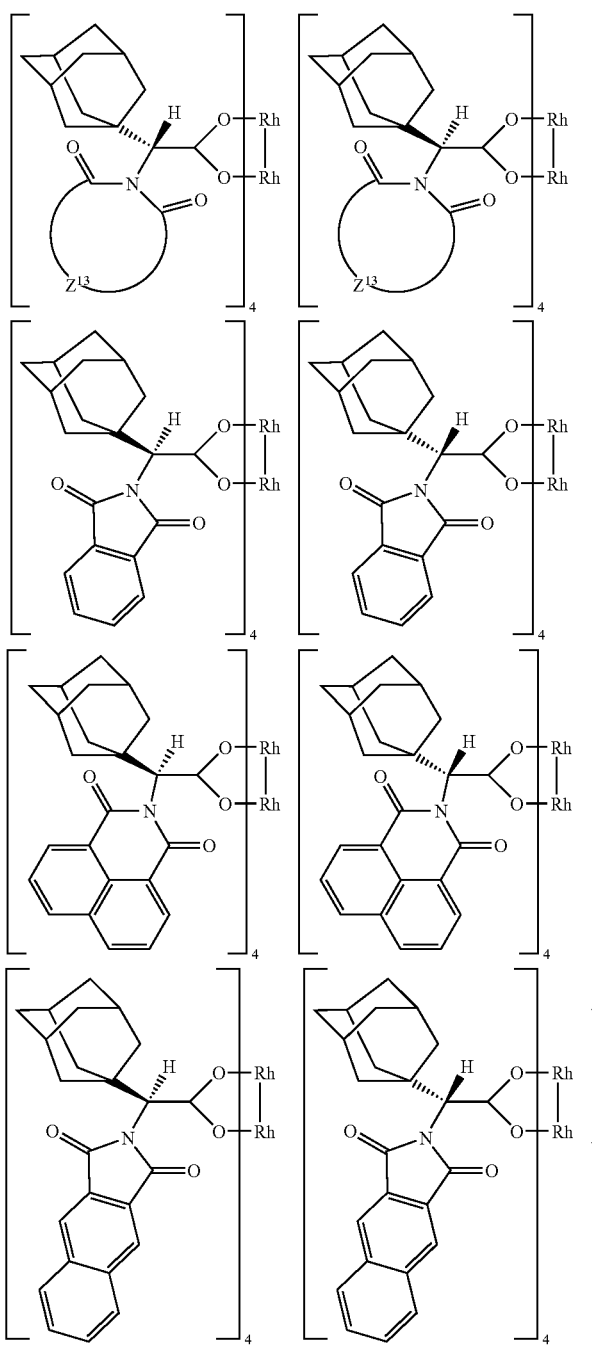

in which $Z^{13}$ is as discussed above, in which the adamantyl group is optionally substituted (e.g., with one of the substituents discussed above), and in which the ring(s) (e.g., the phenyl ring(s)) in the cyclic imide are optionally substituted (e.g., with one or more halogen atoms, such as with one, two, three, four, etc. F, Cl, Br, and/or I atoms).

The aforementioned compounds can be prepared, for example, using the preparative scheme set forth in FIG. 1. Suitable reaction conditions to be used in the various reactions depicted in FIG. 1 will be readily apparent to those skilled in the art in view of the guidance provided in the Examples section of the present application.

Suitable dirhodium catalysts for use in the scheme set forth in FIG. 1 include catalysts having the formula $L_4$Rh—Rh$L_4$ where each of the L's is the same or different and represents a coordinating atom from one or more ligands.

For example, the dirhodium catalyst can be a dirhodium tetracarboxylate catalyst (i.e., a catalyst having the formula $L_4$Rh—Rh$L_4$ where each of the L's represents a carboxylate oxygen from one of four carboxylate groups. Illustrative examples of dirhodium tetracarboxylate catalysts include those having the formula ("Formula III"):

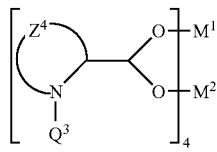

In Formula III, each of $M^1$ and $M^2$ is Rh; $Z^4$ represents the atoms necessary to complete a 3-12 membered heterocyclic ring, such as an alkylene moiety; and $Q^3$ is an electron withdrawing group. As used in this context, "alkylene" refers to a bivalent alkyl group, where alkyl has the meaning given above. Linear, branched, and cyclic alkylenes, as well as examples thereof, are defined in similar fashion with reference to their corresponding alkyl group. Examples of alkylenes include eth-1,1-diyl (i.e., —CH(CH$_3$)—, eth-1,2-diyl (i.e., —CH$_2$CH$_2$—), prop-1,1-diyl (i.e., —CH(CH$_2$CH$_3$)—), prop-1,2-diyl (i.e., —CH$_2$—CH(CH$_3$)—), prop-1,3-diyl (i.e., —CH$_2$CH$_2$CH$_2$—), prop-2,2-diyl (e.g., —C(CH$_3$)$_2$—), cycloprop-1,1-diyl, cycloprop-1,2-diyl, cyclopent-1,1-diyl, cyclopent-1,2-diyl, cyclopent-1,3-diyl, cyclohex-1,1-diyl, cyclohex-1,2-diyl, cyclohex-1,3-diyl, cyclohex-1,4-diyl, but-2-en-1,1-diyl, cyclohex-1,3-diyl, but-2-en-1,4-diyl, but-2-en-1,2-diyl, but-2-en-1,3-diyl, but-2-en-2,3-diyl. Also included in the meaning of the term "alkylene" are compounds having the formula —R'—R"—, where —R' represents a linear or branched alkyl group and R"— represents a cycloalkyl group, such as moieties having the formula:

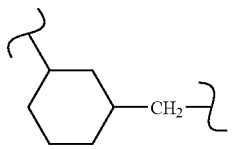

As used in this context, "electron withdrawing group" refers to those groups which are able to withdraw electron density from adjacent positions in a molecule, as determined, for example, by reference to the tables in the classical works which establish the classification of various substituents according to their electron withdrawing character. For example, reference may be made to the classification established by the Hammett scale, such as the one set forth in Gordon et al., *The Chemist's Companion*, New York: John Wiley & Sons, pp. 145-147 (1972) ("Gordon"), which is hereby incorporated by reference. Suitable electron-withdrawing groups include those having a para σ value higher than or equal to about 0.2 or higher than or equal to about 0.3, with reference to the Hammett scale. Illustratively, suitable electron withdrawing groups include esters, amides, ketones, phosphonates, sulfonates, sulfones, nitro, and the like, such as a groups having the formulae —C(O)R⁹, —SO₂R⁹, or —P(O)R⁹R⁹', where each of R⁹ and R⁹' is independently selected from an alkyl group, an aryl group, and an alkoxy group. As noted above, Formula III (and all other formulae set forth in this document which contain one or more chiral centers and which do not specify the stereochemistry of a particular chiral center) is to be construed as encompassing all possible stereochemistries. Thus, for example, Formula III is meant to include (i) compounds in which the unspecified chiral center is entirely in the R configuration, (ii) compounds in which the unspecified chiral center is entirely in the S configuration, and (iii) racemic and other mixtures of (i) and (ii). Illustratively, dirhodium tetracarboxylate catalysts of Formula III are meant to include substantially chirally pure catalysts having one of the following formulae ("Formula IV-A" and "Formula IV-B", respectively):

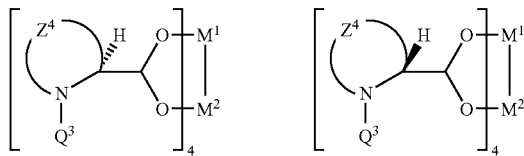

as well as dirhodium tetracarboxylate catalysts of Formula III having D₂ symmetry. Molecules having D₂ symmetry are molecules which have a vertical C₂ axis and a set of two C₂ axes perpendicular to the vertical C₂ axis. D₂ symmetry is further described in, for example, Cotton et al., *Advanced Inorganic Chemistry*, 4th ed., New York: John Wiley & Sons, pages 28-46 (1980), which is hereby incorporated by reference.

Specific examples of dirhodium catalysts for use in the scheme set forth in FIG. 1 having Formulae III and IV include: Rh₂(DOSP)₄, Rh₂(S-DOSP)₄, and Rh₂(R-DOSP)₄, which are compounds having Formulae III, IV-A, and IV-B, respectively, in which each of M¹ and M² is Rh, Z⁴ is a —CH₂CH₂CH₂— group, and Q³ represents a 4-dodecylphenylsulfonyl moiety; and Rh₂(TBSP)₄, Rh₂(S-TBSP)₄, and Rh₂(R-TBSP)₄, which are compounds having Formulae III, IV-A, and IV-B, respectively, in which each of M¹ and M² is Rh, Z⁴ is a —CH₂CH₂CH₂— group, and Q³ represents a 4-t-butylphenylsulfonyl moiety. These and other illustrative compounds having Formulae III, IV-A, and IV-B are described in greater detail in Davies, "Rhodium-Stabilized Vinylcarbenoid Intermediates in Organic Synthesis," *Current Organic Chemistry*, 2:463-488 (1998), which is hereby incorporated by reference. Other suitable dirhodium tetracarboxylate catalysts include those described in U.S. Pat. No. 6,410,746 to Davies, International Publication No. WO 00/64583; and Davies et al., "Novel Dirhodium Tetraprolinate Catalysts Containing Bridging Prolinate Ligands For Asymmetric Carbenoid Reactions," *Tetrahedron Letters*, pages 5287-5290 (1999), each of which is hereby incorporated by reference.

Other suitable dirhodium catalysts include dirhodium tetracarboxamidate catalysts, such as those having the following formula ("Formula V"):

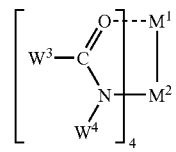

In Formula V, each of M¹ and M² is Rh. W³ represents an alkyl group, an aryl group, an alkoxy group, or an amine group, and W⁴ represents an alkyl group or an aryl group. Alternatively, W³ and W⁴, taken together with the atoms to which they are bonded, represent a 3-12 membered ring, for example, as shown in the following formula ("Formula VI"):

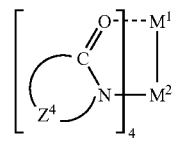

In Formula VI, Z⁴ represents the atoms necessary to complete a 3-12 membered ring. The ring can be substituted or unsubstituted; and it can include additional heteroatoms (i.e., in addition to the N to which Z⁴ is bonded, or it can consist only of carbons (except for the N to which Z⁴ is bonded). Illustratively, Z⁴, together with the carbon and N atoms to which it is bonded, can represents a substituted or unsubstituted C3-C8 lactam ring, a substituted or unsubstituted oxazolidone ring, a substituted or unsubstituted pyrrolidone ring, or a substituted or unsubstituted imidazolidone ring. Specific examples of suitable catalysts of Formula VI include: dirhodium(II) tetrakis(caprolactam); dirhodium(II) tetrakis[methyl 2-oxazolidone-4-carboxylate]; dirhodium(II) tetrakis[methyl 2-oxazolidone-4-(S)-carboxylate]; dirhodium(II) tetrakis[methyl 2-pyrrolidone-5-carboxylate]; dirhodium(II) tetrakis[methyl 2-pyrrolidone-5(R)-carboxylate]; dirhodium(II) tetrakis[methyl 2-pyrrolidone-5(S)-carboxylate]; dirhodium(II) tetrakis [methyl 1-(3-phenylpropanoyl)-2-imidazolidone-4-carboxylate; dirhodium(II) tetrakis[methyl 1-(3-phenylpropanoyl)-2-imidazolidone-4(S)-carboxylate; and adducts (e.g., acetonitrile and/or alcohol adducts) thereof. Methods for producing these and other dirhodium tetracarboxamidate catalysts can be found, for example, in U.S. Pat. No. 5,175,311 to Doyle, which is hereby incorporated by reference.

When used as shown in the scheme set forth in FIG. 1, the aforementioned dirhodium tetracarboxylate catalysts, dirhodium tetracarboxamidate catalysts, and other dirhodium catalysts can be tethered, for example as described in WO 03/018184, which is hereby incorporated by reference. Additionally or alternatively, these dirhodium catalysts can be used in conjunction with an organic ester, as described in WO 03/018183, which is hereby incorporated by reference.

As used in the scheme set forth in FIG. 1, "dioyl diCl" is meant to refer to a di(acid chloride) of a diacid which, upon reaction with an amine, produces a cyclic imide. Illustratively, where the desired cyclic imide has the formula:

suitable dioyl diCls include those having the formula:

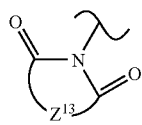

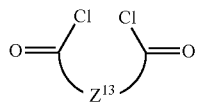

where $Z^{13}$ has the meaning set forth above.

The compounds of the present invention can be used in a variety of dirhodium catalyzed reactions. Illustratively; the compounds of the present invention can be used in dirhodium catalyzed reactions which proceed via a rhodium carbene or via a rhodium nitrene intermediate.

As will be illustrated further in the discussion set forth below and in the Examples section of the present application, the compounds of the present invention can be used in methods for generating a rhodium carbene; and the present invention, in yet another aspect thereof, relates to such methods. More particularly, these methods include contacting a carbene precursor with a compound according to the present invention, for example, a compound having Formula I under conditions effective to generate the rhodium carbene. Suitable carbene precursors include, for example, vinyldiazomethanes and aryldiazomethanes; and these carbene precursors are discussed in greater detail hereinbelow.

Examples of dirhodium catalyzed reactions which proceed via a rhodium carbene intermediate include: insertion reactions (which are meant to include C—H insertions, Si—H insertions, O—H insertions, and N—H insertions), cyclopropanation reactions, annulations (which are meant to include [3+2] annulations and [3+4] annulations), and ω,ω-diarylalkanoate syntheses.

Each of these dirhodium catalyzed reactions is discussed further below, and each involves the use of a compound according to the present invention (e.g., a compound of Formula I) to catalyze decomposition of a vinyldiazomethane or an aryldiazomethane. Thus, in another aspect thereof, the present invention relates to methods for catalyzing decomposition of a vinyldiazomethane or an aryldiazomethane. These methods include contacting the vinyldiazomethane or aryldiazomethane with a compound according to the present invention (e.g., a compound of Formula I), for example, under conditions effective to catalyze decomposition of the vinyldiazomethane or aryldiazomethane. It should be noted, however, that while the catalysis of vinyldiazomethane and aryldiazomethane decomposition can be useful in methods (i) for the generation rhodium carbene intermediates and/or (ii) for the carrying out of insertion reactions, cyclopropanation reactions, annulations, and ω,ω-diarylalkanoate syntheses and/or (iii) for the creation of C—C bonds, other carbene precursors can be used in conjunction with the compounds of the present invention (e.g., those having Formula I), for example, to generate rhodium carbene intermediates.

As noted above, the compounds of the present invention can be used in insertion reactions.

One such insertion reaction relates to a method for producing a compound having the formula ("Formula XV"):

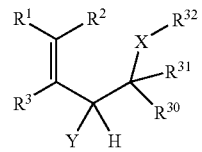

$R^1$, $R^2$, and $R^3$ are independently selected from H, alkyl, aryl, or vinyl, or $R^1$ and $R^3$, together with the atoms to which they are bonded, form a 5-12 membered ring, such as a cyclohexene ring, or a cyclohexa-1,3-diene ring. The method can be used to prepare compounds in which $R^1$ and $R^3$, together with the atoms to which they are bonded, form an aromatic ring, such as a substituted or unsubstituted phenyl ring, pyridine ring, thiophene ring, indole ring, etc. In the case where $R^1$ and $R^3$, together with the atoms to which they are bonded, form a phenyl ring, the compound produced by this method can have the formula ("Formula XVI"):

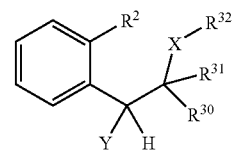

Y is an electron withdrawing group, examples of which include moieties having the formulae: —C(O)$R^{77}$, —SO$_2R^{77}$, and —P(O)$R^{77}R^{77'}$. In these formulae, each of $R^{77}$ and $R^{77'}$ is independently selected from an alkyl group, an aryl group, and an alkoxy group. Illustratively, Y can have the formula CO$_2R^{12}$ where $R^{12}$ is an alkyl group or an aryl group. By way of further illustration, Y can be a carboxylic ester, an electron withdrawing group other than an carboxylic ester, —COOMe, a carboxylic ester other than —COOMe, or an electron withdrawing group other than —COOMe.

X is CH$_2$, O, or NR$^{11}$, and $R^{11}$ is H, an alkyl group, an aryl group, an acyl group, an alkoxycarbonyl group, or a silyl group having the formula —SiR$^{33}R^{34}R^{35}$, where $R^{33}$, $R^{34}$, and $R^{35}$ are independently selected from an alkyl group and an aryl group.

Each of $R^{30}$ and $R^{31}$ is independently selected from the group consisting of H, alkyl, aryl, and vinyl. $R^{32}$ is an alkyl group, an aryl group, an acyl group, an alkoxycarbonyl group, or a silyl group having the formula —SiR$^{36}R^{37}R^{38}$, where $R^{36}$, $R^{37}$, and $R^{38}$ are independently selected from an alkyl group and an aryl group. Alternatively, $R^{31}$ and $R^{32}$, together with the atoms to which they are bonded, can form a 5-12 membered ring, such as a cyclopentyl or cyclohexyl ring (in the case where X is —CH$_2$—), a piperidinyl ring (in the case where X is N), or a tetrahydrofuranyl or a tetrahydropyranyl ring (in the case where X is O). Illustratively, this method is well-suited for forming compounds having Formula XV in which X is not CH$_2$ when each of $R^{30}$ and $R^{31}$ is H.

The method includes providing a diazo compound having the formula ("Formula XVII"):

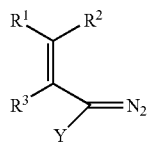

in which $R^1$, $R^2$, $R^3$, and Y have the same meanings as given above with reference to Formula XV. The method further includes converting the diazo compound with a compound having the formula ("Formula XVIII"):

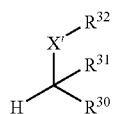

in the presence of a dirhodium catalyst of the present invention and under conditions effective to produce the compound. In compound XVIII, $R^{30}$, $R^{31}$, and $R^{32}$ are defined as they are above with regard to Formula XV. When, in the desired product, X is $CH_2$ or O, X' in Formula XVIII is $CH_2$ or O, respectively. When, in the desired product, X is $NR^{11}$, X' in Formula XVIII is $NR^{11'}$ and $R^{11'}$ is an alkyl group, an aryl group, an acyl group, an alkoxycarbonyl group (e.g., BOC or another alkoxycarbonyl amine protecting group), or a silyl group (e.g., a triarylsilyl group, or a trialkylsilyl group).

Suitable dirhodium catalysts for carrying out the conversion of XVII with XVIII are those having Formulae I, as defined and discussed above. Other suitable dirhodium catalysts for carrying out the conversion of XVII with XVIII are chiral dirhodium catalysts, such as those having Formula II-A or Formula II-B.

Illustratively, the reaction can be carried out by mixing the catalyst with the compound of Formula XVIII. In the case where the compound of Formula XVIII is a liquid (e.g., in the case where the compound of Formula XVIII is tetrahydrofuran, tetrahydropyran, N-(tert-butyloxycarbonyl)pyrrolidine, N-(tert-butyloxycarbon-yl)piperidine, cyclopentane, cyclohexane, etc.), this can be effected without the use of additional solvent. Alternatively, the mixture can be formed using an inert solvent or a solvent which is significantly less reactive toward the diazo compound of Formula XVII than is the compound of Formula XVIII. As an example, it has been found that when the compound of Formula XVIII is tetrahydrofuran, the catalyst, and tetrahydrofuran can be mixed neat (i.e., using tetrahydrofuran as the solvent and without the use of additional solvent), or hexanes can be used as a reaction medium.

Once the catalyst and compound of Formula XVIII are mixed, the diazo compound of Formula XVII is added, for example with stirring. This addition can be carried out in a single portion, continuously, or batchwise. Slow, dropwise addition can be effected, for example, using a syringe pump. The amount of diazo compound of Formula XVII added is generally dependent on the amount of the compound of Formula XVIII present in the reaction mixture. Illustratively, the mole ratio of the compound of Formula XVIII to the diazo compound of Formula XVII is from about 1:10 to about 10:1, such as from about 6:1 to about 1:1 and/or from about 4:1 to about 2:1. The addition can be carried out at any suitable temperature from the freezing point to the boiling point of the solvent and/or the compound of Formula XVIII. For example, the addition can be carried out from about −50° C. to about 60° C. Room temperature addition and addition at about 10° C. are illustrative. Illustratively, in one embodiment of the present invention where diastereomerically and/or enantiomerically pure product is desired, reaction conditions can be optimized by adjusting the addition temperature. Although not intending to be limitative in any way on the scope of the present invention, it is believed that (i) formation of diastereomerically and/or enantiomerically pure product can be favored by lower addition temperatures (e.g., from about −50° C. to about 10° C.); and (ii) yield and improved diastereoisomeric and/or enantiomeric purity can be improved by performing the reaction substantially in the absence of oxygen. As used herein, "substantially in the absence of oxygen" means that the liquid reactants and solvents (if any) employed in carrying out the reaction are degassed, for example by bubbling an inert gas (e.g., nitrogen or argon) therethrough, that the reaction is carried out under blanket of inert gas, and that all transfers (subsequent to degassing) are carried out such that ambient air is excluded (e.g., by using rubber septums, gas tight syringes, and the like).

The conversion of the compound of Formula XVII with a compound of Formula XVIII to produce either or both diastereomers of a compound of Formula XV described above can be used for preparing compounds having the formula ("Formula XIX"):

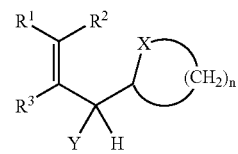

In this case, the conversion of the diazo compound of Formula XVII is carried out with a cyclic compound having the formula ("Formula XX"):

in which X' is defined as above and n is 3-10. In one illustrative embodiment, $R^1$ and $R^3$, together with the atoms to which they are bonded, form a phenyl ring, and Y has the formula $—CO_2R^{10}$ where $R^{10}$ is an alkyl or aryl group. The method can be used, for example, to make compounds in which X is $NR^{11}$ and in which n is 3 or 4. The method is also suitable for making compounds having the formulae ("Formula XXI-A" and "Formula XXI-B", respectively):

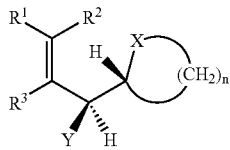 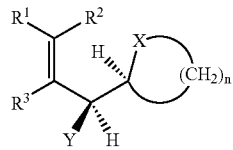

in which case the dirhodium catalyst employed is a chiral dirhodium catalyst. For example, by using the S-isomer of compounds having Formulae I, as defined and discussed above, compounds of Formula XXI-B which are substantially enantiomerically pure (e.g., >80% ee, >90% ee, >95% ee, >98% ee, and/or >99% ee) can be prepared. Examples of compounds having Formula XXI-A and XXI-B include those in which X is $NR^{11}$, n is 3 or 4, Y is $CO_2R^{12}$, $R^{12}$ is alkyl or aryl, and $R^1$ and $R^3$, together with the atoms to which they are bonded, form an aromatic ring, such as those compounds of Formulae XXI-A or XXI-B in which X is NH, $R^{12}$ is a methyl group, and $R^1$ and $R^3$, together with the atoms to which they are bonded, form a phenyl ring. Such compounds can have one of the following formulae ("Formula XXII-A" and "Formula XXII-B", respectively):

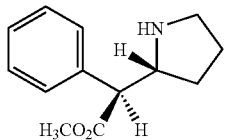 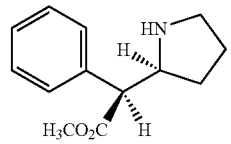

or one of the following formulae ("Formula XXII-C" and "Formula XXII-D", respectively):

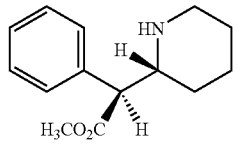 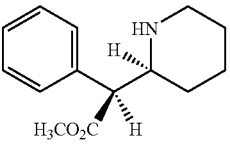

the latter of which is also referred to as threo methylphenidate and which is believed to be the biologically active form of RITALIN™. Where stereospecificity is not important, racemic mixtures of compounds having Formulae II-A and II-B can be employed in the method of the present invention to produce the racemic methylphenidate.

The method of the present invention can also be used to prepare compounds having Formula XV in which X is $NR^{11}$ and in which $R^{31}$ and $R^{32}$, together with the atoms to which they are bonded, represent a ring having the formula ("Formula XXIII"):

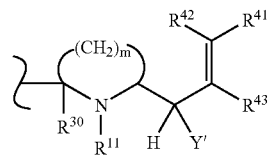

where $R^{30}$ is H. That is, the method can be used to prepare compounds having the formula ("Formula XXIV"):

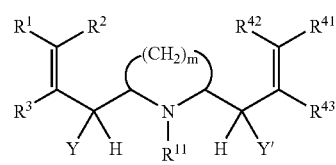

In these formulae, $R^{41}$, $R^{42}$, and $R^{43}$ are independently selected from H, alkyl, aryl, or vinyl, or $R^{41}$ and $R^{43}$, together with the atoms to which they are bonded, form a 5-12 membered ring. Y' is an electron withdrawing group, for example, the electron withdrawing groups discussed above with regard to Y, and m is 2-9. The reaction involves providing a diazo compound having Formula XVII and converting the diazo compound with a cyclic amine having the formula ("Formula XXV"):

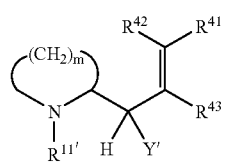

in the presence of a catalyst of the present invention and under conditions effective to produce the compound. Suitable conditions for this reaction are the same as the ones discussed above with regard to the conversion of compounds of Formula XVII with compounds of Formula XVIII. By using a chiral catalyst, compounds having the formula ("Formula XXVI"):

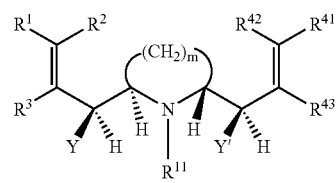

can be produced.

A variety of methods can be used to prepare the cyclic amine having Formula XXV, such as the method that is described above with regard to preparing compounds having Formula XIX using diazo compounds of Formula XVII, cyclic compounds of Formula XX, and a catalyst of the present invention. Rather than running the reaction in two steps (i.e., by first reacting a diazo compounds of Formula XVII with a cyclic compound of Formula XX in which X is N to produce a cyclic amine having Formula XIX and then reacting the cyclic amine having Formula XIX with a diazo compound having Formula XVII to produce the desired compound of Formula XXIV), the reaction can be carried out in a single step, for example, by contacting the cyclic compound of Formula XX in which X is N with at least two equivalents of a diazo compound of Formula XVII. Reaction conditions suitable for carrying out this one step transformation include those discussed above with regard to the two step method. It will be understood that the "one step" and "two step" labels assigned to the above methods are only for brevity and that these methods can, optionally, further additional steps (e.g., a second, third, fourth, etc. step in a one step method; and a third, fourth, etc. step on a two step method). Illustratively, during the first part of the reaction (i.e., during the addition of the first half of the diazo compound having Formula XVII), the reaction is carried out with cooling (e.g., from about −50° C. to about 0° C.). Then the reaction mixture is warmed, and the second part of the reaction (i.e., during the addition of the second half of the diazo compound having Formula XVII) is carried out at elevated temperatures (e.g., from about 20° C. to about 100° C.). Alkanes having melting points of less than about −50° C. and boiling points greater than about 60° C. are the suitable solvents for this reaction, but the nature of the solvent is not particularly critical and alternatives can be used.

The compounds prepared by the above method (i.e., compounds having Formulae XV, XVI, XIX, XXI-A, XXI-B, XXII-A, XXII-B, XXII-C, XXII-D, XXIV, and XXVI) are appropriately functionalized for further conversion by, for example, ester reduction or Grignard addition to highly functionalized bases. In the case where a chiral catalyst is employed, e.g., the S-isomer of compounds having Formula I, as defined and discussed above, these compounds can be used as $C_2$ symmetric bases, or, as indicated above, they can be further converted (e.g., by ester reduction or Grignard addition) to highly functionalized $C_2$ bases. $C_2$ bases are very useful for controlling stereochemistry in organic synthesis, for example, as described in Takahata et al., "New Entry to C2 Symmetric Trans-2,6-bis(hydroxymethyl)piperidine Derivatives Via the Sharpless Asymmetric Dihydroxylation," *Tetrahedron-Asymmetry*, 6:1085-1088 (1995) and in Bennani et al., "Trans-1,2-diaminocyclohexane Derivatives as Chiral Reagents, Scaffolds, and Ligands for Catalysis—Applications in Asymmetric Synthesis and Molecular Recognition," *Chemical Reviews*, 97:3161-3195 (1997), which are hereby incorporated by reference.

Further examples and details of using dirhodium catalysts to effect insertions can be found, for example, in Davies et al., "Catalytic Asymmetric C—H Activation of Silyl Enol Ethers as an Equivalent of an Asymmetric Michael Reaction," *J. Am. Chem. Soc.*, 123(9):2070-2071 (2001); Davies et al., "Kinetic Resolution and Double Stereodifferentiation in Catalytic Asymmetric C—H Activation of 2-Substituted Pyrrolidines," *Organic Letters*, 3(11):1773-1775 (2001); Davies et al., "Asymmetric Intramolecular C—H Insertions of Aryldiazoacetates," *Organic Letters*, 3(10):1475-1477 (2001); Catalytic Asymmetric C—H Activation of Alkanes and Tetrahydrofuran," *J. Am. Chem. Soc.*, 122(13):3063-3070 (2000); Davies et al., "Highly Regio-, Diastereo-, and Enantioselective C—H Insertions of Methyl Aryldiazoacetates into Cyclic N-Boc-Protected Amines. Asymmetric Synthesis of Novel $C_2$-Symmetric Amines and threo-Methylphenidate," *J. Am. Chem. Soc.*, 121(27):6509-6510 (1999); Davies et al., "Catalytic Asymmetric Synthesis of Syn-Aldol Products from Intermolecular C—H Insertions Between Allyl Silyl Ethers and Methyl Aryldiazoacetates," *Organic Letters*, 1(3):383-385 (1999); Davies, "Rhodium-Stabilized Vinylcarbenoid Intermediates in Organic Synthesis," *Current Organic Chemistry*, 2:463-488 (1998); Davies et al., "Recent Progress in Asymmetric Intermolecular C—H Activation by Rhodium Carbenoid Intermediates," *Journal of Organometallic Chemistry*, 617-618:47-55 (2001); Davies, "Dirhodium Tetra(N-arylsulfonylprolinates) as Chiral Catalysts For Asymmetric Transformations of Vinyl- and Aryldiazoacetates," *Eur. J. Org. Chem.*, pages 2459-2469 (1999); Davies, "Asymmetric Synthesis Using Rhodium-Stabilized Vinylcarbenoid Intermediates," *Aldrichimica Acta*, 30(4):107-114 (1997); U.S. Pat. No. 6,410, 746 to Davies; and International Publication No. WO 00/64583. Collectively, these references are referred to herein as the "Insertion References", and each of these references is hereby incorporated by reference. The reactions set forth in the Insertion References and other references relating to dirhodium catalyzed insertion reactions can be carried out using a catalyst of the present invention in place of the dirhodium catalysts described in the Insertion References. As noted above, the catalyst of the present invention can be used in conjunction with an organic ester, for example, of the types and amounts specified in WO 03/018183, which is hereby incorporated by reference.

The compounds of the present invention (e.g., those having Formula I, Formula II-A, and/or Formula II-B) can also be used in connection with other insertion reactions, as well as with cyclopropanation reactions. Such other insertion reactions and such cyclopropanation reactions are illustrated by the following method for producing a compound having the formula ("Formula XXVII"):

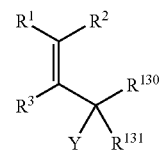

In Formula XXVII, $R^1$, $R^2$, and $R^3$ are independently selected from H, alkyl, aryl, or vinyl, or $R^1$ and $R^3$, together with the atoms to which they are bonded, form a 5-12 membered ring. Y is an electron withdrawing group (e.g., an ester group). $R^{131}$ is H, and $R^{130}$ is an alkyl group, an aryl group, an alkoxy group, an amine group, or a silyl group; or $R^{130}$ and $R^{131}$, together with the atom to which they are bonded, form a substituted or unsubstituted cyclopropane moiety. The method includes providing a diazo compound having the formula ("Formula XXVIII"):

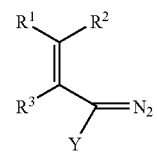

(in which $R^1$, $R^2$, $R^3$, and Y are defined as they are above with regard to Formula XXVII) and converting the diazo compound of Formula XXVIII to the compound of Formula XXVII in the presence of a catalyst of the present invention and under conditions effective to produce the compound of Formula CII.

In cases where $R^{131}$ is H, and $R^{130}$ is an alkyl group, an aryl group, an alkoxy group, an amine group, or a silyl group, this reaction is a C—H, C—C, C—N, or C—Si insertion, and suitable reactants for effecting the conversion of the diazo compound of Formula XXVIII to the compound of Formula XXVII can be readily ascertained by one skilled in the art. Examples of such reactions are set forth in the Insertion References, and each of these references is hereby incorporated by reference. The reactions set forth in the Insertion References and other references relating to dirhodium catalyzed insertion reactions can be carried out using the catalyst of the present invention in place of the dirhodium catalysts described in the Insertion References.

The above-described insertion reactions exemplify the present invention's usefulness in catalyzing aryldiazomethane or vinyldiazomethane insertion reactions in which aryldiazomethanes or vinyldiazomethanes are contacted with a compound according to the present invention under conditions effective to catalyze the aryldiazomethane or vinyldiazomethane insertion reaction. These methods provide new and useful ways to make compounds (such as the compounds illustrated by Formulae XV, XVI, XIX, XXI-A, XXI-B, XXII-A, XXII-B, XXII-C, XXII-D, XXIV, XXVI, and XXVII (in cases where $R^{131}$ is H)) and to produce C—C bonds.

In cases where $R^{130}$ and $R^{131}$, together with the atom to which they are bonded, form a substituted or unsubstituted cyclopropane moiety, the compound of Formula XXVII can have the formula ("Formula XXIX"):

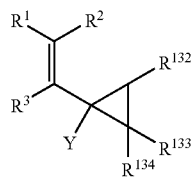

Such reactions are commonly referred to as cyclopropanation reactions. In Formula XXIX, each of $R^{132}$, $R^{133}$, and $R^{134}$ can independently represent H, an alkyl group, an aryl group, a silyloxy group, an alkoxy group, a halogen, an amine group, or an alkyl or aryl thiol group. Alternatively, $R^{132}$ and $R^{133}$, together with the atoms to which they are bonded, can form a 4-12 membered ring. Still alternatively, $R^{133}$ and $R^{134}$, together with the atom to which they are bonded, can form a 3-12 membered ring. Compounds of Formula XXIX can be produced by converting the diazo compound of Formula XXVIII using a compound having the formula ("Formula XXX"):

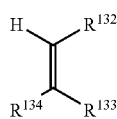

in which $R^{132}$, $R^{133}$, and $R^{134}$ are defined as they are above with regard to Formula XXIX. The reaction is carried out using a catalyst of the present invention (e.g., a compound of Formula I).

Once formed, compounds of Formula XXIX can be used in an number of ways.

For example, compounds of Formula XXIX in which at least one of $R^1$ and $R^2$ is H and in which $R^{132}$ is an electron donating group can be converted to cyclopentenes, for example, by treating the compound of Formula XXIX with a Lewis acid, such as diethyl aluminum chloride. As used herein, "electron donating group" refers to those groups which are able to inject electron density from adjacent positions in a molecule, as determined, for example, by reference to the classification established by the Hammett scale, such as the one set forth in Gordon, which is hereby incorporated by reference. Suitable electron-donating groups include those having a para σ value less than or equal to about zero (e.g., less than or equal to about −1, and/or less than or equal to about −2 with reference to the Hammett scale. Particular examples of electron withdrawing groups are alkoxy groups.

Alternatively, compounds of Formula XXIX in which $R^1$ and $R^2$ are H, in which $R^{132}$ is an electron donating group (e.g., an alkoxy group), and in which $R^3$ is a silyloxy group can be converted to dihydrofurans, for example, by treating the compound of Formula XXIX with a fluoride, such as tetrabutylammonium fluoride.

Still alternatively, compounds of Formula XXIX in which at least one of Rp and $R^2$ is H, in which $R^{132}$ is an electron donating group (e.g., an alkoxy group), in which Y is a carboxylic acid ester of the formula —COOR$^{160}$, and in which $R^{160}$ is a tertiary alkyl moiety (e.g., a t-butyl group) can be converted to butenolides, for example, by treating the compound of Formula XXIX with a Lewis acid catalyst, such a boron halide (e.g., $BF_3$ or $BBr_3$) or another Lewis acid catalyst containing boron.

Compounds of Formula XXIX can also be used to prepare compounds having the formula ("Formula XXXI"):

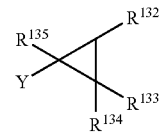

where each of $R^{132}$, $R^{133}$, $R^{134}$, and Y are defined as they were with regard to Formula XXIX and where $R^{135}$ is a carboxylic acid group, a carboxylic acid derivative (e.g., a carboxylic acid ester, a carboxylic acid amide, etc.), or an amino group (e.g., a unsubstituted, monosubstituted, or disubstituted amino group). The conversion of compounds of Formula XXIX to compounds of Formula XXXI in which $R^{135}$ is a carboxylic acid or carboxylic acid derivative can be effected, for example, by treating the compound of Formula XXIX with an oxidative alkene cleavage reagent, such as $RuCl_3/NaIO_4$. Compounds of Formula XXXI in which $R^{135}$ is a carboxylic acid or carboxylic acid derivative can be further converted to compounds of Formula XXXI in which $R^{135}$ is an amino group, for example by treatment with triethylamine, diphenylphosphoryl azide, and t-butyl alcohol; followed by treatment with di-t-butyl dicarbonate to produce a Boc-protected amine; and conversion of the Boc-protected amine to the free amine using, for example, strong acid (e.g., 3 N HCl in EtOAc). Using this method in conjunction with enantiomerically pure compounds of Formula XXIX (formed, for example, by using a catalyst of the present invention that is optically pure, such as one having Formula II-A or Formula II-B), each of the four stereoisomers of 2-phenylcyclopropan-1-amino acid can be produced.

Compounds of Formula XXIX can also be converted to compounds having the formula ("Formula XXXII"):

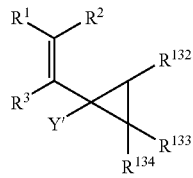

where each of $R^1$, $R^2$, $R^3$, $R^{132}$, $R^{133}$, and $R^{134}$ are defined as they were with regard to Formula XXIX and where Y' is an alkyl group, an aldehyde group, a ketone, or a vinyl group. As one illustrative example, $R^2$ can be H; $R^1$ and $R^3$, together with the atoms to which they are bonded, can form a phenyl group; $R^{132}$ can be H; $R^{133}$ can be a 4-alkoxyphenyl group; $R^{134}$ can be a phenyl group; Y can be a carboxylic acid ester; and Y' can be an aldehyde group, a hydroxymethyl group, a vinyl group, or an ethyl group. Compounds of Formula XXIX can be converted to a compound of Formula XXXII where Y' is a hydroxymethyl group by treating the compound of Formula XXIX with a reducing agent, e.g., $LiAlH_4$, in an inert solvent (e.g., tetrahydrofuran) at an appropriate temperature (e.g. from about $-78°$ C. to about $0°$ C.). The resulting alcohol can then be oxidized (e.g., under Swern conditions) to produce the compound of Formula XXXII where Y' is an aldehyde group. The aldehyde can then be converted to the corresponding alkene (i.e., a compound of Formula XXXII where Y' is a vinyl group), for example, by treatment with $Ph_3P=CH_2$. The alkene can then be hydrogenated (e.g., using $Rh/Al_2O_3$) to produce a compound of Formula XXXII where Y' is an ethyl group. For example, using this sequence of reactions in conjunction with a compounds of Formula XXIX in which $R^1$ and $R^3$, taken together with the atoms to which they are bonded, represent a phenyl ring; in which $R^{133}$ is a phenyl group; and in which $R^{134}$ is a 4-(2-chloroethoxy)phenyl group, and further treatment of the resulting compound of Formula XXXII where Y' is an ethyl group with dimethylamine in the presence of sodium iodide in $DMF-H_2O$ at appropriate temperature (e.g., about $55°$ C.), a cyclopropyl analog of tamoxifen can be produced. Using this method in conjunction with enantiomerically pure compounds of Formula XXIX (formed, for example, by using a catalyst of the present invention that is optically pure, such as one having Formula II-A or Formula II-B), the stereochemistry of the chiral centers in this tamoxifen analog can be controlled. Further details regarding the conversion of Compounds of Formula XXIX to compounds of Formula XXXII can be found, for example, in Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters*, 2(6):823-826 (2000), which is hereby incorporated by reference.

Compounds of Formula XXXI can also be used to synthesize compounds having the formula ("Formula XXXIII"):

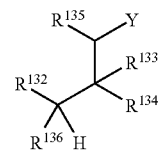

where each $R^{132}$, $R^{133}$, $R^{134}$, and Y are defined as they were with regard to Formula XXXI; where $R^{135}$ is a carboxylic acid group or a carboxylic acid derivative; and where $R^{136}$ represents an aryl group or an alkyl group. The synthesis includes providing a compound having Formula XXXI in which $R^{135}$ is a carboxylic acid group or a carboxylic acid derivative and converting this compound of Formula XXXI to the compound of Formula XXXIII using, for example, an aryl or alkyl cuprate (e.g., having the formula $[R^{136}]_2CuLi_2CN$).

Compounds of Formula XXXIII in which $R^{135}$ is a carboxylic acid group or a carboxylic acid derivative and in which $R^{132}$ has the formula:

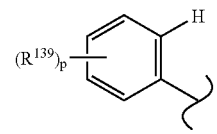

where each $R^{139}$ independently represents an alkyl group, an aryl group, a halogen, a hydroxy group, an amino group, a thiol group, an alkyl thiol group, an aryl thiol group or two or more of $R^{139}$, together with that atoms to which they are bonded, form a 5-12 membered ring; and where p represents an integer from 0 to 4 can be converted to compounds having the formula ("Formula XXXIV"):

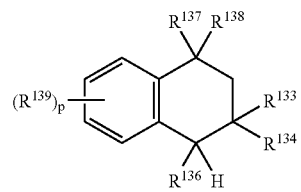

where each of $R^{133}$, $R^{134}$, and $R^{136}$ is defined as it was with regard to Formula XXXIII; where $R^{137}$ is H and $R^{138}$ represents an amino group or $R^{137}$ and $R^{138}$, together with the carbon atom to which they are bonded, represent a carbonyl moiety; and where $R^{139}$ is defined as above. For example, compounds of Formula XXXIII can be decarboxylated and then acylated (e.g., using a Friedel Crafts acylation method) to produce compounds of Formula XXXIV where $R^{137}$ and $R^{138}$, together with the carbon atom to which they are bonded, represent a carbonyl moiety. Reductive amination can be used to convert $R^{137}$ and $R^{138}$ from a $=O$ group to an amine group.

Further details with regard to the aforementioned cyclopropanation reactions and the reactions which use the products of these cyclopropanation reactions can be found, for example, in Davies et al., "Asymmetric Cyclopropanations by Rhodium (II) N-(Arylsulfonyl)prolinate Catalyzed Decomposition of Vinyldiazomethanes in the Presence of Alkenes. Enantioselective Synthesis of the Four Stereoisomers of 2-Phenylcyclopropan-1-amino Acid," *J. Am. Chem. Soc.*, 118(29):6897-6907 (1996); Davies et al., "Stereoselectivity of Methyl Aryldiazoacetate Cyclopropanations of 1,1-Diarylethylene. Asymmetric Synthesis of a Cyclopropyl Analogue of Tamoxifen," *Organic Letters*, 2(6):823-826 (2000); Davies et al., "Effect of Diazoalkane Structure on the Stereoselectivity of Rhodium(II) (S)—N-(Arylsulfonyl)prolinate Catalyzed Cyclopropanations," *Tetrahedron Letters*, 37(24):4133-4136 (1996); Davies et al., "Effect of Catalyst on the Diastereoselectivity of Methyl Phenyldiazoacetate Cyclopropanations," *Tetrahedron Letters*, 39:8811-8812 (1998); Davies et al., "Enantioselective Synthesis of Fused Cycloheptadienes by a Tandem Intramolecular Cyclopropanation/Cope Rearrangement Sequence," *J. Org. Chem.*, 64(23):8501-8508 (1999); Davies, "Rhodium-Stabilized Vinylcarbenoid Intermediates in Organic Synthesis," *Current Organic Chemistry*, 2:463-488 (1998); Davies et al., "Effect of Rhodium Carbenoid Structure on Cyclopropanation Chemoselectivity," *Tetrahedron*, 56:4871-4880 (2000); Davies, "Dirhodium Tetra(N-arylsulfonylprolinates) as Chiral Catalysts For Asymmetric Transformations of Vinyl- and Aryldiazoacetates," *Eur. J. Org. Chem.*, pages 2459-2469 (1999); Nagashima et al., "Catalytic Asymmetric Solid-Phase Cyclopropanation," *J. Am. Chem. Soc.*, 123(11):2695-2696 (2001); and Davies, "Asymmetric Synthesis Using Rhodium-Stabilized Vinylcarbenoid Intermediates," *Aldrichimica Acta*, 30(4):107-114 (1997), each of which is hereby incorporated by reference. All of the cyclopropanation reactions set forth in the above-identified references can be modified by using the catalysts of the present invention.

The above-described reactions exemplify the present invention's usefulness in catalyzing aryldiazomethane or vinyldiazomethane cyclopropanation reactions in which aryldiazomethanes or vinyldiazomethanes are contacted with a catalyst according to the present invention under conditions effective to catalyze the aryldiazomethane or vinyldiazomethane cyclopropanation reaction. These methods provide new and useful ways to make compounds (such as the compounds illustrated by Formulae XXVII (in cases where $R^{130}$, $R^{131}$, and the carbon to which they are bonded form a cyclopropane moiety), XXIX, and XXXI-XXXIV) and to produce C—C bonds.

The catalysts of the present invention can also be used to produce optionally substituted cycloheptadienes or optionally substituted bicyclooctadienes. In this method, a diazo compound having the formula ("Formula XXXV"):

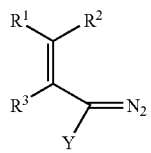

is provided. In Formula XXXV, Y is an electron withdrawing group; and $R^1$, $R^2$, and $R^3$ are independently selected from H, alkyl, aryl, silyloxy, or vinyl, or $R^1$ and $R^3$, together with the atoms to which they are bonded, form a 5-12 membered ring. The diazo compound having the Formula XXXV is then converted with a optionally substituted homocyclic, heterocyclic, or non-cyclic diene. Suitable optionally substituted homocyclic, heterocyclic, or non-cyclic diene include those having the formula ("Formula XXXVI"):

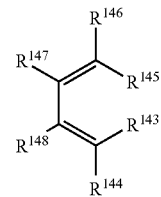

In Formula XXXVI, each of $R^{144}$, $R^{146}$, $R^{147}$, and $R^{148}$ independently represent an alkyl group, an aryl group, an alkoxy group, a halogen, hydrogen, an acyl group, a hydroxy group, a thiol group, an alkyl thiol or aryl thiol group, a carboxylic acid group, a carboxylic acid derivative, or a silyloxy group, or two or more of $R^{144}$, $R^{146}$, $R^{147}$, and $R^{148}$, together with the atom or atoms to which they are bonded, form a 5-12 membered ring. Each of $R^{143}$ and $R^{145}$ independently represents an alkyl group, an aryl group, an alkoxy group, a halogen, hydrogen, an acyl group, a hydroxy group, a thiol group, an alkyl thiol or aryl thiol group, a carboxylic acid group, a carboxylic acid derivative, or a silyloxy group, or $R^{143}$ and $R^{145}$ together represent a —O— moiety, a —S— moiety, a substituted or unsubstituted bivalent amino moiety (e.g., a substituted or unsubstituted bivalent amino moiety having the formula —N($R^{150}$)— in which $R^{150}$ is H, an aryl group, or alkyl group), or a substituted or unsubstituted methylene or ethylene moiety. Examples of optionally substituted cycloheptadienes or optionally substituted bicyclooctadienes that can be produced using this method include optionally substituted cyclohepta-1,5 dienes and optionally substituted 8-aza-bicyclo [3.2.1] octa-2,6 dienes, such as those having the formula ("Formula XXXVII"):

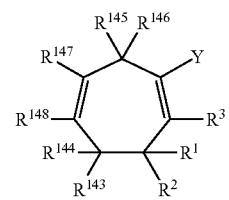

in which $R^{143}$, $R^{144}$, $R^{145}$, $R^{146}$, $R^{147}$, and $R^{148}$ have the same meanings as set forth above with regard to Formula XXXVI and in which $R^1$, $R^2$, $R^3$, and Y have the same meanings as set forth above with regard to Formula XXXV. The reaction is carried out using a catalyst of the present invention. Other reaction conditions suitable for carrying out the conversion of compounds having Formula XXXV with optionally substituted homocyclic, heterocyclic, or non-cyclic diene are the same as those discussed above with regard to insertion reactions. These reactions can be carried out stereospecifically, for example with optically pure catalysts (such as those having Formula II-A or Formula II-B). Alternatively, the reaction can be carried out racemically, in which case racemic mixtures of catalysts having Formulae II-A and II-B can be employed.

Compounds of Formula XXXVII in which $R^{143}$ and $R^{145}$ together represent a substituted or unsubstituted bivalent amino moiety having the formula —N($R^{150}$)— (in which $R^{150}$ is H, an aryl group, or alkyl group) can be readily converted to 3-aryltropanes, for example by reaction the compound of Formula XXXVII with a Grignard reagent (e.g., having the formula $R^{151}$—Mg—X, where $R^{151}$ is an aryl group and X is a halogen). Illustratively, the 3-aryltropane can have the formula ("Formula XXXVIII"):

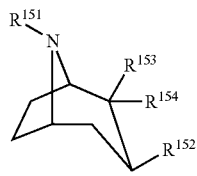

where $R^{151}$ is H, an aryl group, or an alkyl group; $R^{152}$ is an aryl group; $R^{153}$ represents H or a C1-C12 ketone; and $R^{154}$ represents H or a C1-C12 ketone. Further details regarding the dirhodium catalyzed preparation of cycloheptadienes and bicyclooctadienes, as well as the production of tropanes and other useful materials from these cycloheptadienes and bicyclooctadienes are available in U.S. Pat. No. 5,760,055 to Davies; U.S. Pat. No. 5,591,854 to Davies; Davies, "[3+4] Annulations Between Rhodium-Stabilized Vinylcarbenoids and Dienes," *Advances in Cycloaddition*, 5:119-164 (1999); Davies et al., "Tandem Asymmetric Cyclopropanation/Cope Rearrangement. A Highly Diastereoselective and Enantioselective Method for the Construction of 1,4-Cycloheptadienes," *J. Am. Chem. Soc.*, 120(4):3326-3331 (1998); Davies et al., "Enantioselective Synthesis of Functionalized Tropanes by Rhodium(II) Carboxylate-Catalyzed Decomposition of Vinyldiazomethanes in the Presence of Pyrroles," *J. Org. Chem.*, 62(4):1095-1105 (1997); Davies et al., "Effect of Rhodium Carbenoid Structure on Cyclopropanation Chemoselectivity," *Tetrahedron*, 56:4871-4880 (2000); Davies et al., "Enantioselective Synthesis of Fused Cycloheptadienes by a Tandem Intramolecular Cyclopropanation/Cope Rearrangement Sequence," *J. Org. Chem.*, 64(23): 8501-8508 (1999); Davies, "Rhodium-Stabilized Vinylcarbenoid Intermediates in Organic Synthesis," *Current Organic Chemistry*, 2:463-488 (1998); and Davies, "Asymmetric Synthesis Using Rhodium-Stabilized Vinylcarbenoid Intermediates," *Aldrichimica Acta*, 30(4):107-114 (1997), each of which is hereby incorporated by reference.

The above-described reactions exemplify the present invention's usefulness in catalyzing [3+4] annulation reactions in which vinyldiazomethanes are reacted, for example, intermolecularly with a diene by contacting the vinyldiazomethane with a catalyst of the present invention under conditions effective to produce a seven or eight membered ring or ring system. It should be noted that these reactions can also be carried out intramolecularly with a diene moiety contained in the vinyldiazomethane. These methods provide new and useful ways to make compounds (such as the compounds illustrated by Formulae XXXVII and XXXVIII) and to produce seven or eight membered rings and/or seven or eight membered ring systems (e.g., bicyclooctadiene ring systems).

The catalysts of the present invention can also be used to produce a compound having the formula ("Formula XXXIX"):

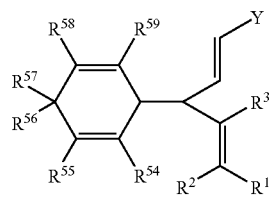

In Formula XXXIX, $R^1$, $R^2$, and $R^3$ are independently selected from H, alkyl, aryl, or vinyl, or $R^1$ and $R^3$, together with the atoms to which they are bonded, form a 5-12 membered ring, such as a cyclohexene ring, or a cyclohexa-1,3-diene ring. Illustratively, the method can be used to prepare compounds in which $R^1$ and $R^3$, together with the atoms to which they are bonded, form an aromatic ring, such as a 3,4-dichlorophenyl ring, in which case the compound produced can have the formula ("Formula XL"):

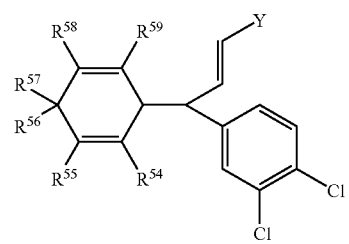

in which Y is an electron withdrawing group, examples of which include moieties having the formulae: —C(O)$R^{77}$, —SO$_2$$R^{77}$, and —P(O)$R^{77}$$R^{77'}$. In these formulae, each of $R^{77}$ and $R^{77'}$ is independently selected from an alkyl group, an aryl group, and an alkoxy group. For example, Y can have the formula CO$_2$$R^{12}$ where $R^{12}$ is an alkyl group or an aryl group.

Each of $R^{54}$, $R^{55}$, $R^{56}$, $R^{57}$, $R^{58}$, and $R^{59}$ is independently selected from the group consisting of H, alkyl, aryl, halogen, and alkoxy.

The method includes providing a 1,3-cyclohexadiene having the formula ("Formula XLI"):

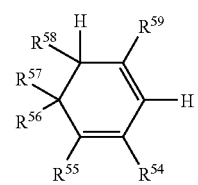

where $R^{54}$, $R^{55}$, $R^{56}$, $R^{57}$, $R^{58}$, and $R^{59}$ are defined as above with regard to Formula XL. The method further includes converting the 1,3-cyclohexadiene with a diazo compound having the formula ("Formula XLII"):

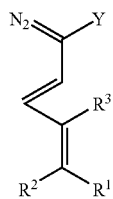

in which Y, $R^1$, $R^2$, and $R^3$ are as defined above.

Illustratively, the reaction can be carried out by mixing the catalyst of the present invention with the 1,3-cyclohexadiene of Formula XLI. In the case where the 1,3-cyclohexadiene of Formula XLI is a liquid (e.g., in the case where the compound of Formula XLI is 1,3-cyclohexadiene), this can be effected without the use of additional solvent. Alternatively, the mixture can be formed using an inert solvent or a solvent which is significantly less reactive towards the diazo compound of Formula XLII than is the compound of Formula XLI. Suitable solvents include alkanes, such as hexanes. The solvent can be dried prior to use using conventional methods; and the reaction vessel can also be dried, such as by flaming or in an oven.

Once the catalyst and compound of Formula XLI are mixed, the compound of Formula XLII is added, for example, with stirring. Addition can be carried out in a single portion, continuously, or batchwise. Slow, dropwise can be effected, for example, by using a syringe pump. The amount of compound of Formula XLII added is generally dependent on the amount of compound of Formula XLI present in the reaction mixture. For example, the mole ratio of compound of Formula XLII to compound of Formula XLI can be from about 1:10 to about 10:1, such as from about 1:8 to about 1:1 and/or from about 1:6 to about 1:4. The addition can be carried out at any suitable temperature from the freezing point to the boiling point of the solvent and/or the compound of Formula XLI. Illustratively, the addition can be carried out from about −50° C. to about 60° C., for example, at about room temperature. In certain embodiments, higher temperatures may favor a reverse Cope rearrangement, in which case, compounds having Formula XXXIX rearrange to form compounds having the formula ("Formula XLIII"):

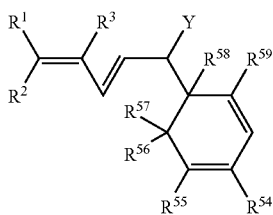

The method is suitable for making compounds having Formula XL which are substantially enantiomerically pure, such as, for example, compounds having the formula ("Formula XLIV"):

such as compounds having the formula ("Formula XLV"):

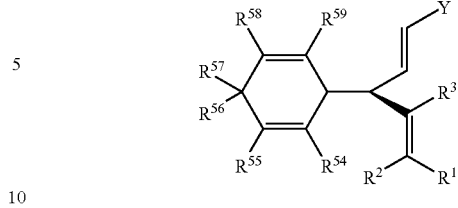

In one embodiment of the present invention, a substantially enantiomerically selective reaction is desired, and a chiral catalyst, such as one having Formula II-A or Formula II-B, is employed.

The cyclohexadiene derivative of Formula XXXIX wherein $R^{57}$ is H can be converted into a compound having the formula ("Formula XLVI"):

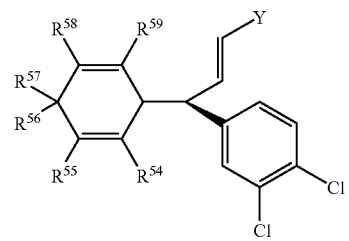

in which $R^1$, $R^2$, $R^3$, $R^{54}$, $R^{55}$, $R^{56}$, $R^{58}$, $R^{59}$, and Y are defined as they were above for the compounds having Formula XXXIX. The conversion can be carried out with hydrogenating and oxidizing agents under conditions effective to form the compound of Formula XLVI. The hydrogenation and oxidation reactions can be carried out simultaneously or sequentially, and, when carried out sequentially, hydrogenation can precede oxidation or oxidation can precede hydrogenation. Suitable hydrogenating agents for use in the present reaction include hydrogen gas in combination with a metal catalyst, such as palladium, (e.g., palladium on carbon). Suitable conditions for carrying out such reactions are described in House, *Modern Synthetic Reactions,* 2nd ed., Menlo Park, Calif.: The Benjamin/Cummings Publishing Company, pp. 1-34 (1972) ("House"), which is hereby incorporated by reference. Suitable oxidizing agents for use in the present reaction include those which are generally known to dehydrogenate 1,4-cyclohexadienyl moieties to phenyl moieties, such as 2,3-dichloro-5,6-dicyano-1,4-benzoquinone ("DDQ") and tetrachlorobenzoquinone (a.k.a., chloranil). Other suitable oxidizing agents and suitable conditions for carrying out such reactions are described, for example, at pages 33-44 of House, which is hereby incorporated by reference.

The above-described method is useful for making compounds having Formula XLVI in which Y is an alkoxycarbonyl group (e.g., in which Y has the formula —COOR$^{12}$ and R$^{12}$ is an alkyl group) and/or in which R$^1$ and R$^3$, together with the atoms to which they are bonded, form an aromatic ring, such as a 3,4-dichlorophenyl ring. In the latter case, the compound of Formula XLVI has the formula ("Formula XLVII"):

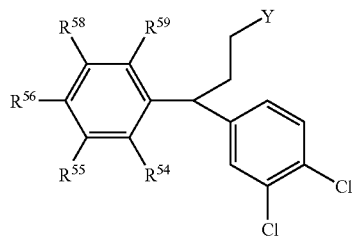

Furthermore, by using a cyclohexadiene having Formula XLIV (e.g., a cyclohexadiene having Formula XLV), substantially enantiomerically pure compounds of Formula XLVI, such as those having the formula ("Formula XLVIII"):

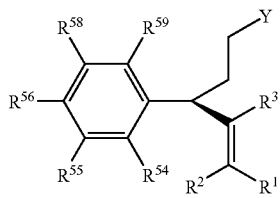

for example, those having the formula ("Formula XLIX"):

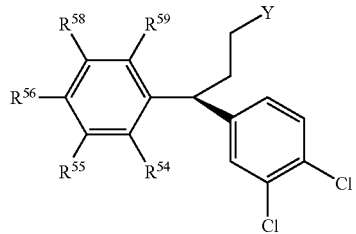

can be prepared.

The compound having Formula XLVI can be used to make a compound having the formula ("Formula L"):

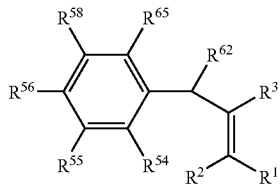

where R$^1$, R$^2$, R$^3$, R$^{54}$, R$^{56}$, and R$^{58}$ are defined as they were with regard to Formula XLVI. R$^{62}$ represents an alkyl moiety, examples of which include methyl, ethyl, or propyl groups, which can optionally be substituted with, for example, aryl groups (optionally containing a heteroatom) (e.g., pyrid-4-ylmethyl) or amino groups (which are meant to include amines that are unsubstituted or mono- or di-substituted with, for example, alkyl or aryl groups) (e.g., 2-(N,N-diisopropylamino)ethyl). Alternatively, R$^{65}$ and R$^{62}$ together represent the atoms necessary to complete a 5-12 membered ring, in which case the compound produced has the formula ("Formula LI"):

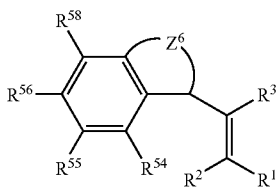

In this formula, Z$^6$ represents, for example, an alkylene group (e.g., a group having the formula —CH$_2$CH$_2$—, —CH$_2$CH$_2$CH$_2$—, —CH(NH$_2$)CH$_2$CH$_2$—, —CH$_2$CH$_2$CH(NH$_2$)—, —CH$_2$NRCH$_2$—, —CH$_2$CH(C$_6$H$_5$)CH$_2$—, etc.). Specific compounds of Formula L which can be made using this method include 1,1-diarylalkanes, such as the pharmaceuticals tolterodine and CDP-840, which respectively have the formulae:

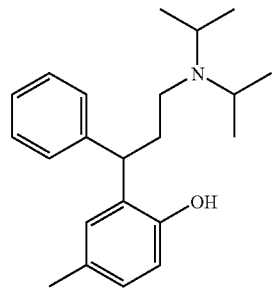

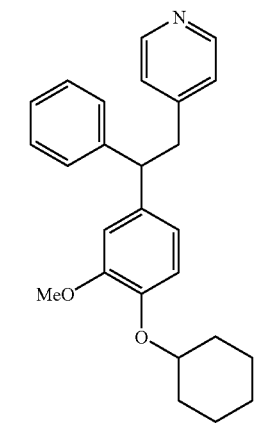

as well as nominfensine and sertraline, which respectively have the formulae:

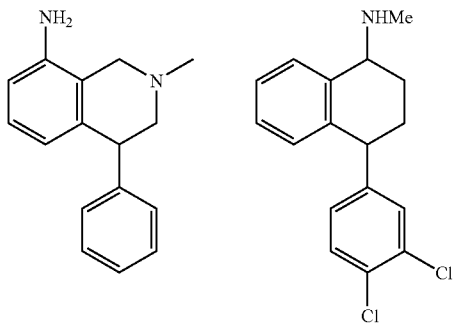

Conditions effective for achieving the conversion of compounds of Formula XLVI to compounds of Formula L depend on the nature of the desired substituents at $R^{62}$ and $R^{65}$. Illustratively, in the case where $R^{62}$ and $R^{65}$ are discreet moieties (i.e., in the case where $R^{62}$ and $R^{65}$ do not combine to form a ring structure), $R^{59}$ can be been chosen so that no further chemistry is required at that position to obtain the desired $R^{65}$ substituent, and the —$CH_2CH_2Y$ moiety can be converted to the desired $R^{62}$ substituent using conventional methods. In the case where $R^{62}$ and $R^{65}$ combine to form a ring, conventional cyclization chemistry can be employed. For example, in the case where $R^{59}$ is H and $R^{62}$ and $R^{65}$ together represent a —$CH_2CH_2CH_2$— moiety, cyclization can be carried out using, for example, a Friedel-Crafts acylation catalyst.

The above method for making compounds having Formula LI is illustrated by the following procedure for making sertraline or sertraline congeners having the formula ("Formula LII"):

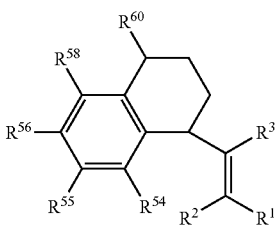

In Formula LII, $R^1$, $R^2$, $R^3$, $R^{54}$, $R^{55}$, $R^{56}$, and $R^{58}$ are defined as they were above with regard to compounds of Formula XLVI. $R^{60}$ is H. $R^{61}$ can represent a substituted or unsubstituted amine, such as an amine having the formula —$NR^{63}R^{64}$, where each of $R^{63}$ and $R^{64}$ is independently selected from hydrogen, an alkyl group, and an aryl group. Illustratively, $R^{61}$ can be a dialkyl amino group (e.g., $N(CH_3)_2$), a monoalkylamino group (e.g., —$NHCH_2CH_3$), or a monoarylamino group (e.g., —$NH(C_6H_5)$), or $R^{61}$ can represent a cyclic amine moiety, such as a piperidinyl group or a morpholino group. Alternately, $R^{60}$ and $R^{61}$, together with the carbon atom to which they are bonded, can represent a carbonyl (i.e., a C=O) moiety.

The method includes providing a cyclohexadiene derivative having Formula XXXIX in which Y is an electron withdrawing group, such as any one of the electron-withdrawing groups described above, and $R^{57}$ and $R^{59}$ are H. Cyclohexadiene derivatives which can be used in this reaction are those described above. Once the cyclohexadiene derivative is provided, it is converted with hydrogenating, oxidizing, and cyclizing agents under conditions effective to form the compound of Formula LII. The hydrogenation and oxidation reactions can be carried out simultaneously or sequentially, and, when carried out sequentially, hydrogenation can precede oxidation or oxidation can precede hydrogenation. Illustratively, both hydrogenation and oxidation can precede cyclization, as in the case where the cyclohexadiene derivative is converted with a hydrogenating agent and an oxidizing agent into a compound of Formula XLVI and where the phenyl derivative is then converted with a cyclizing agent under conditions effective to produce the compound.

Suitable hydrogenating and oxidizing agents and methods for their use are described above. Cyclizing agents suitable for use in the practice of the present invention include acylation catalysts, such as Friedel Crafts acylation catalysts, examples of which include $ClSO_3H$, $AlCl_3$, and other Lewis acids. In the case where Y is an alkoxycarbonyl group, the alkoxy group can be converted to a hydroxy group, prior to treatment with the Friedel Crafts acylation catalyst. This can be done using strong acid, e.g., 6 N HCl, or by any other suitable method. The immediate product of such a cyclization is a tetralone having the formula ("Formula LIII"):

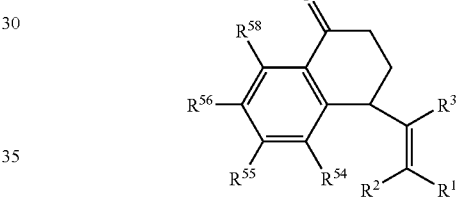

which can be readily converted to compounds having Formula LII by methods known to those skilled in the art, such as the reductive amination method set forth in Corey et al., Tetrahedron Lett., 35:5373-5376 (1994), which is hereby incorporated by reference.

The above-described method is useful for making compounds having Formula LII in which Y is an alkoxycarbonyl group (e.g., in which Y has the formula —$COOR^{12}$ and $R^{12}$ is an alkyl group) and/or in which $R^1$ and $R^3$, together with the atoms to which they are bonded, form an aromatic ring, such as a 3,4-dichlorophenyl ring, in which case the compound of Formula LII can have the formula ("Formula LIV"):

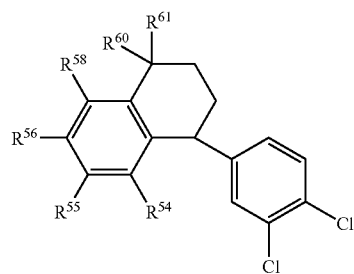

Furthermore, by using a cyclohexadiene having Formula XL (e.g., a cyclohexadiene having Formula XLV), substantially enantiomerically pure compounds of Formula LII, such as those having the formula ("Formula LV"):

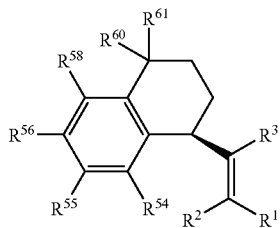

for example, those having the formula ("Formula LVI"):

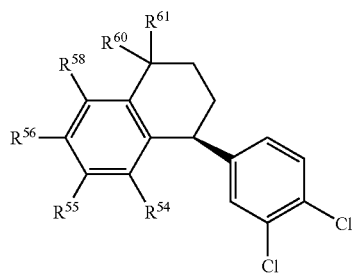

can be prepared.

Further details regarding these reactions as well as further discussion regarding the synthesis of diarylacetates, 4,4-diarylbutanoates, and other ω,ω-diarylalkanoates are set forth, for example, in Davies et al., "Catalytic Asymmetric Synthesis of Diarylacetates and 4,4-Diarylbutanoates. A Formal Asymmetric Synthesis of (+)-Sertraline," *Organic Letters*, 1(2):233-236 (1999), which is hereby incorporated by reference.

Other reactions that can benefit from the use of the catalysts of the present invention in the context of generating rhodium carbenes include those described in: Davies et al., "Effect of Carbenoid Structure on the Reactions of Rhodium-Stabilized Carbenoids with Cycloheptatriene," *Tetrahedron Letters*, 41:2035-2038 (2000), which is hereby incorporated by reference.

As mentioned above, the compounds of the present invention (e.g., those of Formula I) can be used, not only for generating rhodium carbenes, but also for generating rhodium nitrenes, and they can be used in dirhodium catalyzed reactions which proceed via a rhodium nitrene intermediate.

As will be illustrated further in the discussion set forth below and in the Examples section of the present application, the compounds of the present invention can be used in methods for generating rhodium nitrenes; and the present invention, in still another aspect thereof, relates to such methods. More particularly, these methods include contacting a nitrene precursor with a compound according to the present invention, for example, a compound having Formula I under conditions effective to generate the rhodium nitrene. Suitable nitrene precursors include, for example, preformed iodinanes, such as those described in Breslow et al., "Intramolecular Nitrene Carbon-hydrogen Insertions Mediated by Transition-metal Complexes as Nitrogen Analogs of Cytochrome P-450 Reactions," *J. Am. Chem. Soc.*, 105(22): 6728-6729 (1983) ("Breslow I"); and Breslow et al., "Tosylamidation of Cyclohexane by a Cytochrome P-450 Model," *J. Chem. Soc., Chem. Commun.*, (10):1400-1401 (1982) ("Breslow II"), which are hereby incorporated by reference. Other suitable nitrene precursors include iodinanes that are generated in situ, such as those described in Liang et al., "Rhodium(II,II) Dimer as an Efficient Catalyst for Aziridination of Sulfonamides and Amidation of Steroids," *Org. Lett.*, 4(25):4507-4510 (2002) ("Liang I"); Yu et al., "Amidation of Saturated C—H Bonds Catalyzed by Electron-Deficient Ruthenium and Manganese Porphyrins. A Highly Catalytic Nitrogen Atom Transfer Process," *Org. Lett.*, 2(15):2233-2236 (2000) ("Yu"); Au et al., "Ruthenium-Mediated Amidation of Saturated C—H bonds and Crystal Structure of a Bis(tosyl)amidoruthenium(III) Complex of 1,4,7-Trimethyl-1,4,7-triazacyclononane," *Chem. Commun.*, (24):2677-2678 (1998) ("Au I"); Au et al., "Amidation of Unfunctionalized Hydrocarbons Catalyzed by Ruthenium Cyclic Amine or Bipyridine Complexes," *J. Org. Chem.*, 65(23):7858-7864 (2000) ("Au II"); Fiori et al., "Rh-Catalyzed Amination of Ethereal $C^\alpha$—H Bonds: A Versatile Strategy for the Synthesis of Complex Amines" *Angew. Chem., Int. Ed.*, 43(33):4349-4352 (2004) ("Fiori"); Espino et al., "A Rh-Catalyzed C—H Insertion Reaction for the Oxidative Conversion of Carbamates to Oxazolidinones," *Angew. Chem., Int. Ed.*, 40(3):598-600 (2001) ("Espino I"); Espino et al., "Synthesis of 1,3-Difunctionalized Amine Derivatives through Selective C—H Bond Oxidation," *J. Am. Chem. Soc.*, 123(28):6935-6936 (2001) ("Espino II"); Kim et al., "Expanding the Substrate Scope for C—H Amination Reactions: Oxidative Cyclization of Urea and Guanidine Derivatives," *Org. Lett.*, 8(6):1073-1076 (2006) ("Kim"); Espino et al., "Expanding the Scope of C—H Amination through Catalyst Design," *J. Am. Chem. Soc.*, 126(47):15378-15379 (2004) ("Espino III"); Wehn et al., "Stereochemical Models for Rh-Catalyzed Amination Reactions of Chiral Sulfamates,", *Org. Lett.*, 5(25):4823-4826 (2003) ("Wehn"); Hinmann et al., "A Stereoselective Synthesis of (−)-Tetrodotoxin," *J. Am. Chem. Soc.*, 125(38): 11510-11511 (2003) ("Hinmann"); and Fleminget al., "A Synthesis of (+)-Saxitoxin," *J. Am. Chem. Soc.*, 128(12): 3926-3927 (2006) ("Fleminget"), which are hereby incorporated by reference. Still other suitable nitrene precursors include tosyloxycarbamates, such as those described in Lebel et al., "N-Tosyloxycarbamates as a Source of Metal Nitrenes: Rhodium-Catalyzed C—H Insertion and Aziridination Reactions," *J. Am. Chem. Soc.*, 127(41):14198-14199 (2005) ("Lebel"); and Barani et al., "$Cs_2CO_3$ or CaO as promoters of Ethyl N-{[(4-Methylphenyl)sulphonyl]oxy}carbamate in Amination Reactions," *Tetrahedron*, 50(38):11235-11238 (1994) ("Barani"), which are hereby incorporated by reference.

Examples of dirhodium catalyzed reactions which proceed via a rhodium nitrene intermediate include C—H amination reactions and aziridination reactions. Illustratively, the compounds of the present invention can also be used to catalyze C—H amination reactions by contacting a compound comprising a C—H bond with the compound according to the present invention (e.g., a compound of Formula I) under conditions effective to catalyze the C—H amination reaction.

Compounds containing a C—H bond suitable for use as substrates in this reaction include those having the formula $R^{21}$—$CH(R^{22})$—$R^{23}$ where $R^{21}$ represents a alkyl group or an aryl group, where $R^{22}$ represents a alkyl group or an aryl group, and where $R^{22}$ represents a hydrogen atom, an alkyl group, or an aryl group. In certain embodiments, $R^{22}$ is a hydrogen atom. In certain embodiments, $R^{21}$ is an aryl group. In certain embodiments, $R^{23}$ is an alkyl group. Examples of compounds having the formula $R^{21}$—CH($R^{22}$)—$R^{23}$ include those in which $R^{22}$ is a hydrogen atom and in which $R^{21}$ is an aryl group; those in which $R^{22}$ is a hydrogen atom, in which $R^{21}$ is an aryl group, and in which $R^{23}$ is an alkyl group; and/or those having one or more of the following formulae:

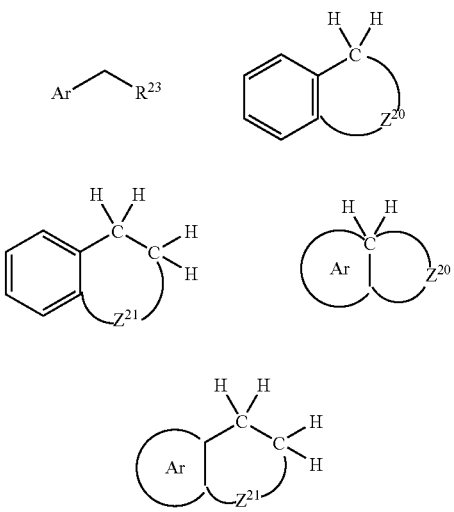

in which $Z^{20}$ and $Z^{21}$ represent atoms needed to complete a substituted or unsubstituted 5-12 membered ring or ring system, and in which Ar represents a substituted or unsubstituted aryl ring or ring system.

As noted above, the subject reaction is carried out under conditions effective to catalyze the C—H amination reaction. This typically involves generating a nitrene precursor, for example, by mixing PhI(OAC)$_2$ with an arylsulfonyl amine (e.g., nosyl amine, tosyl amine, brosyl amine, etc.) in the presence of magnesium oxide, a catalyst of the present invention, and the substrate. Details regarding the generation of nitrene precursors and further details regarding conditions that are effective to catalyze the C—H amination reaction are set forth below in the Examples section of the present application and in the references cited therein.

The above-described method for catalyzing C—H amination reactions provides a useful technique for producing C—N bonds and for the preparation of compounds that contain a C—N bond, and the present invention is directed to methods for preparing such compounds that contain a C—N bond.

Further details regarding the compounds and methods of the present application can be found in Reddy et al., "Dirhodium Tetracarboxylate Derived from Adamantylglycine as a Chiral Catalyst for Carbenoid Reactions," *Organic Letters*, 8(16):3437-3440 (2006), which is hereby incorporated by reference; and in Davies et al., "Dirhodium Tetracarboxylate Derived from Adamantylglycine as a Chiral Catalysts for Enantioselective C—H Aminations," *Organic Letters*, 8(22):5013-5016 (2006), which is hereby incorporated by reference.

The present invention is further illustrated by the following non-limiting examples.

EXAMPLES

Example 1

Optimization of Adamantane C—H Activation and Synthesis of Rh$_2$(S-PTAD)$_4$

This Example 1 illustrates the synthesis of a compound of Formula I, Rh$_2$(S-PTAD)$_4$, which has the following formula:

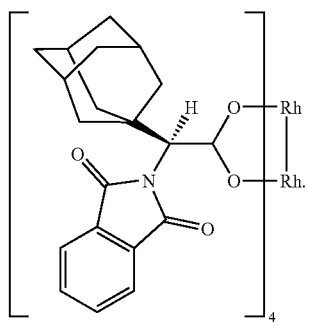

An important step in the synthesis of Rh$_2$(S-PTAD)$_4$ is an intermolecular C—H functionalization of adamantane by means of a metal carbenoid-induced C—H insertion. The Rh$_2$-(S-DOSP)$_4$-catalyzed reactions of donor/acceptor-substituted carbenoids are particularly effective because highly regioselective and enantioselective C—H functionalization can be achieved (Davies et al., "Asymmetric Intermolecular Carbenoid C—H Insertions Catalyzed by Rhodium(II) (S)—N-(p-Dodecylphenyl)sulfonylprolinate," *J. Am. Chem. Soc.*, 119(38):9075-9076 (1997) ("Davies I"); Davies et al., "Catalytic Asymmetric Synthesis of Diarylacetates and 4,4-Diarylbutanoates. A Formal Asymmetric Synthesis of (+)-Sertraline," *Org. Lett.*, 1(2):233-236 (1999) ("Davies II"); Davies et al., "Catalytic Asymmetric Synthesis of Diarylacetates and 4,4-Diarylbutanoates. A Formal Asymmetric Synthesis of (+)-Sertraline," *Org. Lett.*, 1(3):383-386 (1999) ("Davies III"); Davies et al., "Highly Regio-, Diastereo-, and Enantioselective C—H Insertions of Methyl Aryldiazoacetates into Cyclic N-Boc-Protected Amines. Asymmetric Synthesis of Novel C2-Symmetric Amines and threo-Methylphenidate," *J. Am. Chem. Soc.*, 121(27):6509-6510 (1999) ("Davies IV"); Axten et al., "Enantioselective Synthesis of D-threo-Methylphenidate," *J. Am. Chem. Soc.*, 121(27):6511-6512 (1999) ("Axten"); Davies et al., "Effect of Carbenoid Structure on the Reactions of Rhodium-stabilized Carbenoids with Cycloheptatriene," *Tetrahedron Lett.*, 41(13):2035-2038 (2000) ("Davies V"); Muller et al., "Intermolecular Cyclopropanation versus C—H Insertion in RhII-Catalyzed Carbenoid Reactions," *Tetrahedron*, 56(12):1725-1731 (2000) ("Mueller"); Davies et al., "Asymmetric Catalytic C—H Activation Applied to the Synthesis of Syn-Aldol Products," *Org. Lett.*, 2(26):4153-4156 (2000) ("Davies VI"); and Davies et al., "Catalytic Asymmetric C—H Activation of Silyl Enol Ethers as an Equivalent of an Asymmetric Michael Reaction," *J. Am. Chem. Soc.*, 123(9):2070-2071 (2001) ("Davies VII"), which are hereby incorporated by reference). Previous studies have demonstrated that a range of alkanes can be functionalized (Davies et al., "Catalytic Asymmetric C—H Activation of Alkanes and Tetrahydrofuran," *J. Am. Chem. Soc.*, 122(13):3063-3070

(2000) ("Davies VIII"), which is hereby incorporated by reference), and in this work, this reaction is used in the synthesis of adamantylglycine. Experiments were carried out to optimize adamantate C—H activation, and the results of the Rh$_2$(S-DOSP)$_4$-catalyzed reaction of the vinyldiazoacetates 22 with adamantane (1) using hexanes as solvent are summarized in the following Table 1.

TABLE 1

| compound | R | temp ° C. | yield, % | ee, % |
|---|---|---|---|---|
| a | H | 69 | 58 | 91 |
| b | OMe | 69 | 40 | 85 |
| c | Br | 69 | 57 | 95 |
| d | Br | 23 | 10 | 98 |

It is believed that selective C—H functionalization at the tertiary C—H bond occurs because this is electronically favored and is not sterically encumbered (Davies VIII, which is hereby incorporated by reference). Optimization studies were conducted with three vinyldiazoacetates 22a-22c. The p-bromo derivative 22b gave the highest enantioselectivity under refluxing conditions (95% ee), and this could be improved to 98% ee for a room-temperature reaction; however, the yield was greatly decreased. The most practical system was the phenylvinyldiazoacetate 22a because the product was easily purified and enriched by recrystallization. The selectivity of the C—H activation is sufficiently high that the reaction can be carried out in hexanes as solvent. The reaction of 22a has been conducted on a 40-50 g scale, and a single recrystallization enriches the product (S)-23a to >99% ee.

The conversion of 23 to Rh$_2$(S-PTAD)$_4$ was readily achieved using the steps outlined in the following Scheme 1.

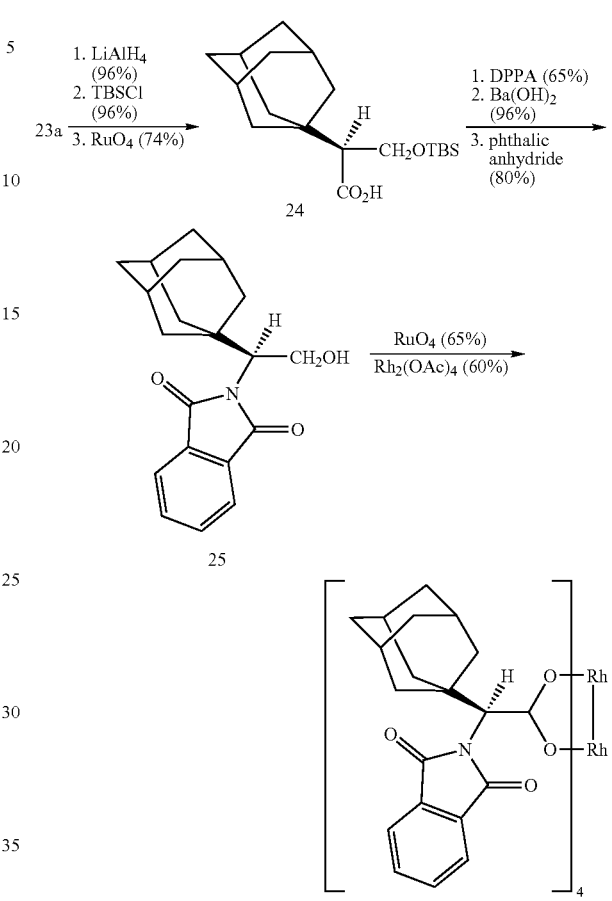

LiAlH$_4$-mediated reduction of the ester 23 followed by protection of the alcohol and oxidative cleavage (Carlsen et al., "A Greatly Improved Procedure for Ruthenium Tetroxide Catalyzed Oxidations of Organic Compounds," *Org. Chem.*, 46(19), 3936-3938 (1981), which is hereby incorporated by reference) of the alkene generated the acid 24. A Curtius rearrangement on the acid 24, followed by conversion of the amine to the phthalimide, generated the protected amino alcohol 25. Oxidation of the alcohol 25 to the acid and then ligand exchange with dirhodium tetraacetate (Callot et al., "Rhodium(II)2,4,6-Triarylbenzoates: Improved Catalysts for Syn Cyclopropanation of z-Olefins," *Tetrahedron*, 41(20), 4495-4501 (1985) ("Callot"), which is hereby incorporated by reference) resulted in the formation of Rh$_2$(S-PTAD)$_4$. A similar sequence beginning with a Rh$_2$(R-DOSP)$_4$-catalyzed C—H activation of adamantane generated Rh$_2$(R-PTAD)$_4$.

Further details regarding the synthesis of Rh$_2$(S-PTAD)$_4$ and other reactions described in this Example 1 are provided in Example 3.

Example 2

Comparison of Rh$_2$(S-PTAD)$_4$ and Other Dirhodium Catalysts in Carbenoid Reactions The first set of experiments compared Rh$_2$(S-PTAD)$_4$ to two standard catalysts, Rh$_2$(S-DOSP)$_4$ and Rh$_2$(S-PTTL)$_4$.

Rh$_2$(S-DOSP)$_4$ is the premier chiral catalyst for the reactions of the donor/acceptor-substituted carbenoids, especially when the acceptor group is a methyl ester (Davies et al., "Catalytic Enantioselective C—H Activation by Means of Metal-Carbenoid-Induced C—H Insertion," *Chem. Rev.*, 103(8):2861-2904 (2003) ("Davies IX"); Davies et al., "Recent Progress in Asymmetric Intermolecular C—H Activation by Rhodium Carbenoid Intermediates," *J. Organomet. Chem.*, 617:47-55 (2001) ("Davies X"); Davies I; Davies II; Davies III; Davies IV; Axten; Davies V; Mueller; Davies VI; and Davies VII, which are hereby incorporated by reference). In a few cases, however, the Rh$_2$(S-DOSP)$_4$-catalyzed reaction is not highly enantioselective and Rh$_2$(S-PTTL)$_4$ results in higher enantioinduction (Davies et al., "Asymmetric Intramolecular C—H Insertions of Aryldiazoacetates," *Org. Lett.*, 3(10), 1475-1477 (2001) ("Davies XI"); Saito et al., "Enantio- and Diastereoselective Synthesis of cis-2-Aryl-3-methoxycarbonyl-2,3-dihydrobenzofurans via the Rh(II)-Catalyzed C—H Insertion Process," *Org. Lett.*, 4(22):3887-3890 (2002) ("Saito"); Davies et al., "Asymmetric Intermolecular C—H Functionalization of Benzyl Silyl Ethers Mediated by Chiral Auxiliary-Based Aryldiazoacetates and Chiral Dirhodium Catalysts," *J. Org. Chem.*, 70(26), 10737-10742 (2005), which are hereby incorporated by reference). One such system is the intramolecular C—H insertion of the aryldiazoacetate 26, which generates the benzodihydrofuran 27, as shown in Table 2 (Davies XI; and Saito, which are hereby incorporated by reference).

TABLE 2

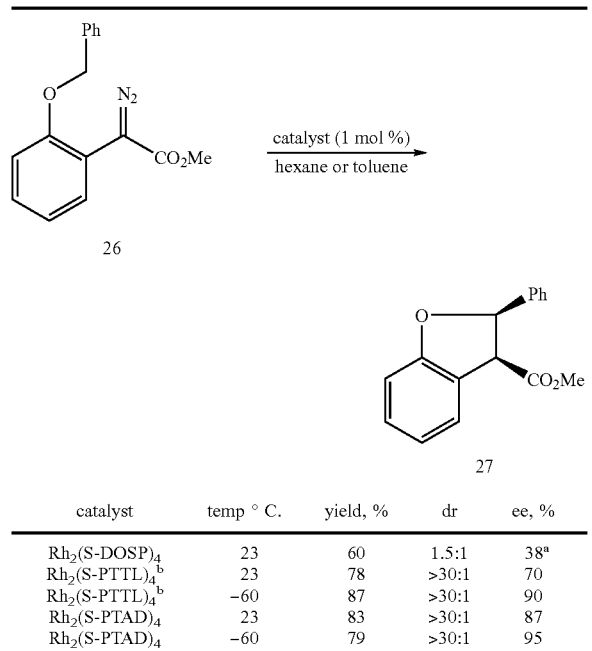

| catalyst | temp ° C. | yield, % | dr | ee, % |
|---|---|---|---|---|
| Rh$_2$(S-DOSP)$_4$ | 23 | 60 | 1.5:1 | 38[a] |
| Rh$_2$(S-PTTL)$_4$[b] | 23 | 78 | >30:1 | 70 |
| Rh$_2$(S-PTTL)$_4$[b] | −60 | 87 | >30:1 | 90 |
| Rh$_2$(S-PTAD)$_4$ | 23 | 83 | >30:1 | 87 |
| Rh$_2$(S-PTAD)$_4$ | −60 | 79 | >30:1 | 95 |

[a]ent-27 is the major enantiomer
[b]Saito, which is hereby incorporated by reference The Rh$_2$(S-PTTL)$_4$-catalyzed reaction (Saito, which is hereby incorporated by reference) of 26 proceeds with much higher but opposite enantioinduction than Rh$_2$(S-DOSP)$_4$ (Davies XI, which is hereby incorporated by reference) but Rh$_2$(S-PTAD)$_4$ outperforms both of the standard catalysts. The Rh$_2$(S-PTAD)$_4$-catalyzed reaction formed 27 in 87% ee at room temperature and 95% ee at −60° C.

A second example is a key step in the synthesis of natural product (−)-ephedradine A, as shown in Table 3.

TABLE 3

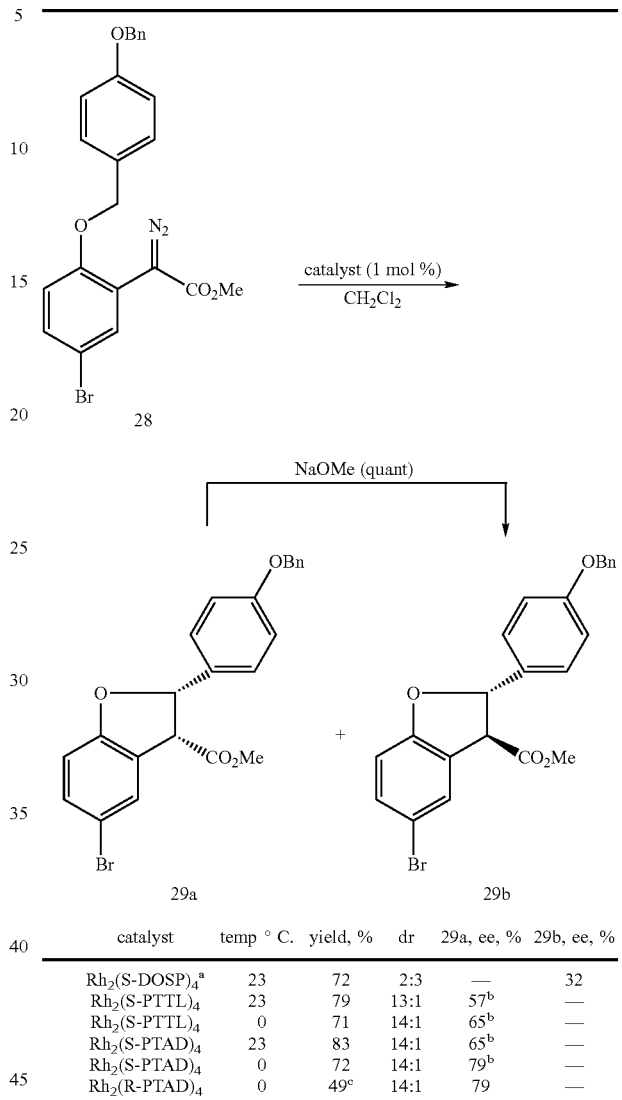

| catalyst | temp ° C. | yield, % | dr | 29a, ee, % | 29b, ee, % |
|---|---|---|---|---|---|
| Rh$_2$(S-DOSP)$_4$[a] | 23 | 72 | 2:3 | — | 32 |
| Rh$_2$(S-PTTL)$_4$ | 23 | 79 | 13:1 | 57[b] | — |
| Rh$_2$(S-PTTL)$_4$ | 0 | 71 | 14:1 | 65[b] | — |
| Rh$_2$(S-PTAD)$_4$ | 23 | 83 | 14:1 | 65[b] | — |
| Rh$_2$(S-PTAD)$_4$ | 0 | 72 | 14:1 | 79[b] | — |
| Rh$_2$(R-PTAD)$_4$ | 0 | 49[c] | 14:1 | 79 | — |

[a]Davies VIII, which is hereby incorporated by reference.
[b]ent-29a is the major enantiomer.
[c]Poor isolated yield was obtained in the reaction conducted on a very small scale.

In the published synthesis, the Rh$_2$(S-DOSP)$_4$-catalyzed reaction of 28 generated 29a and 29b with poor diastereoselectivity (2:3 dr) and enantioselectivity (32% ee) (Kurosawa et al., "An Efficient Synthesis of Optically Active trans-2-Aryl-2,3-dihydrobenzofuran-3-carboxylic Acid Esters via C—H Insertion Reaction," *Synlett*, (7):1028-1030 (2003) ("Kurosawa I"), which is hereby incorporated by reference. Reasonable results were obtained only when a combination of Rh$_2$(S-DOSP)$_4$ and a chiral auxiliary was used (Kurosawa I; and Kurosawa et al., "Stereocontrolled Total Synthesis of (−)-Ephedradine A (Orantine)," *J. Am. Chem. Soc.*, 125(27):8112-8113 (2003) ("Kurosawa II"), which are hereby incorporated by reference). This gave rise to the desired trans stereoisomer, with an asymmetric induction of 86% de (Kurosawa I; and Kurosawa II, which are hereby incorporated by reference). The Rh$_2$(S-PTTL)$_4$- or Rh$_2$(S-PTAD)$_4$-catalyzed reactions described in this example were much more stereoselective than the Rh₂(S-DOSP)₄-catalyzed reaction. Under the optimized conditions, the Rh₂(R-PTAD)₄-catalyzed reaction of 28 generated preferentially the cis isomer 29a in a 14:1 dr with 79% ee, without requiring the use of a chiral auxiliary. The cis isomer 29a can be readily equilibrated to the desired trans isomer 29b on treatment with sodium methoxide following Hashimoto's conditions (Saito, which is hereby incorporated by reference).

Even though Rh₂(S-DOSP)₄ gives excellent enantioinduction with a range of donor substituents in the donor/acceptor-substituted carbenoids (Davies IX; and Davies X, which are hereby incorporated by reference), altering the acceptor group can have a profound effect on the level of enantioinduction (Davies et al., "Asymmetric Cyclopropanations by Rhodium(II) N-(Arylsulfonyl)prolinate Catalyzed Decomposition of Vinyldiazomethanes in the Presence of Alkenes. Practical Enantioselective Synthesis of the Four Stereoisomers of 2-Phenylcyclopropan-1-amino Acid," *J. Am. Chem. Soc.*, 118(29):6897-6907 (1996), which is hereby incorporated by reference). This is clearly seen in the asymmetric cyclopropanation of the diazophosphonate 30, as shown in Table 4.

TABLE 4

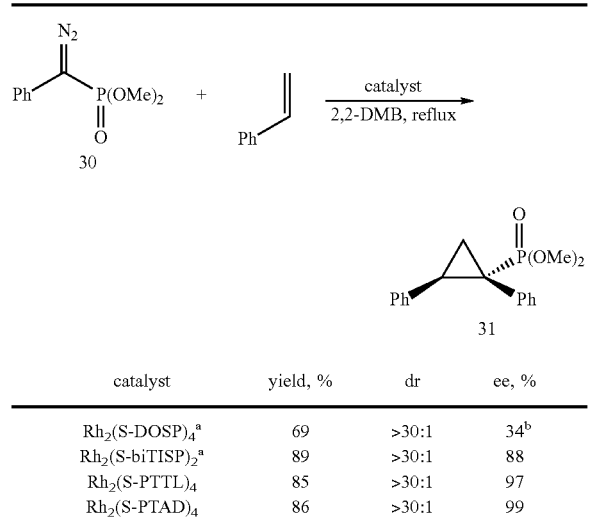

| catalyst | yield, % | dr | ee, % |
| --- | --- | --- | --- |
| Rh₂(S-DOSP)₄[a] | 69 | >30:1 | 34[b] |
| Rh₂(S-biTISP)₂[a] | 89 | >30:1 | 88 |
| Rh₂(S-PTTL)₄ | 85 | >30:1 | 97 |
| Rh₂(S-PTAD)₄ | 86 | >30:1 | 99 |

[a]Davies XII, which is hereby incorporated by reference.
[b]ent-31 is the major enantiomer.

The Rh₂(S-DOSP)₄-catalyzed cyclopropanation of styrene results in the formation of 31 in 34% ee (Davies et al., "Enantioselective Synthesis of Cyclopropylphosphonates Containing Quaternary Stereocenters Using a D2-Symmetric Chiral Catalyst Rh₂(S-biTISP)₂," *Org. Lett.*, 6 (13):2117-2120 (1994) ("Davies XII"), which is hereby incorporated by reference). The bridged prolinate catalyst Rh₂(S-biTISP)₂ results in 88% ee (Davies XII, which is hereby incorporated by reference). As shown in Table 4, Rh₂(S-PTTL)₄ or Rh₂(S-PTAD)₄ is far superior, with Rh₂(S-PTAD)₄ resulting in the highest enantioselectivity (99% ee).

A similar enhancement in enantioselectivity can be achieved for intermolecular C—H activation of 1,4-cyclohexadiene by diazophosphonate 30, as illustrated in Table 5).

TABLE 5

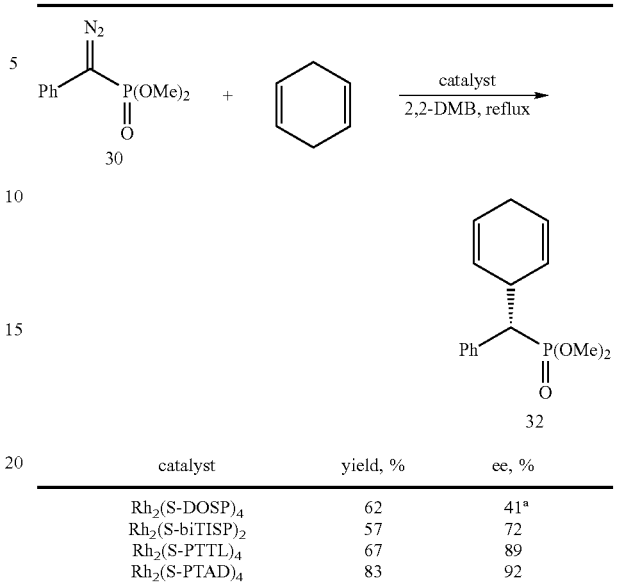

| catalyst | yield, % | ee, % |
| --- | --- | --- |
| Rh₂(S-DOSP)₄ | 62 | 41[a] |
| Rh₂(S-biTISP)₂ | 57 | 72 |
| Rh₂(S-PTTL)₄ | 67 | 89 |
| Rh₂(S-PTAD)₄ | 83 | 92 |

[a]Opposite enantiomer preferentially formed.

The Rh₂(S-DOSP)₄-catalyzed reaction generated the C—H activation product 32 in 41% ee, whereas, with Rh₂(S-PTAD)₄, the opposite enantiomer was preferentially formed (92% ee). The absolute configuration of 32 has not been determined, but if the sense of asymmetric induction follows the trend of aryldiazoacetate C—H insertion (Davies et al., "Catalytic Asymmetric Synthesis of Diarylacetates and 4,4-Diarylbutanoates. A Formal Asymmetric Synthesis of (+)-Sertraline," *Org. Lett.*, 1(2):233-236 (1999), which is hereby incorporated by reference), the predicted configuration of 32 for the Rh₂(S-DOSP)₄-catalyzed reaction would be (R) and for the other catalysts it would be (S).

In summary, these studies demonstrate that the phthalimido catalysts Rh₂(S-PTTL)₄ and Rh₂(S-PTAD)₄ are promising backup catalysts for Rh₂(S-DOSP)₄. Even though Rh₂(S-DOSP)₄ has been very effective with a wide variety of substrates, it does have certain substrate limitations, especially when the acceptor group is not a methyl ester. Both Rh₂(S-PTTL) 4 and Rh₂(S-PTAD)₄ can perform extremely well in these problem systems, with the adamantyl catalyst Rh₂(S-PTAD)₄ generally giving higher enantioselectivity than the tert-butyl catalyst, Rh₂(S-PTTL)₄.

Further details regarding the syntheses referred to in this Example 2 are provided in Example 3.

Example 3

Experimental Details For Optimization of Adamantane C—H Activation, Synthesis of Rh₂(S-PTAD)₄, and Studies of Rh₂(S-PTAD)₄ and Other Dirhodium Catalysts in Carbenoid Reactions This Example 3 provides some additional details with regard to the experiments described in Examples 1 and 2.

¹H NMR spectra were run at either 400 or 500 MHz, and ¹³C NMR at either 75 or 125 MHz with the sample solvent being CDCl₃ unless otherwise noted. Mass spectral determinations were carried out in GC-MS (EI), LC-MS (ESI) or by Instrument Center, Department of Chemistry, University at Buffalo. IR spectra were obtained using a Perkin Elmer 1760X FT-IR. Optical rotations were measured using a Jasco DIP-370 digital polarimeter. Elemental analyses were performed by Atlantic Microlabs Inc., Norcross Ga. Enantiomeric excess was determined by HPLC (UV detection at 254 nm). Analytical TLC was performed on 0.25 mm E. Merck silica gel (60F-254) plates using UV light.

Glassware was dried in oven overnight then flame or heat-gun dried prior to use. Reactions were conducted under argon atmosphere. Column chromatography was carried out on Merck silica gel 60 (230-400 mesh). Solvents THF, $Et_2O$, $CH_3CN$, $CH_2Cl_2$, and toluene were dried by solvent purifier. Diazoacetates 22a, 22b, 22c were prepared as described in Davies et al., "Direct Synthesis of Methyl 2-Diazo-4-aryl-3-butenoates and Their Application to the Enantioselective Synthesis of 4-Aryl-4-(1-naphthyl)-2-butenoates," *Tetrahedron: Asymmetry*, 17(4):665-673 (2006), which is hereby incorporated by reference; diazoacetate 26 was prepared as described in Saito, which is hereby incorporated by reference; diazoacetate 28 was prepared as described in Kurosawa II, which is hereby incorporated by reference; and diazoacetate 30 was prepared as described in Regitz et al., "7-Phosphono-z-Aryl-Norcaradiene," *Chem. Ber.*, 105:3357-3381 (1972), which is hereby incorporated by reference.

(S,E)-Methyl 2-adamantyl-4-phenylbut-3-enoate (23a) was prepared as follows. To a flame-dried round bottom flask under argon and charged with a magnetic stir bar was added adamantane (141.1 g, 1.03 mol, 5 eq), $Rh_2(S\text{-}DOSP)_4$ (2.02 g, 0.5 mol %) and dissolved in 700 mL of degassed hexanes. This solution was heated to reflux. A solution of diazoacetate 22a (42 g, 0.21 mol) in degassed hexanes (200 mL) was then added to this refluxing solution via cannula over 45 min. Once the addition was completed, the mixture was allowed to reflux for 2 h. After cooling, the mixture was stirred for 2 h at 23° C. The solvent was then removed in vacuo, and excess adamantane was removed by Kugelrohr distillation. The residue was then purified by flash chromatography (5:1 hexanes/ethyl acetate) to give the product (39.6 g, 59% yield, 91% ee) as a white solid. The product was recrystallized from methanol (740 mL) to give 23a (36.4 g, 92% recovery, >99% ee) as a white solid. mp=115-117° C.; $R_f$=0.5 (4:1 hexanes/ethyl acetate); $[\alpha]_D^{25}$ -74.9° (c 1.0, $CHCl_3$); FTIR (neat) 3023, 2924, 2850, 1725, 1598, 1497, 1454, 1346, 1317, 1260, 1149, 1190, 999, 754, 692 $cm^{-1}$; $^1H$ NMR (500 MHz, $CDCl_3$) δ 7.38 (d, J=7.5 Hz, 2H), 7.30 (t, J=7.5 Hz, 2H), 7.21 (t, J=7.5 Hz, 1H), 6.35 (m, 2H), 3.67 (s, 3H), 2.79 (d, J=8.5 Hz, 1H), 1.97 (s, 3H), 1.77-1.51 (m, 12H); $^{13}C$ NMR (125 MHz, $CDCl_3$) δ 173.0, 136.8, 133.4, 128.5, 127.4, 126.3, 124.8, 61.4, 51.2, 40.1, 36.7, 36.3, 28.6. Anal. Calcd for $C_{21}H_{26}O_2$: C, 81.25, H, 8.44. Found: C, 81.34, H, 8.32. HPLC analysis (Chiralpak AD-RH, 1% 2-propanol in hexanes, 0.5 mL/min, 254 nm; $t_R$(major)=8.8 min; $t_R$(minor)=10.5 min). 91% ee before recrystallization and >99% ee after one recrystallization.

(S,E)-Methyl 2-adamantyl-4-(4-methoxyphenyl)-but-3-enoate (3b) was prepared as follows. To a flame-dried round bottom flask under argon and charged with a magnetic stir bar was added adamantane (500 mg, 3.67 mmol, 5 eq), $Rh_2(S\text{-}DOSP)_4$ (13.7 mg, 0.5 mol %) and dissolved in degassed hexanes (15 mL). This solution was heated to reflux. A solution of diazoacetate 22b (170 mg, 0.73 mmol) in degassed hexanes (6 mL) was then added to this refluxing solution via syringe pump over 45 min. Once the addition was completed, the mixture was allowed to reflux for 2 h. After cooling, the mixture was stirred for 2 h at 23° C., the solvent was then removed in vacuo, and excess adamantane was removed by Kugelrohr distillation. The residue was then purified by flash chromatography (5:1 hexanes/ethyl acetate) to give product 23b (99 mg, 40% yield, 89% ee) as a white solid. $R_f$=0.38 (9:1 pentane:ether); $[\alpha]_D^{25}$ -66.2° (c 0.54, $CHCl_3$); FTIR (neat) 2910, 2848, 1722, 1606, 1510, 1250, 1152, 1031, 977, 826, 810 $cm^{-1}$; $^1H$ NMR (500 MHz, $CDCl_3$) δ 7.32 (d, J=8.5 Hz, 2H), 6.84 (d, J=8.5 Hz, 2H), 6.31 (d, J=16 Hz, 1H), 6.18 (dd, J=16, 10 Hz, 1H), 3.80 (s, 3H), 3.67 (s, 3H), 2.76 (d, J=10 Hz, 1H), 1.97 (bs, 3H), 1.76-1.49 (m, 12H); $^{13}C$ NMR (125 MHz, $CDCl_3$) δ 173.3, 159.1, 132.8, 129.8, 127.5, 122.5, 113.9, 61.5, 55.3, 51.2, 40.1, 36.8, 36.3, 28.6. HRMS (ESI) m/z Calcd for $[C_{22}H_{28}O_3+Na^+]$: 363.1931. Found: 363.1932. HPLC analysis 89% ee (Chiralpak AD-RH, 1% 2-propanol in hexanes, 0.5 mL/min, 254 nm; $t_R$=25.0 min, major; $t_R$=30.4 min, minor).

(S,E)-Methyl 2-adamantyl-4-(4-bromophenyl)but-3-enoate (23c) was prepared as follows. To a flame-dried round bottom flask under argon and charged with a magnetic stir bar was added adamantane (500 mg, 3.67 mmol, 5 eq), $Rh_2(S\text{-}DOSP)_4$ (13.7 mg, 0.5 mol %) and dissolved in degassed hexanes (15 mL). This solution was heated to reflux. A solution of diazoacetate 22c (206 mg, 0.73 mmol) in degassed hexanes (6 mL) was then added to this refluxing solution via syringe pump over 45 min. Once the addition was completed, the mixture was allowed to reflux for 2 h. After cooling, the mixture was stirred for 2 h at 23° C. The solvent was then removed in vacuo, and excess adamantane was removed by Kugelrohr distillation. The residue was then purified by flash chromatography (9:1 pentane/ether) to give the 23c (160 mg, 57% yield, 95% ee) as a white solid. $R_f$=0.37 (15:1 pentane/ether); $[\alpha]_D^{25}$ -66.1° (c 0.85, $CHCl_3$); FTIR (neat) 2906, 2847, 1722, 1487, 1446, 1153 $cm^{-1}$; $^1H$ NMR (500 MHz, $CDCl_3$) δ 7.43 (d, J=8.5 Hz, 2H), 7.24 (d, J=8.5 Hz, 2H), 6.36-6.28 (m, 2H), 3.68 (s, 3H), 2.78 (d, J=7.5 Hz, 1H), 2.0 (s, 3H), 1.74-1.49 (m, 12H); $^{13}C$ NMR (125 MHz, $CDCl_3$) δ 172.9, 135.8, 132.2, 131.6, 127.9, 125.8, 123.8, 61.4, 51.3, 40.1, 36.8, 36.4, 28.6. Anal. Calcd for $C_{21}H_{25}BrO_2$: C, 64.78, H, 6.47. Found C, 64.77, H, 6.57. HPLC analysis 95% ee (Chiralpak AD-H, 1% $^iPrOH$/hexanes, 0.5 mL/min, 254 nm, $t_R$=21.2 min, major; $t_R$=27.6 min, minor).

(S,E)-2-Adamantyl-4-phenylbut-3-en-1-ol, having the following formula:

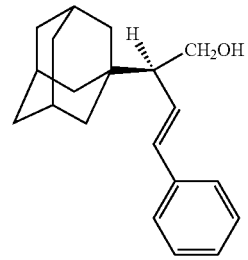

was prepared as follows. (S,E)-Methyl 2-adamantyl-4-phenylbut-3-enoate (23a) (20 g, 0.65 mol) was dissolved in THF (300 mL) under argon, and the solution was cooled to 0° C. To this solution at 0° C., 1.0 M LAH in THF (0.325 mL, 0.5 eq) was added drop wise, and the mixture was allowed to stir at 0° C. for 1 h and then gradually warmed up and stirred for 5 h at 23° C. Then the reaction was quenched by the addition of water at 0° C., and the mixture was extracted by ether and dried over $MgSO_4$. The solvent was removed in vacuo, and the crude material was purified by flash column chromatography on silica gel (10:1 hexanes/ethyl acetate) to give the product (18.3 g, 96% yield) as a white solid. mp=125-127° C. $R_f$=0.35 (10:1 hexanes/ethyl acetate); $[\alpha]_D^{25}$ −34.3° (c 1.0, CHCl$_3$); FTIR (neat) 3279, 2900, 2875, 1449, 1044, 1023, 964 cm$^{-1}$; $^1$H NMR (500 MHz, CDCl$_3$) δ 7.39 (d, J=7.5 Hz, 2H), 7.32 (t, J=7.5 Hz, 2H), 7.23 (m, 1H), 6.47 (d, J=15.5, 1H), 6.14 (dd, J=15.5, 10.5 Hz, 1H), 3.87 (dd, J=10.5, 3.5 Hz, 1H), 3.53 (t, J=10 Hz, 1H), 1.97 (m, 4H), 1.77-1.50 (m, 12H); $^{13}$C NMR (125 MHz, CDCl$_3$) δ 136.9, 134.3, 128.6, 128.5, 127.4, 126.2, 60.9, 57.9, 40.7, 37.1, 34.7, 28.6. HRMS (EI) m/z Calcd for [C$_{20}$H$_{26}$O]:282.1978. Found: 282.1973.

((S,E)-2-Adamantyl-4-phenylbut-3-enyloxy)(tert-butyl) dimethylsilane, having the following formula:

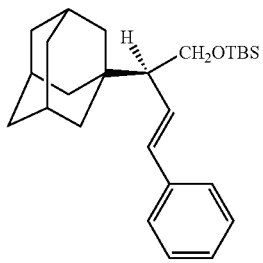

was prepared as follows. (S,E)-2-Adamantyl-4-phenylbut-3-en-1-ol (17.0 g, 60.2 mmol) was dissolved in DCM (200 mL), and then imidazole (4.51 g, 66.2 mmol, 1.1 eq) and DMAP (1.15 g, 9.0 mmol, 0.15 eq) were added. The mixture was cooled to 0° C. under argon, and then TBSCl (9.98 g, 66.2 mmol, 1.1 eq) was added, and the solution was gradually warmed up to 23° C. and stirred for 12 h. The reaction mixture was washed with water and brine and dried over MgSO$_4$. The solvent was removed in vacuo, and the crude product was purified by flash column chromatography on silica gel to give the product (5:1 hexanes/ethyl acetate) (23.1 g, 96% yield) as a white solid. mp=47-49° C. $R_f$=0.35 (5:1 hexanes/ethyl acetate); $[\alpha]_D^{25}$ −42.3° (c 0.97, CHCl$_3$); FTIR (neat) 3276, 2899, 2845, 1598, 1454, 1254, 1119, 1103, 960, 837, 774, 746, 692 cm$^{-1}$; $^1$H NMR (500 MHz, CDCl$_3$): δ 7.36 (d, J=7.0 Hz, 2H), 7.30 (t, J=7.5 Hz, 2H), 7.20 (d, J=7.5 Hz 1H), 6.34 (d, J=15.5 Hz, 1H), 6.17 (dd, J=15.5, 10.5 Hz, 1H), 3.87 (dd, J=3.5, 10.5 Hz, 1H), 3.66 (t, J=10.3 Hz, 1H), 1.97 (bs, 4H), 1.77-1.505 (m, 12H), 0.87 (s, 9H), 0.05 (s, 6H); $^{13}$C NMR (125 MHz, CDCl$_3$): δ 138.1, 132.1, 130.2, 128.4, 126.4, 126.0, 62.5, 56.9, 40.8, 37.2, 34.9, 28.8, 25.9, 18.3, −5.2. HRMS (EI) m/z Calcd for [C$_{25}$H$_{37}$OSi]: [M-CH$_3$]$^+$381.2608, Found: 381.2617.

(S)-2-Adamantan-1-yl-3-(tert-butyl-dimethyl-silanyloxy)-propionic acid (24) was prepared as follows. ((S,E)-2-Adamantyl-4-phenylbut-3-enyloxy)(tert-butyl)dimethylsilane was prepared by the modified procedure of Sharpless and coworkers (Carlsen et al., "A Greatly Improved Procedure for Ruthenium Tetroxide Catalyzed Oxidations of Organic Compounds," *J. Org. Chem.*, 46(19):3936-3938 (1981), which is hereby incorporated by reference). (2-Adamantan-1-yl-4-phenylbut-3-enyloxy)-tert-butyl-dimethylsilane (15.0 g, 37.8 mmol) was dissolved in acetonitrile (220 mL) and ethyl acetate (220 mL), and to this vigorously stirring solution was added a solution of NaIO$_4$ (33.1 g, 0.15 mol, 4.1 eq) in water (330 mL), and the mixture was stirred for 10 min. To this heterogeneous mixture was added RuCl$_3$.H$_2$O (0.19 g, 2.2 mol %), and the mixture was stirred vigorously for 12 h. The reaction mixture was diluted with DCM and filtered through celite. The solution was washed with sodium bicarbonate and dried over MgSO$_4$ and concentrated. Then the slurry was dissolved in ether and passed through a pad of celite and charcoal to remove ruthenium species. The solute was concentrated, and the product was recrystallized from hexanes to give the product (24) (9.15 g, 71% yield) as a white solid. mp=188-190° C. $[\alpha]_D^{25}$ −16.4° (c 1.0, CHCl$_3$) FTIR (neat) 3420, 2927, 2904, 2851, 1706, 1454, 1256, 1102, 837, 776 cm$^{-1}$; $^1$H NMR (500 MHz, CDCl$_3$) δ 3.94 (dd, J=10.0 Hz, 1H), 3.82 (dd, J=10.0, 4.0 Hz, 1H), 2.32 (dd, J=10.0, 4.0 Hz, 1H) 1.97 (s, 3H), 1.78-1.53 (m, 12H), 0.87 (s, 9H), 0.05 (s, 6H); $^{13}$C NMR (125 MHz, CDCl$_3$) δ 178.8, 60.5, 59.8, 40.4, 36.8, 33.9, 28.5, 25.8, 18.2, −5.5. HRMS (EI) Calcd. for [M$^+$-$^t$Bu], C$_{15}$H$_{25}$O$_3$Si: 281.1573. Found: 281.1565.

(S)-4-Adamantyloxazolidin-2-one, having the following formula:

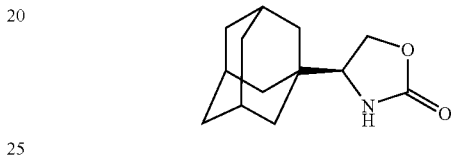

was prepared as follows. To the mixture of 2-adamantan-1-yl-3-(tert-butyl-dimethyl-silanyloxy)-propionic acid (9.2 g, 27 mmol) in toluene (250 mL) was added freshly distilled Et$_3$N (4.18 mL, 40 mmol, 1.1 eq), and the mixture was stirred under argon. It was then charged with DPPA (8.1 g, 29 mmol, 1.08 eq) and refluxed for 2 h. The reaction mixture was cooled down to room temperature and was treated with TFA (7.5 g, 65.4 mmol, 2.5 eq) and refluxed for 12 h. The solvent was removed in vacuo, and the crude product was dissolved in DCM, washed with sodium bicarbonate and brine, and then dried over MgSO$_4$. The solvent was removed in vacuo, and the crude product was purified by flash column chromatography on silica gel (2:1 ethyl acetate/hexanes) to give the product (3.8 g, 63% yield) as a white solid. mp=140-142° C.; $R_f$=0.3 (2:1 ethyl acetate/hexanes) {KMnO$_4$Stain}; $[\alpha]_D^{25}$ −15.7 (c 0.79, CHCl$_3$), lit. $[\alpha]_D^{25}$ for (R)-4-adamantyloxazolidin-2-one (Takacs et al., "Preparation of Chiral Oxazolidin-2-ones and Vicinal Amino Alcohols," *J. Org. Chem.*, 63(8):2742-2748 (1998), which is hereby incorporated by reference): +8.1 (c 0.78, CHCl$_3$); FTIR (neat) 3297, 2901, 2848, 1728, 1416, 1240 cm$^{-1}$; $^1$H NMR (500 MHz, CDCl$_3$) δ 5.62 (bs, 1H), 4.30 (d, J=7.5 Hz, 2H), 3.40 (t, J=7.2 Hz, 1H), 2.03 (s, 3H), 1.77-1.51 (m, 12H); $^{13}$C NMR (125 MHz, CDCl$_3$) δ 160.3, 65.1, 61.6, 37.3, 36.7, 34.9, 27.7. Anal. Calcd for C$_{13}$H$_{19}$NO$_2$: C, 70.56, H, 8.65. Found: C, 70.49, H, 8.56.

(S)-2-Amino-2-adamantylethanol, having the following formula:

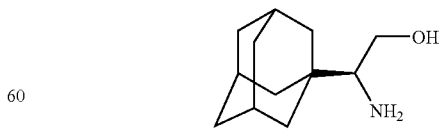

was prepared as follows. (S)-4-Adamantyloxazolidin-2-one (3.2 g, 14.42 mmol), was dissolved in dioxane (95 mL) and water (48 mL), and to it Ba(OH)$_2$.8H$_2$O (22.81 g, 72.3 mmol, 5 eq) was added, and the mixture was refluxed for 12 h. The reaction mixture was filtered to remove barium species and then extracted with DCM and dried over $MgSO_4$. The solvent was removed in vacuo to give the product (2.7 g, 95% yield) as a white solid. mp=137-139° C.; $[\alpha]_D^{25}$ −2.67 (c 0.29, MeOH); FTIR (neat) 3341, 3052, 2900, 2849, 1585, 1449, 1265 cm$^{-1}$; $^1$H NMR (500 MHz, $CDCl_3$) δ3.69 (dd, J=10.0, 4.0 Hz, 1H), 3.24 (t, J=10.0 Hz, 1H), 2.32 (dd, J=10.0, 4.0 Hz, 1H), 2.03 (s, 3H), 1.77-1.50 (m, 12H); $^{13}$C NMR (125 MHz, $CDCl_3$) δ 61.9, 61.1, 38.5, 37.0, 34.9, 28.2. HRMS (EI) m/z Calcd for [$C_{12}H_{21}NO$]: 195.1696, found 195.1703.

2-((S)-1-Adamantyl-2-hydroxyethyl)isoindoline-1,3-dione (25) was prepared as follows. To the mixture of (S)-2-Amino-2-adamantylethanol (1.0 g, 5.12 mmol, 1.0 eq) in DMF (6 mL) was added phthalic anhydride (0.76 g, 5.12 mmol, 1.0 eq) and stirred for 10 min, and the mixture was heated at 140° C. for 12 h. After cooling, the reaction mixture was poured into water, and the product precipitated out as a white solid. The crystals were filtered and vacuum dried to give the product (25) (1.32 g, 80% yield) as a white solid. $R_f$=0.3 (3:2 hexane/EtOAc); $[\alpha]_D^{25}$ 8.10 (c 2.47, $CHCl_3$); IR (neat) 3341, 3153, 2848, 2242 cm$^{-1}$; $^1$H NMR ($CDCl_3$, 500 MHz); δ 7.82 (dd, J=8.5, 5.0 Hz, 2H), 7.57 (d, J=3.5 Hz, 2H), 4.52 (t, J=11.0 Hz, 1H), 3.93 (dd, J=20.0, 9.5 Hz, 2H), 2.01-1.52 (m, 15H); $^{13}$C NMR (125 MHz, $CDCl_3$): δ 170.3, 134.0, 131.9, 123.4, 63.3, 58.8, 40.1, 37.5, 36.7, 28.3. HRMS (EI) m/z Calcd for $C_{20}H_{23}NO_3$: 325.1678, found: 325.1702.

(S)-2-Adamantyl-2-(1,3-dioxoisoindolin-2-yl)acetic acid, having the following formula:

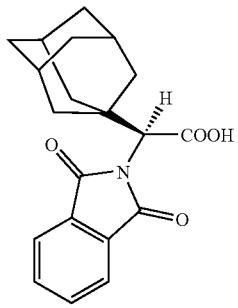

was prepared as follows. To a mixture of 2-((S)-1-adamantyl-2-hydroxyethyl)isoindoline-1,3-dione (25) (0.72 g, 2.2 mmol) in 34 mL of (1:1 EtOAc/$CH_3CN$), was added $NaIO_4$ (1.92 g, 9.0 mmol, 4.1 eq) in water (25 mL) and stirred at 23° C. for 10 min. Then was added $RuCl_3 \cdot H_2O$ (0.01 g, 2.2 mol %), and resulting mixture was stirred vigorously for 12 h. The mixture was diluted with DCM and water and filtered through a pad of celite and charcoal. The filtrate was extracted with DCM and dried over anhydrous $MgSO_4$, and the solvent was removed in vacuo to give the product (0.490 g, 65% yield) as a white solid. $[\alpha]_D^{25}$ −2.6° (c 0.45, $CHCl_3$); IR (neat): 2906, 2850, 1775, 1718, 1385 cm$^{-1}$. $^1$H NMR ($CDCl_3$, 500 MHz): δ 7.85 (dd, J=8.5, 5.0 Hz, 2H), 7.59 (d, J=8.5 Hz, 2H), 4.60 (s, 1H), 2.01-1.65 (m, 15H); $^{13}$C NMR (125 MHz, $CDCl_3$): δ 171.5, 171.4, 134.3, 131.5, 123.7, 61.1, 39.3, 37.8, 36.5, 28.4. HRMS (EI) m/z Calcd for $C_{20}H_{21}NO_4$: 339.1471, found: 339.1457.

$Rh_2$(S-PTAD)$_4$ was prepared using the following procedure, which is similar to that reported in Callot, which is hereby incorporated by reference. Adamantan-1-yl-(1,3-dioxo-1,3-dihydro-isoindol-2-yl)-acetic acid (0.64 g, 1.88 mmol, 6 eq) and $Rh_2(OAc)_4$ (0.14 g, 0.32 mmol) were dissolved in dry chlorobenzene (12 mL) in a stoppered flask under argon and stirred at 23° C. for 30 min. Then the mixture was heated up to 150° C. and distilled out the acetic acid as an azeotrope with chlorobenzene for 3 h (chlorobenzene was added to the flask in between). The mixture was cooled down to 23° C., and the solvent was removed in vacuo. The residue was subjected to flash chromatography (silica, 1.5:1 hexanes/EtOAc-1:1 hexanes/EtOAc) to give the catalyst $Rh_2$(S-PTAD)$_4$ (0.31 g, 60%) as a bright green solid. $R_f$=0.3 (1:1 hexanes:EtOAc); $[\alpha]_D^{25}$ 35.9° (c 0.1, $CHCl_3$); FTIR:2905, 2850, 1713, 1605, 1382, 1113, 906, 729, 674 cm$^{-1}$; $^1$H NMR ($CDCl_3$, 500 MHz): δ 7.85 (dd, J=8.5, 5 Hz, 2H), 7.59 (d, J=3.5 Hz, 2H), 4.71 (s, 1H), 2.0-1.5 (m, 15H); $^{13}$C NMR (125 MHz, $CDCl_3$): δ 186.9, 167.9, 134.3, 131.8, 123.6, 61.9, 39.3, 37.7, 36.5, 33.7, 28.4. HRMS (FAB) calc for $C_{80}H_{80}N_4O_{16}Rh_2$ (M+H$^+$) 1559.368, found 1559.363.

(2R,3S)-Methyl 2,3-dihydro-2-phenylbenzofuran-3-carboxylate (27) was prepared as follows. The catalyst (1 mol %) was added to a solution of the diazo compound 26 (100 mg, 0.35 mmol) in toluene/hexanes (3.0 mL). After 0.5 h of stirring, the whole mixture was concentrated in vacuo. The diastereomeric ratio of the product was determined by $^1$H NMR of the crude reaction mixture. Purification by column chromatography (silica gel, 20:1 hexanes/ethyl acetate) afforded the product (27) as a white solid. The enantiomeric ratio of the product was determined by HPLC analysis. $^1$H NMR ($CDCl_3$, 500 MHz): δ 7.38-7.22 (m, 7H), 6.99-6.64 (m, 2H), 5.99 (d, J=9.9 Hz, 1H), 4.63 (d, J=9.9 Hz, 1H) 3.21 (s, 3H). The NMR data are consistent with the published data (Saito, which is hereby incorporated by reference). The enantiomeric excess was determined by HPLC using the published procedure (Callot, which is hereby incorporated by reference).

(2R,3R)-Methyl 2-(4-(benzyloxy)phenyl)-5-bromo-2,3-dihydrobenzofuran-3-carboxylate (29a) was prepared as follows. The catalyst (1 mol %) was added to a solution of the diazo compound 28 (25 mg, 0.05 mmol) in DCM (3 mL). After 0.5 h of stirring, the whole mixture was concentrated in vacuo. The diastereomeric ratio of the product was determined by $^1$H NMR of the crude reaction mixture. Purification by column chromatography (silica gel, 6:1 hexanes/ethyl acetate) afforded the product (29a) as a white solid. $^1$H NMR ($CDCl_3$, 500 MHz): δ=7.42-7.32 (m, 7H), 7.23 (d, J=9.0 Hz, 2H), 6.93 (d, J=9.0 Hz, 2H), 6.81 (d, J=9.0 Hz, 1H), 5.95 (d, J=9.5 Hz, 1H), 5.05 (s, 2H), 4.56 (d, J=9.5 Hz, 1H), 3.25 (s, 3H). The NMR data are consistent with published data (Kurosawa I, which is hereby incorporated by reference). The enantiomeric excess was determined by HPLC (Chiralpak OD-H, 10% $^i$PrOH/hexanes, 1.0 mL/min, 254 nm, $t_R$=28.0 min, major; $t_R$=15.7 min, minor).

An isomerization reaction of 29a to produce 29b was carried out using the following procedure (Callot, which is hereby incorporated by reference). To a solution of 29a (3.5 mg, 0.008 mmol) in THF (4 mL) at 45° C. was added a solution of NaOMe in MeOH (0.1 eq). After stirring for 0.5 h at 45° C., the reaction was quenched by pH 7 phosphate buffer (1M, 3 mL), and the whole mixture was extracted with AcOEt. The combined organic extracts were washed with water and brine and dried over anhydrous $Na_2SO_4$. Filtration and evaporation furnished the crude product, which was purified by column chromatography (6:1; hexanes/EtOAc) to provide 29b as colorless oil (3.2 mg). $^1$H NMR ($CDCl_3$, 500 MHz): δ 7.42-7.32 (m, 7H), 7.23 (d, J=9 Hz, 2H), 6.93 (d, J=9 Hz, 2H), 6.81 (d, J=9 Hz, 1H), 6.12 (d, J=7.5 Hz, 1H), 5.05 (s, 2H), 4.29 (d, J=7.5 Hz, 1H), 3.25 (s, 3H).

The NMR data are consistent with the published data (Kurosawa I, which is hereby incorporated by reference). The enantiomeric excess was determined by HPLC (Chiralpak OD-H, 10% $^i$PrOH/hexanes, 1.0 mL/min, 254 nm, $t_R$=10.02 min, major; $t_R$=11.6 min, minor).

(1S,2R)-Dimethyl 1,2-diphenylcyclopropyl-phosphonate (31) was prepared by the following procedure. A stirred mixture of alkene (5.0 equiv) and Rh(II) catalyst (1 mol %) in 2,2-dimethylbutane (5 mL) was heated under reflux under an argon atmosphere. To this solution was added the α-diazobenzylphosphonate (30) (1 eq, 0.2 mmol) in 2,2-dimethylbutane (10 mL) via syringe pump over 5 h, and the mixture was then stirred for an additional 8 h. The mixture was then concentrated in vacuo, and the residue was purified on silica. $^1$H NMR (CDCl$_3$, 500 MHz): δ 7.12 (m, 3H), 7.06 (m, 5H), 6.75 (m, 2H), 3.75 (d, $J_{HP}$=10.5 Hz, 3H), 3.69 (d, $J_{HP}$=10.5 Hz, 3H), 3.02 (ddd, $J_{HP}$=16.48, J=8.8, 6.7 Hz, 1H), 2.07 (ddd, $J_{HP}$=17.3, J=8.8, 5.1 Hz, 1H), 1.73 (ddd, $J_{HP}$=12.2, J=6.7, 5.1 Hz, 1H). The NMR data are consistent with the published data (Davies XII, which is hereby incorporated by reference). The enantiomeric excess was determined by HPLC using the published procedure (Tomioka et al., "Effect of the Phosphonate Group on the Reactivity of Carbenes. Neighbouring Phosphonate Group Participation,", J. Chem. Soc. Chem. Commun., (6):362-364 (1989), which is hereby incorporated by reference.

(R)-Dimethyl (cyclohexa-2,5-dienyl)(phenyl)methylphosphonate (32) was prepared as follows. To a stirred solution of 1,4-cyclohexadiene (0.09 mL, 1.0 mmol) and catalyst (1 mol %) in 5 mL of 2,2-dimethylbutane was added dimethyl α-diazobenzylphosphonate (30) (0.2 mmol) in 10 mL of 2,2-dimethylbutane via syringe pump over 5 h at reflux. The solvent was removed in vacuo, and the crude material was purified by flash column chromatography on silica gel (2:1 ether/pentane). $[\alpha]_D^{25}$ 3.8° (c 2.85, CDCl$_3$); FTIR (neat) 1641, 1247, 1056, 1029 cm$^{-1}$; $^1$H NMR (500 MHz, CDCl$_3$) δ 7.35-7.23 (m, 5H), 5.80 (m, 1H), 5.72 (m, 3H), 3.73 (d, $J_{HP}$=10.6 Hz, 3H), 3.58 (m, 1H), 3.42 (d, $J_{HP}$=10.3 Hz, 3H), 3.10 (dd, J=7.0, 21.9 Hz, 1H) 2.51 (m, 1H), 2.37 (m, 1H); $^{13}$C NMR (125 MHz, CDCl$_3$) δ 134.4 (d, $J_{CP}$=5.0 Hz), 130.1 (d, $J_{CP}$=7.4 Hz), 128.1 (d, $J_{CP}$=1.6 Hz), 127.1, 127.0, 126.2, 126.1, 126.0 (d, $J_{CP}$=1.1 Hz), 53.3, (d, $J_{CP}$=7.2 Hz), 52.2 (d, $J_{CP}$=7.3 Hz), 36.6 (d, $J_{CP}$=1.6 Hz) 29.6, 25.8; HRMS (ESI) m/z calcd for [C$_{15}$H$_{19}$O$_3$NaP]$^+$, (M$^+$+Na) 301.0964, found 301.0962. HPLC analysis (Chiralpak AS-H, 4% 2-propanol in hexanes, 0.8 mL/min, 254 nm; $t_R$(minor)=18.4 min; $t_R$(major)=23.4 min).

Example 4

Synthesis of Rh$_2$(S-TCPTAD)$_4$ and Use of Rh$_2$(S-PTAD)$_4$, Rh$_2$(S-TCPTAD)$_4$, and Other Dirhodium Catalysts for Enantioselective C—H Aminations The development of practical catalytic methods for the functionalization of unactivated C—H bonds is an area of intense current interest. Considerable advances have been made in recent years in many types of transformations, such as C—H oxidation, C—H borylation, C—H alkylation, C—H arylation, and C—H amination. C—H Amination has been greatly enhanced due to improved methods for the synthesis of rhodium nitrene intermediates, as shown in the following Scheme 2.

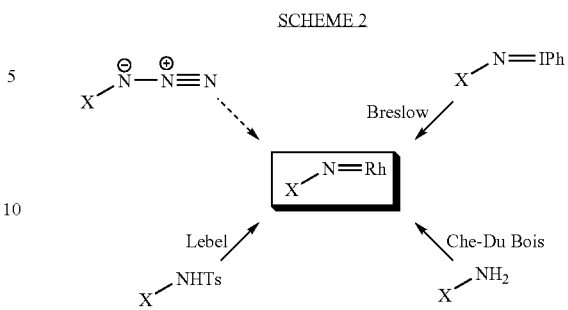

SCHEME 2

The direct rhodium catalyzed decomposition of azides is not an effective method for generating rhodium-nitrenes. The first generally applicable method, pioneered by Breslow, was to use preformed iodinanes (Breslow I; and Breslow II, which are hereby incorporated by reference). Che (Liang I; Yu; Au I; and Au II, which are hereby incorporated by reference) and Du Bois (Fiori; Espino I; Espino II; Kim; Espino III; and Wehn, which are hereby incorporated by reference) discovered an improved process, in which the iodinane is generated in situ, thereby opening up the chemistry to a range of primary amide and sulfonamide substrates. The synthetic potential of this process has been beautifully illustrated by Du Bois in the total synthesis of complex natural products such as tetrodotoxin (Hinmann, which is hereby incorporated by reference) and saxitoxin (Fleminget, which is hereby incorporated by reference). Recently, Lebel reported that tosyloxycarbamates can be used as nitrene precursor, and this approach also has great synthetic potential (Lebel; and Barani, which are hereby incorporated by reference).

The next natural extension for the C—H amination field is the development of effective chiral catalysts for this type of transformation. Chiral copper catalysts have been successfully applied to intermolecular aziridination, but dirhodium tetracarboxylates are the most widely used catalysts for the C—H amination chemistry (Davies et Al., "Recent Advances in Catalytic Intramolecular C—H Aminations," Angew. Chem., Int. Ed., 44(23):3518-3520 (2005); Muller et al., "Enantioselective Catalytic Aziridinations and Asymmetric Nitrene Insertions into CH Bonds," Chem. Rev., 103(8):2905-2920 (2003); Evans et al., "Copper-Catalyzed Aziridination of Olefins by (N-(p-Toluenesulfonyl)imino)-phenyliodinane," J. Org. Chem., 56(24):6744-6746 (1991); Quan et al., "Mechanism of the (Diimine)copper-Catalyzed Asymmetric Aziridination of Alkenes. Nitrene Transfer via Ligand-Accelerated Catalysis," J. Am. Chem. Soc., 117(21): 5889-5890 (1995); Espino et al., pp. 379-416 in Evans, ed., Modern Rhodium Catalyzed Organic Reactions; Wiley: New York (2005); Breslow I; Breslow II; Fiori; Espino I; Espino II; Kim; Espino III; and Wehn, which are hereby incorporated by reference. Several chiral catalysts have been applied using preformed iodinanes as the nitrene-precursor (Nageli et al., "Rhodium(II)-Catalyzed CH Insertions with {[(4-Nitrophenyl)sulfonyl]imino}phenyl-λ3-iodane," Helv. Chim. Acta, 80(4):1087-1105 (1997) ("Nageli"); Leung et al., "Nitrido Ruthenium Porphyrins: Synthesis, Characterization, and Amination Reactions with Hydrocarbon or Silyl Enol Ethers," Angew. Chem., Int. Ed., 42(3):340-343 (2003) ("Leung"); Liang et al., "Amidation of Silyl Enol Ethers and Cholesteryl Acetates with Chiral Ruthenium(II) Schiff-Base Catalysts: Catalytic and Enantioselective Studies," Chem. Commun., (2):124-125 (2002) ("Liang II"); Liang et al., "Metalloporphyrin-Mediated Asymmetric Nitrogen-Atom Transfer to Hydrocarbons: Aziridination of Alkenes and Amidation of Saturated C—H Bonds Catalyzed by Chiral Ruthenium and Manganese Porphyrins," *Chem.-Eur. J.,* 8(7):1563-1572 (2002) ("Liang III"); Kohmura et al., "Mn (salen)-Catalyzed Enantioselective C—H Amination," *Tetrahedron Lett.,* 42(19):3339-3342 (2001) ("Kohmura"); Omura et al., "Enantioselective Aziridination and Amination Using p-Toluenesulfonyl Azide in the Presence of Ru(salen) (CO) Complex," *Chem. Lett.,* 32(4):354 (2003) ("Omura"); Zhou et al., "Asymmetric Amidation of Saturated C—H Bonds Catalysed by Chiral Ruthenium and Manganese Porphyrins," *Chem. Commun.,* (23):2377-2378 (1999) ("Zhou"), which are hereby incorporated by reference). One of the most notable catalysts has been the rhodium phthalimide catalyst developed by Hashimoto, of which $Rh_2(S\text{-}TCPTTL)_4$, is considerably better at asymmetric C—H amination than the unchlorinated analog $Rh_2(S\text{-}PTTL)_4$ (Yamawaki et al., "Dirhodium(II) Tetrakis[N-tetrachlorophthaloyl-(S)-tert-leucinate]: A New Chiral Rh(II) Catalyst for Enantioselective Amidation of C—H Bonds," *Tetrahedron Lett.,* 43(52):9561-9564 (2002) ("Yamawaki"), which is hereby incorporated by reference). The related catalyst $Rh_2(S\text{-}NTTL)_4$ developed by Müller also shows promise in this chemistry (Fruit et al., "Intramolecular Asymmetric Amidations of Sulfonamides and Sulfamates Catalyzed by Chiral Dirhodium(II) Complexes," *Helv. Chim. Acta,* 87(7):1607-1615 (2004), which is hereby incorporated by reference). The formulae of $Rh_2(S\text{-}PTTL)_4$, $Rh_2(S\text{-}TCPTTL)_4$, and $Rh_2(S\text{-}NTTL)_4$ are set forth below:

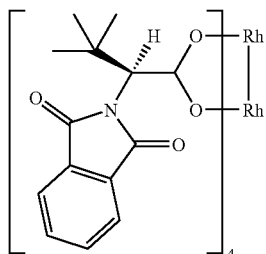

$Rh_2$ (S-PTTL)$_4$

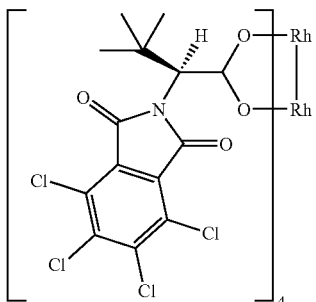

$Rh_2$ (S-TCPTTL)$_4$

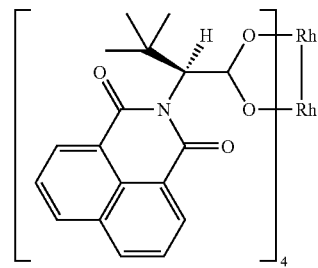

$Rh_2$ (S-NTTL)$_4$

Other effective catalysts have been manganese salen catalysts developed by Katsuki (Kohmura; Omura, which are hereby incorporated by reference) and manganese porphyrin catalysts developed by Che (Liang I; Yu; Au I; Au II; Leung; Liang II; Liang III; Kohmura; Omura; and Zhou, which are hereby incorporated by reference). Che has also demonstrated that a ruthenium porphyrin catalyst is effective in C—H aminations where the iodinane is generated in situ (Liang et al., "Highly Diastereo- and Enantioselective Intramolecular Amidation of Saturated C—H Bonds Catalyzed by Ruthenium Porphyrins," *Angew. Chem. Int. Ed.,* 41(18):3465-3468 (2002), which is hereby incorporated by reference).

As described above in Examples 1-3, during our studies on enantioselective intermolecular C—H alkylation, we discovered that adamantane could be readily functionalized, and we have applied this chemistry to the synthesis of $Rh_2(S\text{-}PTAD)_4$. As noted in Example 2, this catalyst tends to give higher enantioselectivity than $Rh_2(S\text{-}PTTL)_4$ in carbenoid reactions. Therefore, we became interested to see how effective $Rh_2(S\text{-}PTAD)_4$ and its chlorinated derivative $Rh_2(S\text{-}TCPTAD)_4$ would be in C—H amination reactions. $Rh_2(S\text{-}TCPTAD)_4$ has the following formula:

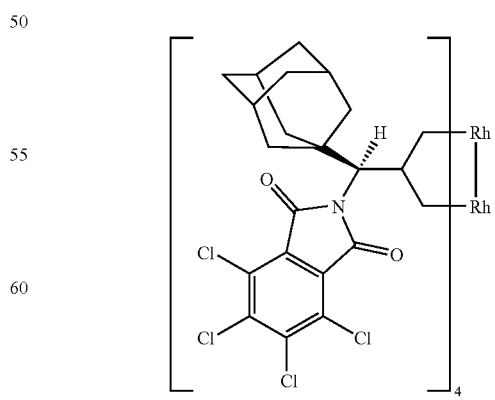

Rh$_2$(S-TCPTAD)$_4$ was prepared using the procedure outlined in Scheme I, except that tetrachlorophthalic anhydride was used instead of phthalic anhydride.

The new catalysts were tested under the Che-Du Bois conditions where the nitrene precursors are generated in situ. The results are presented in the following Table 6.

TABLE 6

| catalyst | yield, % | ee, % |
|---|---|---|
| Rh$_2$(OAc)$_4$ | 45 | |
| Rh$_2$(S-TCPTAD)$_4$ | 95 | 94 |
| Rh$_2$(S-PTAD)$_4$ | 86 | 59 |
| Rh$_2$(S-TCPTTL)$_4$ | 88 | 79 |
| Rh$_2$(S-PTTL)$_4$ | 81 | 43 |
| Rh$_2$(S-DOSP)$_4$ | 49 | (−) 11 |
| Rh$_2$(S-TBSP)$_4$ | 25 | (−) 31 |
| Rh$_2$(S-NTTL)$_4$ | 56 | 34 |
| Rh$_2$(S-MEOX)$_4$ | 12 | 10 |

As can be seen in the standard reaction for functionalizing indane, as presented in Table 6, Rh$_2$(S-TCPTAD)$_4$ was the most effective catalyst studied (94% ee). Our traditional catalyst for carbenoid chemistry, Rh$_2$(S-DOSP)$_4$, resulted in low enantioselecivity (11% ee) as did Rh$_2$(S-MEOX)$_4$ (10% ee) and Rh$_2$(S-NTTL)$_4$ (34% ee). Rh$_2$(S-TCPTTL)$_4$ gave relatively high asymmetric induction (79% ee), but did not match the results with Rh$_2$(S-TCPTAD)$_4$. The formulae of Rh$_2$(S-DOSP)$_4$, and Rh$_2$(S-TBSP)$_4$ Rh$_2$(S-MEOX)$_4$ are set forth below:

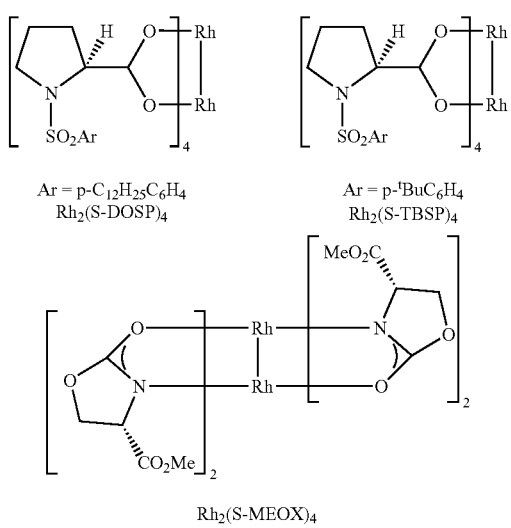

The Rh$_2$(S-TCPTAD)$_4$ catalyzed reactions were then examined with a range of substrates, and the results are summarized in the following Table 7.

TABLE 7

| compound | product | yield, % | ee, % |
|---|---|---|---|
| a | (1-phenylethyl)-NHNs | 86 | 74 |
| b | indanyl-NHNs | 92 | 62 |
| c | tetrahydronaphthalenyl-NHNs | 82 | 73 |
| d | indanone-NHNs | 75 | 76 |
| e | 6-MeO-indanone-NHNs | 85 | 74 |
| f | 6-Br-indanone-NHNs | 70 | 73 |
| g | tetralone-NHNs | 65 | 78 |

The general procedure for carrying out the reactions described in Table 7 were as follows. A solution of PhI(OAc)$_2$ (1.5 equiv) in trifluorotoluene (10 mL) was added over 30 min to a solution of substrate (5 equiv), NsNH2 (1 equiv), MgO (2.3 equiv), and the catalyst (2 mol %) in trifluorotoluene (15 mL) at 23° C. The reaction mixture was sirred for 3 h and then filtered to remove the precipitated solids. The filtrate was concentrated, and the residue was purified by column chromatography. This resulted in the formation of the products in good yields (65-92%) and reasonable enantioselectivities (62-78%). An excess of the substrate is optimum for these reactions as the efficiency of the reaction decreases considerably if less trapping agent is available. Due to solubility issues associated with the reagents used in this study, the reaction could not be improved by lowering the reaction temperature. The absolute configurations of 35, 37a, and 37c were shown to be (R) by comparison of optical rotation with literature values (15). The absolute configuration of the other products are tentatively assigned to be (R) by analogy.

Selective C—H amination could be very useful for the rapid synthesis of pharmaceutical agents. An illustration of this potential is the enantioselective synthesis of the (R) enantiomer of the anti-Parkinson agent Rasagiline (39). Previous methods for making Rasagiline and congeners thereof have been described in Graul et al., *Drugs Future*, 21:903ff (1996) ("Graul"); Sterling et al., "Novel Dual Inhibitors of AChE and MAO Derived from Hydroxy Aminoindan and Phenethylamine as Potential Treatment for Alzheimer's Disease," *J. Med. Chem.*, 45(24):5260-5279 (2002) ("Sterling"); and U.S. Pat. No. 5,639,913 to Lidor et al. ("Lidor"), which are hereby incorporated by reference. Our method for making Rasagiline (39) and Rasagiline congeners (such as those described in Graul; Sterling; and Lidor, which are hereby incorporated by reference) is set forth in Scheme 3.

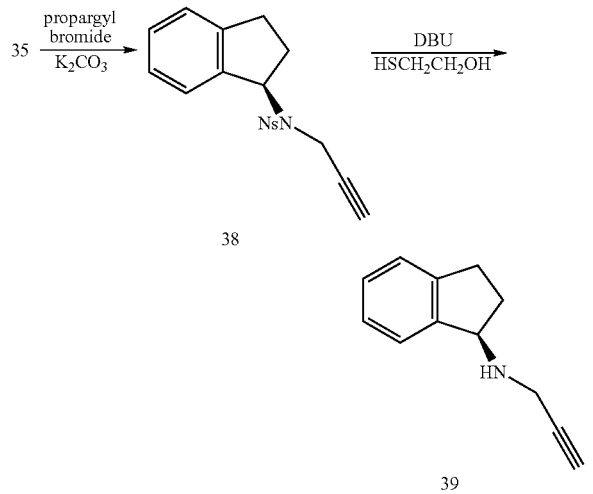

Alkylation of the sulfonamide 35 with propargylic bromide to form 38, followed by removal of the nosyl group in 38 using Fukuyama's protocol (Fukuyama et al., "2- and 4-Nitrobenzenesulfonamides: Exceptionally Versatile Means for Preparation of Secondary Amines and Protection of Amines," *Tetrahedron Lett.*, 36(36):6373-6374 (1995); and Kan et al., "Ns strategies: a highly versatile synthetic method for amines," *Chem. Commun.*, (4):353-359 (2004), which are hereby incorporated by reference) readily generates 39. Both enantiomers of Rh$_2$(TCPTAD)$_4$ can be accessed (as discussed in Example 1 and so, in principle, either enantiomer of 39 could be selectively formed.

The Rh$_2$(S-TCPTAD)$_4$-catalyzed enantioselective C—H amination can be extended to intramolecular reactions as illustrated in Table 8.

TABLE 8

| compound | product | yield, % | ee, % |
|---|---|---|---|
| a | (Ph, oxazolidinone) | 72 | 82 |
| b | (Ad, oxazolidinone) | 75 | 78 |
| c | (Ph-CH=CH, oxazolidinone) | 62 | 79 |
| d | (indane-fused oxazolidinone) | 69 | 43 |

Lebel's method (Lebel; Barani, which are hereby incorporated by reference) was used for generating the nitrene precursors in these examples. Briefly, K$_2$CO$_3$ (1.5 mmol, 3 equiv) and the catalyst (2 mol %) were added to a solution of N-tosyloxycarbamate (0.5 mmol) in dichloromethane (10.0 mL) at 23° C. The resulting suspension was stirred for 4 h. The mixture was filtered to remove the precipitate, and the solvent was removed under vacuum. The product was then purified by column chromatography. Reaction of the N-tosyloxycarbamates 40 generated the oxazolidinones 41 in good yields. With acyclic substrates 40a-40c, the enantioselectivity was quite reasonable (79-82% ee), but the C—H amination of the cyclic substrate 40d was less enantioselective (43% ee).

Further details regarding the synthesis of Rh$_2$(S-TCPTAD)$_4$ and other reactions described in this Example 4 are provided in Example 5.

Example 5

Experimental Details for Synthesis of Rh₂(S-TCPTAD)₄ and Use of Rh₂(S-PTAD)₄, Rh₂(S-TCPTAD)₄, and Other Dirhodium Catalysts for Enantioselective C—H Aminations This Example 5 provides some additional details with regard to the experiments described in Example 4.

$^1$H NMR spectra were run at either 400 or 500 MHz, and $^{13}$C NMR at either 75 or 125 MHz with the sample solvent being CDCl₃ unless otherwise noted. Mass spectral determinations were carried out in GC-MS (EI), LC-MS (ESI) or by Instrument Center, Department of Chemistry, University at Buffalo. IR spectra were obtained using a Perkin Elmer 1760X FT-IR. Optical rotations were measured using a Jasco DIP-370 digital polarimeter. Elemental analyses were performed by Atlantic Microlabs Inc., Norcross Ga. Enantiomeric excess was determined by HPLC (UV detection at 254 nm). Analytical TLC was performed on 0.25 mm E. Merck silica gel (60F-254) plates using UV light. Glassware was dried in oven overnight then flame or heat-gun dried prior to use. Reactions were conducted under argon atmosphere. Column chromatography was carried out on Merck silica gel 60 (230-400 mesh). Solvents THF, Et₂O, CH₃CN, CH₂Cl₂, and toluene were dried by solvent purifier.

2-((S)-1-Adamantyl-2-hydroxyethyl)4,5,6,7-tetrachloroisoindoline-1,3-dione, having the following formula:

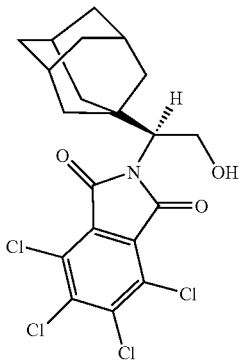

was prepared as follows. Tetrachlorophthalic anhydride (0.76 g, 5.12 mmol, 1.0 equiv.) was added to a solution of (S)-2-amino-2-adamantylethanol (1.0 g, 5.12 mmol, 1.0 equiv.) in DMF (6 mL) and heated at 140° C. for 12 h. After cooling, the reaction mixture was poured into water, and the product precipitated out as a white solid. The crystals were filtered and vacuum dried to give the product (1.9 g, 80% yield) as a white sticky solid. $R_f$=0.35 (3:1 hexane/EtOAc); $[\alpha]_D^{25}$ −4.5° (c 0.22, CHCl₃); IR (neat) 3273, 2903, 2849, 1641, 1543, 1401, 1343, 1266, 1132 cm$^{-1}$; $^1$H NMR (CDCl₃, 500 MHz) δ 4.53 (t, J=13.5 Hz, 1H), 4.04 (dd, J=5.5, 13.5 Hz, 1H), 3.98 (dd, J=5.5, 13.5 Hz, 1H), 1.98 (bs, 3H), 1.71-1.60 (m, 13H); $^{13}$C NMR (125 MHz, CDCl₃) δ 165.1, 129.7, 127.4, 127.3, 64.4, 57.5, 40.1, 37.1, 36.7, 28.3; HRMS (ESI) m/z Calcd for $[C_{20}H_{20}Cl_4NO_3]^+$ $[(M+H)^+]$: 462.0197. Found: 462.0201.

(S)-Adamantan-1-yl-(4,5,6,7-tetrachloro-1,3-dioxo-1,3-dihydro-isoindol-2-yl)-acetic acid, having the following formula:

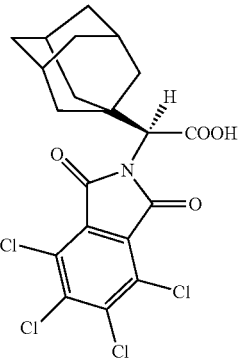

was prepared as follows. NaIO₄ (3.4 g, 16.0 mmol, 4.1 eq) in water (25 mL) was added to a stirring solution of 2-((S)-1-adamantyl-2-hydroxyethyl) 4,5,6,7-tetrachloroisoindoline-1,3-dione (1.8 g, 3.9 mmol) in (1:1) EtOAc/CH₃CN (34 mL), and stirred at 23° C. for 10 min. RuCl₃·H₂O (0.02 g, 2.2 mol %) was then added and stirred vigorously for 12 h. The reaction mixture was diluted with DCM and filtered through a pad of celite and charcoal. The filtrate was washed with water and brine and dried over anhydrous MgSO₄, and the solvent was removed in vacuo. The resulting residue was dissolved in ether (25 mL) and filtered through a pad of celite and charcoal. The solvent was then concentrated to give the product (1.26 g, 68%) as a white solid. $R_f$=0.17 (1:1 hexane/EtOAc); $[\alpha]_D^{25}$ −14.4° (c 0.15, CHCl₃); IR (neat): 2906, 2851, 1723, 1387, 1370, 737 cm$^{-1}$; $^1$H NMR (CDCl₃, 400 MHz) δ 4.57 (s, 1H), 1.99-1.66 (m, 15H); $^{13}$C NMR (125 MHz, CDCl₃) δ 170.9, 163.5, 140.5, 130.0, 127.2, 61.2, 39.3, 37.8, 36.5, 28.4; HRMS (EI) m/z Calcd for $C_{20}H_{17}Cl_3NO_4{}^{37}Cl_1$: 476.9877. Found: 476.9862.

Rh₂(S-TCPTAD)₄ was prepared using a procedure similar to that reported in Callot, which is hereby incorporated by reference. (S)-Adamantan-1-yl-(4,5,6,7-tetrachloro-1,3-dioxo-1,3-dihydro-isoindol-2-yl)-acetic acid (1.2 g, 2.5 mmol, 6 equiv.) and Rh₂(OAc)₄ (188 mg, 0.42 mmol) were dissolved in dry chlorobenzene (12 mL) in a flask under argon and stirred at 23° C. for 30 min. The mixture was then heated up to 150° C., and the acetic acid was distilled out as an azeotrope with chlorobenzene for 3 h. Additional 25 mL of chlorobenzene was added and distilled during the reaction. The mixture was cooled, and the solvent was removed in vacuo. The residue was subjected to flash chromatography (silica, 1.5:1 hexanes/EtOAc-1:1 hexanes/EtOAc) to give Rh₂(S-TCPTAD)₄ (0.55 g, 62%) as a bright green solid. $R_f$=0.7 (1:3 hexanes:EtOAc); $[\alpha]_D^{25}$ +82.6° (c 0.19, CHCl₃); FTIR: 2904, 2850, 1726, 1610, 1370, 1200, 740 cm$^{-1}$; $^1$H NMR (CDCl₃, 400 MHz) δ 4.70 (s, 1H), 1.99-1.67 (m, 15H); $^{13}$C NMR (125 MHz, CDCl₃) δ 186.2, 163.4, 162.8, 140.2, 139.8, 130.1, 129.3, 127.3, 62.3, 39.3, 38.4, 36.9, 28.5; HRMS (FAB) calc for $[C_{80}H_{64}Cl_{16}N_4O_{16}Rh_2]^+$ $([M+H]^+)$ 2102.7522. Found: 2102.7536.

The general procedure used for intermolecular C—H aminations was as follows. A solution of PhI(OAc)₂ (1.5 equiv.) in trifluorotoluene (10 mL) was added to a solution of substrate (5 equiv.) NsNH₂ (1 equiv.), MgO (2.3 equiv.), and the catalyst (2 mol %) in trifluorotoluene (15 mL) at 23° C. over 0.5 h using a syringe pump. The reaction mixture was allowed to stir for 3 h and then filtered to remove the precipitated solids. The filtrate was concentrated, and the residue was purified using flash column chromatography.

(R)-N-Indan-1-yl-4-nitro-benzenesulfonamide (35) was prepared using the above general intermolecular C—H amination procedure. $^1$H NMR (CDCl$_3$, 400 MHz) δ 8.38 (d, J=8.8 Hz, 2H), 8.12 (d, J=8.8 Hz, 2H), 7.15-7.26 (m, 3H), 7.09 (d, J=7.2 Hz, 1H), 4.93-4.89 (m, 2H), 2.97-2.90 (m, 1H), 2.85-2.76 (m, 1H), 2.35-2.42 (m, 1H), 1.76-1.82 (m, 1H); $[\alpha]_D^{25}$ +16.4° (c 0.68, CHCl$_3$, 94% ee). Lit. $[\alpha]_D$ +22.7° (c 1.30, CHCl$_3$) (Yamawaki, which is hereby incorporated by reference); HPLC analysis: 94% ee. Chiralcel AD-H, 25.0% i-PrOH, 0.8 mL/min, 12.6 min (major), 18.3 min (minor). The NMR data are consistent with the published data (Nageli, which is hereby incorporated by reference).

(R)-N-(1-Phenyl-ethyl)-4-nitro-benzenesulfonamide (37a) was prepared using the above general intermolecular C—H amination procedure. $^1$H NMR (CDCl$_3$, 400 MHz) δ 8.40 (d, J=8.5 Hz, 2H), 8.12 (d, J=8.5 Hz, 2H), 7.18-7.15 (m, 2H), 7.10-7.06 (m, 2H), 6.95 (d, J=7.5 Hz, 1H), 4.84 (d, J=8.0 Hz, 1H), 4.58-4.55 (m, 1H), 2.77-2.69 (m, 3H; $[\alpha]_D^{25}$ +11.6° (c 0.73, CHCl$_3$). Lit. $[\alpha]_D$ +6.23° (c 0.80, CHCl$_3$) (Yamawaki, which is hereby incorporated by reference); HPLC analysis: 74% ee. Chiralcel OD-H, 1.0% i-PrOH, 0.7 mL/min, 5.8 min (major), 11.1 min (minor). The NMR data are consistent with the published data (Nageli, which is hereby incorporated by reference).

(R)-N-(5-Methoxy-indan-1-yl)-4-nitro-benzenesulfonamide (37b) was prepared using the above general intermolecular C—H amination procedure as a white solid; mp=95-98° C. R$_f$=0.40 (2:1 hexanes:EtOAc); $[\alpha]_D^{25}$ +44.9° (c 0.12, acetone); FTIR: 3286, 2946, 1607, 1530, 1493, 1434, 1349, 1164, 1093, 1029, 851, 736, 643, 619 cm$^{-1}$; $^1$H NMR (D$_2$O, 500 MHz) δ 8.38 (d, J=7.0 Hz, 2H), 8.12 (d, J=7.0 Hz, 2H), 6.97 (d, J=8.0 Hz, 1H), 6.70 (m, 2H), 4.86 (s, 2H), 3.77 (s, 3H), 2.89 (m, 1H), 2.77 (m, 1H), 2.36 (m, 1H), 1.79 (m, 1H); $^{13}$C NMR (125 MHz, CDCl$_3$) δ 160.1, 157.1, 147.2, 145.3, 133.0, 128.1, 125.1, 124.6, 103.1, 100.4, 58.8, 55.9, 35.5, 30.1; HRMS (EI) m/z calc for [C$_{16}$H$_{16}$N$_2$O$_5$S]$^+$ [(M)$^+$]: 348.0774. Found: 348.0779; HPLC analysis: Chiralcel AD-H, 25.0% ipa, 0.7 mL/min, 24.0 min (major), 26.3 min (minor).

(R)-N-(1,2,3,4-Tetrahydronaphthalene-1-yl)-4-nitro-benzenesulfonamide (37c) was prepared using the above general intermolecular C—H amination procedure. $^1$H NMR (CDCl$_3$, 400 MHz) δ 8.40 (d, J=8.8 Hz, 2H), 8.12 (d, J=8.8 Hz, 2H), 7.17 (t, J=7.2 Hz, 1H), 7.10-7.05 (m, 2H), 6.95 (d, J=7.2 Hz, 1H), 4.83 (d, J=7.6 Hz, 1H), 4.58-4.55 (m, 1H), 2.81-2.66 (m, 2H), 1.88-1.71 (m, 4H); $[\alpha]_D^{25}$ +34.1° (c 0.64, CHCl$_3$, 73% ee), Lit. $[\alpha]_D$ 44.3° (c 1.40, CHCl$_3$) (Yamawaki, which is hereby incorporated by reference); HPLC analysis: 73% ee. Chiralcel AD-H, 25.0% i-PrOH, 0.7 mL/min, 12.9 min (major), 19.6 min (minor). The NMR data are consistent with the published data (Nageli, which is hereby incorporated by reference).

(R)-N-(3-oxo-indan-1-yl)-4-nitrobenzenesulfon-amide (37d) was prepared using the above general intermolecular C—H amination procedure as a yellow solid; mp=198-200° C.; R$_f$=0.40 (2:1 hexanes:EtOAc); $[\alpha]_D^{25}$ −10.5° (c 0.19, acetone, 76% ee); FTIR: 2966, 2906, 2854, 1707, 1530, 1349, 1259, 1166, 1067, 854, 736 cm$^{-1}$; $^1$H NMR (DMSO, 500 MHz) δ 8.73 (d, J=8.5 Hz, 1H), 8.47 (d, J=9.0 Hz, 2H), 8.13 (d, J=9.0 Hz, 2H), 7.74 (t, J=7.5 Hz, 1H), 7.64 (d, J=8.0 Hz, 1H), 7.54 (m, 1H), 5.10 (m, 1H), 2.80 (dd, J=19.0, 8.0 Hz, 1H), 2.20 (dd, J=19.0, 3.5 Hz, 1H); $^{13}$C NMR (125 MHz, CDCl$_3$) δ 202.0 (C), 153.2 (C), 149.7 (C), 136.0 (CH), 135.5 (C), 129.2 (CH), 128.1 (CH), 126.2 (CH), 124.8 (CH), 122.5 (CH), 50.9 (CH), 43.8 (CH); Anal. Calcd for C$_{15}$H$_{12}$N$_2$O$_5$S: C, 54.21; H, 3.64; N, 8.43. Found: C, 54.40; H, 3.55; N, 8.39; HPLC analysis: 76% ee. Chiralcel OJ, 5% i-PrOH, 0.8 mL/min, 5.4 min (minor), 7.1 min (major).

(R)-N-(5-Methoxy-3-oxo-indan-1-yl)-4-nitrobenzenesulfonamide (37e) was prepared using the above general intermolecular C—H amination procedure as a yellow solid; mp=165-167° C.; R$_f$=0.37 (2:1 Hex:EtOAc); $[\alpha]_D^{25}$ −20.9° (c 0.45, acetone, 74% ee); FTIR: 3305, 1711, 1692, 1527, 1493, 1350, 1285, 1155, 1089, 855, 740, 669, 616 cm$^{-1}$; $^1$H NMR (DMSO, 500 MHz) δ 8.66 (d, J=8.5 Hz, 1H), 8.47 (d, J=8.5 Hz, 2H), 8.09 (d, J=8.5 Hz, 2H) 7.37 (d, J=8.0 Hz, 1H), 7.28 (dd, J=2.5, 8.5 Hz, 1H) 7.06 (s, 1H), 5.00 (m, 1H), 3.79 (s, 3H), 2.80 (dd, J=18.5, 7.0 Hz, 1H), 2.20 (dd, J=18.5, 3.0 Hz, 1H); $^{13}$C NMR (125 MHz, CDCl$_3$) δ 201.8 (C), 160.3 (C), 149.7 (C), 146.9 (C), 145.7 (C), 137.5 (C), 128.1 (CH), 127.2 (CH), 124.8 (CH), 123.7 (CH), 104.4 (CH), 55.7 (CH3), 50.5 (CH), 44.4 (CH2); HRMS (ESI) m/z calc for [C$_{16}$H$_{14}$N$_2$O$_6$SNa]$^+$ (M+Na)$^+$ 385.0465. Found: 385.0460; HPLC analysis: 74% ee: Chiralcel OJ, 5.0% i-PrOH, 0.8 mL/min, 6.9 min (major), 12.4 min (minor).

(R)-N-(5-Bromo-3-oxo-indan-1-yl)-4-nitrobenzene-sulfonamide (37f) was prepared using the above general intermolecular C—H amination procedure as a yellow sticky solid; R$_f$=0.47 (2:1 Hex:EtOAc); $[\alpha]_D^{25}$ −6.25° (c 0.32, acetone, 73% ee); FTIR: 3419, 2360, 2325, 1653, 1023, 762 cm$^{-1}$; $^1$H NMR (DMSO, 500 MHz) δ 8.76 (bs, 1H), 8.46 (d, J=8.5 Hz, 2H), 8.11 (d, J=8.5 Hz, 2H), 7.90 (d, J=8.0 Hz, 1H), 7.78 (s, 1H), 7.45 (d, J=8.0 Hz, 1H), 5.06 (bs, 1H), 2.83 (dd, J=7.5, 18.5 Hz, 1H), 2.20 (dd, J=3.0, 18.5 Hz, 1H); $^{13}$C NMR (125 MHz, CDCl$_3$) δ 200.6, 152.1, 149.7, 146.6, 138.0, 137.8, 128.4, 128.1, 125.0, 124.7, 122.7, 50.7, 43.9; HRMS (EI) m/z calc for [C$_{15}$H$_{11}$BrN$_2$O$_5$S]$^+$ (M$^+$): 409.9567. Found: 409.9576; HPLC analysis: 73% ee. Chiralcel OJ, 5.0% i-PrOH, 0.8 mL/min, 5.4 min (major), 7.1 min (minor).

(R)-N-(4-Oxo-1,2,3,4-tetrahydronaphthalene-1-yl)-4-nitrobenzenesulfonamide (37g) was prepared using the above general intermolecular C—H amination procedure. R$_f$=0.40 (2:1 hexanes:EtOAc); $[\alpha]_D^{25}$ −13.4° (c 1.02, acetone, 78% ee); FTIR: 2966, 2906, 2854, 1707, 1530, 1349, 1259, 1166, 1067, 854, 736 cm$^{-1}$; $^1$H NMR (DMSO, 300 MHz) δ 8.75 (d, J=8.7 Hz, 1H), 8.44 (d, J=8.7 Hz, 2H), 8.14 (d, J=8.7 Hz, 2H), 7.84 (d, J=7.8 Hz, 1H), 7.61 (t, J=7.8 Hz, 1H), 7.43 (t, J=7.5 Hz, 1H), 7.34 (d, J=7.8 Hz, 1H), 4.78 (m, 1H), 2.61 (m, 2H), 1.93 (m, 2H); $^{13}$C NMR (125 MHz, DMSO) δ 196.1, 149.6, 147.4, 143.1, 133.8, 131.5, 128.1, 127.9, 127.7, 126.3, 124.7, 51.2, 35.2, 29.5; HRMS (EI) m/z calc for [C$_{16}$H$_{14}$N$_2$O$_5$S]$^+$ (M$^+$): 346.0623. Found: 346.0634; HPLC analysis: 78% ee. Chiralcel OJ, 5.0% i-Propanol, 0.8 mL/min, 15.4 min (minor), 18.1 min (major).

(R)-N-Indan-1-yl-4-nitro-N-prop-2-ynyl-benzenesulfonamide (38) was prepared using the above general intermolecular C—H amination procedure as a light yellow solid; mp=102-105° C.; R$_f$=0.40 (5:1 hexanes:EtOAc); $[\alpha]^{p25}$ −12.3° (c 1.17, CHCl$_3$); FTIR: 3281, 3101, 2946, 1528, 1348, 1158, 1093, 855, 737, 684 cm$^{-1}$; $^1$H NMR (CDCl$_3$, 500 MHz) δ 8.40 (d, J=7.0 Hz, 2H), 8.22 (d, J=7.0 Hz, 2H), 7.29-7.15 (m, 4H), 5.61 (t, J=7.5 Hz, 1H), 4.28 (dd, J=19.0, 2.5 Hz, 1H), 3.60 (dd, J=19.0, 2.5 Hz, 1H), 3.04 (m, 1H), 2.83 (m, 1H), 2.23 (m, 2H), 2.12 (s, 1H); $^{13}$C NMR (125 MHz, CDCl$_3$) δ 149.9 (C), 146.5 (C), 143.6 (C), 138.8 (C), 128.9 (CH), 128.8 (CH), 127.1 (CH), 125.1 (CH), 124.5 (CH), 124.1 (CH), 78.9 (C), 72.9 (C), 63.8 (CH), 32.8 (CH2), 30.1 (CH2), 29.1 (CH2); HRMS (EI) m/z calc for [C$_{18}$H$_{16}$N$_2$O$_4$S]$^+$ (M$^+$): 356.0825. Found: 356.0819.

(R)-Indan-1-yl-prop-2-ynyl-amine (39) was prepared using the above general intermolecular C—H amination procedure as a solid; mp=148° C. $R_f$=0.33 (3:1 hexanes: EtOAc); $[\alpha]_D^{25}$ +18.8° (c 1.7, CHCl$_3$); FTIR: 3281, 2929, 2848, 1456, 1349, 1161, 1088, 649 cm$^{-1}$; $^1$H NMR (CDCl$_3$, 300 MHz) δ 7.57-7.54 (m, 1H), 7.46-7.39 (m, 3H), 4.62 (t, J=10 Hz, 1H), 3.73 (s, 2H), 3.25 (m, 1H), 3.06 (m, 1H), 2.62 (m, 1H), 2.46 (s, 1H), 2.12 (m, 2H); $^{13}$C NMR (125 MHz, CDCl$_3$) δ 144.5 (C), 143.8 (C), 127.6 (CH), 126.2 (CH), 124.8 (CH), 124.2 (CH), 82.5 (C), 71.3 (C), 61.9 (CH), 36.1 (CH2), 33.3 (CH2), 30.4 (CH2); HRMS (ESI) m/z calc for [C$_{12}$H$_{13}$NNa]$^+$ ([M+Na]$^+$): 194.0946. Found: 194.0932.

The general procedure used for intramolecular C—H aminations was as follows. To a solution of N-tosyloxycarbamate (0.5 mmol) in dichloromethane (10.0 mL), were added K$_2$CO$_3$ (1.5 mmol, 3 equiv.) and Rh$_2$(S-TCPTAD)$_4$ (0.01 mmol). The resulting suspension was stirred at 23° C. for 4 h. The mixture was filtered to remove the precipitate, and the solvent was removed under vacuum. The crude reaction mixture was then purified by flash chromatography.

(R)-4-Phenyloxazolidin-2-one (41a) was prepared using the above general intramolecular C—H amination procedure. $^1$H NMR (400 MHz, CDCl$_3$) δ 7.42-7.32 (m, 5H), 6.11 (bs, 1H), 4.95 (t, J=7.6 Hz, 1H), 4.72 (t, J=8.8 Hz, 1H), 4.17 (dd, J=8.8, 7.6 Hz, 1H); $[\alpha]_D^{25}$ −40.8° (c 0.86, CHCl$_3$, 82% ee) Lit. $[\alpha]_D$ for (R)-4-phenyloxazolidin-2-one (Evans et al., "The Asymmetric Synthesis of β-Lactam Antibiotics—I. Application of Chiral Oxazolidones in the Staudinger Reaction," Tetrahedron Lett., 26(32):3783-3786 (1985), which is hereby incorporated by reference): −57.7° (c 1.00, CHCl$_3$); HPLC analysis. 82% ee. Chiralcel OD-H, 7% i-PrOH, 0.9 mL/min, 14.0 min (major), 17.2 min (minor). The NMR data are consistent with the published data (Espino I; and Lebel, which are hereby incorporated by reference).

(R)-4-Adamantyloxazolidin-2-one (41b) was prepared using the above general intramolecular C—H amination procedure. $^1$H NMR (500 MHz, CDCl$_3$) δ 5.62 (bs, 1H), 4.30 (d, J=7.5 Hz, 2H), 3.40 (t, J=7.2 Hz, 1H), 2.03 (s, 3H), 1.77-1.51 (m, 12H); $[\alpha]_D^{25}$ −12.5° (c 0.62, CHCl3, 78% ee); Lit. $[\alpha]_D$ for (S)-4-adamantyloxazolidin-2-one (Takacs et al., "Preparation of Chiral Oxazolidin-2-ones and Vicinal Amino Alcohols," J. Org. Chem., 63(8):2742-2748 (1998), which is hereby incorporated by reference): +8.1° (c 0.78, CHCl$_3$); HPLC analysis. 78% ee. Chiralcel OD-H, 0.9 mL/min, 7% i-PrOH, 13.1 min (minor), 24.7 min (major). The NMR data are consistent with the published data (Espino I; and Lebel, which are hereby incorporated by reference).

(R)-4-Styryloxazolidin-2-one (41c) was prepared using the above general intramolecular C—H amination procedure. $^1$H NMR (500 MHz, CDCl$_3$) δ 7.39-7.30 (m, 5H), 6.62 (d, J=16.0 Hz, 1H), 6.14 (dd, J=16.0, 8.0 Hz, 1H), 5.09 (bs, 1H), 4.63-4.54 (m, 2H), 4.16 (m, 1H); $[\alpha]_D^{25}$ +22.5° (c 0.26, CHCl$_3$), Lit. $[\alpha]_D$ for (R)-4-styryloxazolidin-2-one (Sibi et al., "Investigations of a Nucleophilic Alaminol Synthon Derived from Serine," J. Am. Chem. Soc., 121(33):7509-7516 (1999), which is hereby incorporated by reference): +19.3° (c 1.945, CHCl$_3$); HPLC analysis. 79% ee. Chiralcel OD-H, 10.0% i-PrOH, 0.9 mL/min, 8.5 min (minor), 15.3 min (major). The NMR data are consistent with the published data (Espino I; and Lebel, which are hereby incorporated by reference).

(4R,5S)-Indano[1,2-d]oxazolidin-2-one (41d) was prepared using the above general intramolecular C—H amination procedure. $^1$H NMR (500 MHz, CDCl$_3$) δ 7.33-7.26 (m, 4H), 6.87 (bs, 1H), 5.43-5.40 (m, 1H), 5.17 (d, J=7.0, 1H), 3.44-3.34 (m, 2H); $[\alpha]_D^{25}$ +12.1° (c 0.36, CHCl$_3$, 43% ee); Lit. $[\alpha]_D$ for (4R,5S)-indano[1,2-d]oxazolidin-2-one (Ghosh et al., "A Convenient Enzymatic Route to Optically Active 1-Aminoindan-2-ol: Versatile Ligands for HIV-1 Protease Inhibitors and Asymmetric Syntheses," Synthesis, (5):541-544 (1997), which is hereby incorporated by reference): +76.9° (c 1.2, CHCl$_3$); HPLC analysis. 43% ee. Chiralcel AD-H, 7% i-PrOH, 0.9 mL/min, 17.0 min (major), 29.0 min (minor). The NMR data are consistent with the published data (Espino I; and Lebel, which are hereby incorporated by reference).).

Although the invention has been described in detail for the purpose of illustration, it is understood that such detail is solely for that purpose, and variations can be made therein by those skilled in the art without departing from the spirit and scope of the invention which is defined by the claims that are set forth below.

What is claimed is:

1. A compound having the formula:

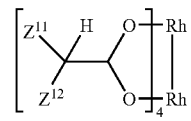

in which $Z^{11}$ is selected from a substituted or unsubstituted saturated polycyclic group and a substituted or unsubstituted branched acyclic group containing at least 5 carbon atoms at least one of which is a tertiary carbon; and in which $Z^{12}$ is a cyclic imide.

2. A compound according to claim 1, wherein $Z^{11}$ is a substituted or unsubstituted saturated polycyclic group.

3. A compound according to claim 2, wherein said compound is substantially chirally pure and has one of the following formulae:

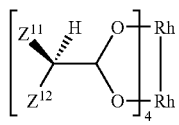 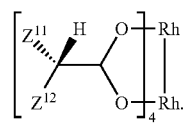

4. A compound according to claim 2, wherein $Z^{11}$ is an adamantyl group.

5. A compound according to claim 2 having the formula:

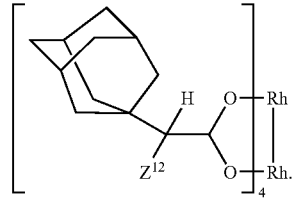

6. A compound according to claim 5, wherein said compound is substantially chirally pure and has one of the following formulae:

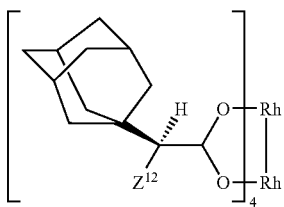

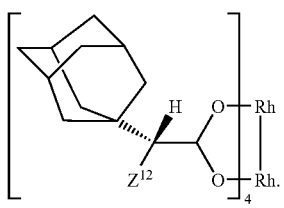

7. A compound according to claim 2, wherein $Z^{12}$ has the formula:

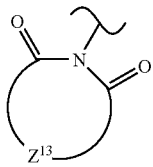

in which $Z^{13}$ represents the atoms needed to complete a substituted or unsubstituted ring or ring system.

8. A compound according to claim 7, wherein $Z^{13}$ is a 5-, 6-, 7-, or 8-membered ring or a 9-, 10-, 11-, 12-, 13-, 14-, 15-, or 16-membered ring system.

9. A compound according to claim 2, wherein $Z^{12}$ is a substituted or unsubstituted cyclic imide having at least one substituted or unsubstituted aryl group fused thereto.

10. A compound according to claim 9, wherein $Z^{12}$ is a substituted or unsubstituted phthalimide.

11. A compound according to claim 9, wherein $Z^{12}$ has the formula:

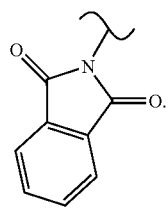

12. A compound according to claim 9, wherein $Z^{12}$ has the formula:

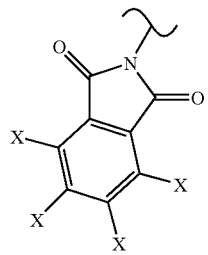

wherein each X represents a halogen atom.

13. A compound according to claim 9, wherein each X represents a chlorine atom.

14. A compound according to claim 9, wherein $Z^{12}$ has one of the following formulae:

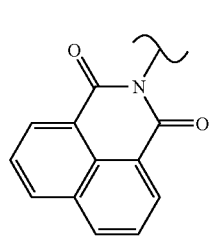 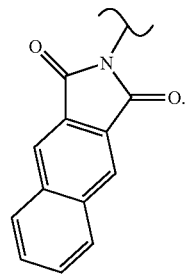

15. A compound according to claim 2 having the formula:

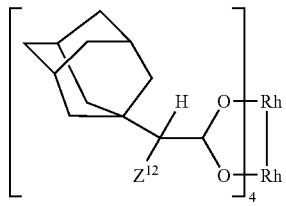

wherein $Z^{12}$ has the formula:

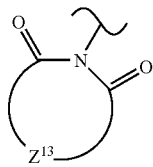

in which $Z^{13}$ represents the atoms needed to complete a substituted or unsubstituted ring or ring system.

16. A compound according to claim 15, wherein said compound is substantially chirally pure and has one of the following formulae:

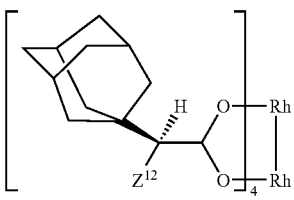

17. A compound according to claim 15, wherein $Z^{13}$ is a 5-, 6-, 7-, or 8-membered ring or a 9-, 10-, 11-, 12-, 13-, 14-, 15-, or 16-membered ring system.

18. A compound according to claim 16, wherein $Z^{12}$ is a substituted or unsubstituted cyclic imide having at least one substituted or unsubstituted aryl group fused thereto.

19. A compound according to claim 18, wherein $Z^{12}$ is a substituted or unsubstituted phthalimide.

20. A compound according to claim 18, wherein $Z^{12}$ has the formula:

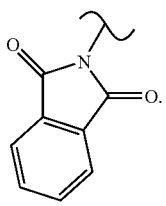

21. A compound according to claim 18, wherein $Z^{12}$ has the formula:

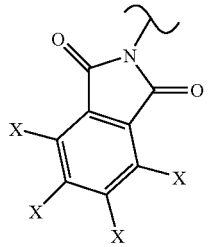

wherein each X represents a halogen atom.

22. A compound according to claim 21, wherein each X represents a chlorine atom.

23. A compound according to claim 18, wherein $Z^{12}$ has one of the following formulae:

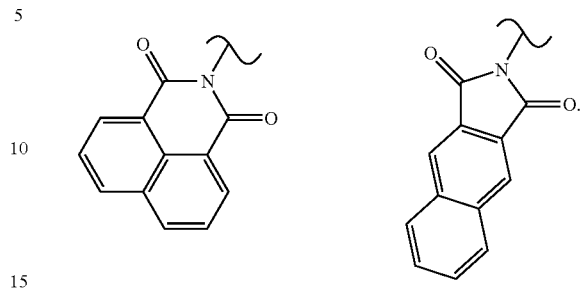

24. A compound according to claim 1, wherein $Z^{11}$ is a substituted or unsubstituted branched acyclic group containing at least 5 carbon atoms at least one of which is a tertiary carbon; and in which $Z^{12}$ is a cyclic imide.

25. A compound according to claim 24, wherein said compound is substantially chirally pure and has one of the following formulae:

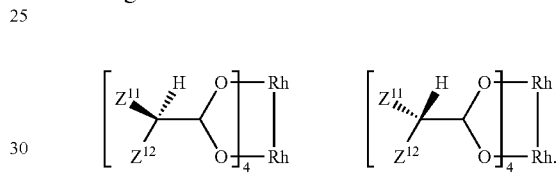

26. A compound according to claim 24, wherein $Z^{11}$ is has the formula $-CR^{51}R^{52}R^{53}$, wherein $R^{51}$, $R^{52}$, and $R^{53}$ are the same or different alkyl groups at least one of $R^{51}$, $R^{52}$, and $R^{53}$ is an alkyl containing 2 or more carbon atoms.

27. A compound according to claim 24, wherein $Z^{11}$ is has the formula $-CR^{51}R^{52}R^{53}$, wherein $R^{51}$, $R^{52}$, and $R^{53}$ are the same or different alkyl groups at least one of $R^{51}$, $R^{52}$, and $R^{53}$ is a branched alkyl.

28. A compound according to claim 24, wherein $Z^{11}$ is has the formula $-CR^{51}R^{52}R^{53}$, wherein each of $R^{51}$ and $R^{52}$ is a methyl group and $R^{53}$ is a C2-C8 alkyl group.

29. A compound according to claim 24, wherein $Z^{12}$ has the formula:

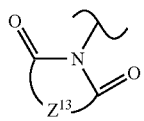

in which $Z^{13}$ represents the atoms needed to complete a substituted or unsubstituted ring or ring system.

30. A compound according to claim 29, wherein $Z^{13}$ is a 5-, 6-, 7-, or 8-membered ring or a 9-, 10-, 11-, 12-, 13-, 14-, 15-, or 16-membered ring system.

31. A compound according to claim 24, wherein $Z^{12}$ is a substituted or unsubstituted cyclic imide having at least one substituted or unsubstituted aryl group fused thereto.

32. A compound according to claim 31, wherein $Z^{12}$ is a substituted or unsubstituted phthalimide.

33. A compound according to claim 31, wherein $Z^{12}$ has the formula:

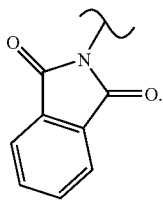

34. A compound according to claim 31, wherein $Z^{12}$ has the formula:

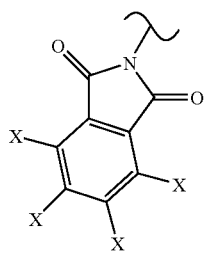

wherein each X represents a halogen atom.

35. A compound according to claim 31, wherein each X represents a chlorine atom.

36. A compound according to claim 31, wherein $Z^{12}$ has the formula:

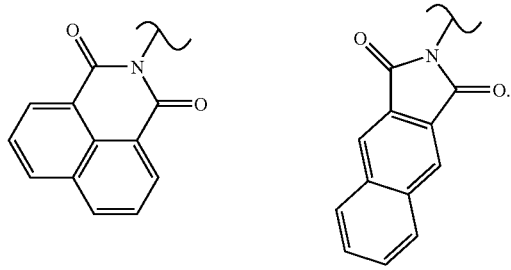

37. A method for catalyzing decomposition of a vinyldiazomethane or an aryldiazomethane, said method comprising contacting the vinyldiazomethane or aryldiazomethane with a compound according to claim 1.

38. A method for generating a rhodium carbene, said method comprising contacting a carbene precursor with a compound according to claim 1.

39. A method of producing a compound having the following formula (CI):

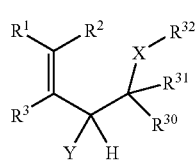

where $R^1$, $R^2$, and $R^3$ are independently selected from H, alkyl, aryl, or vinyl or where $R^1$ and $R^3$, together with the atoms to which they are bonded, form a 5-12 membered ring; Y is an electron withdrawing group; X is $CH_2$, O or $NR^{11}$; $R^{11}$ is H, an alkyl group, an aryl group, an acyl group, an alkoxycarbonyl group, or a silyl group having the formula $-SiR^{33}R^{34}R^{35}$; each of $R^{30}$ and $R^{31}$ is independently selected from the group consisting of H, alkyl, aryl, and vinyl; $R^{32}$ is an alkyl group, an aryl group, an acyl group, an alkoxycarbonyl group, or a silyl group having the formula $-SiR^{36}R^{37}R^{38}$; or $R^{31}$ and $R^{32}$, together with the atoms to which they are bonded, form a 5-12 membered ring; $R^{33}$, $R^{34}$, $R^{35}$, $R^{36}$, $R^{37}$, and $R^{38}$ are independently selected from an alkyl group and an aryl group; provided that when each of $R^{30}$ and $R^{31}$ is H, X is not $CH_2$, said method comprising:
providing a diazo compound having the formula:

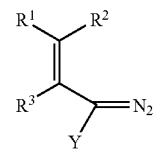

and
converting the diazo compound with a compound having the following formula (CII):

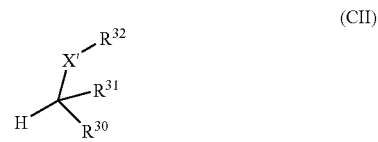

in the presence of a compound according to claim 1 under conditions effective to produce the compound of formula CI, wherein X' is $CH_2$, O or $NR^{11'}$ and $R^{11'}$ is an alkyl group, an aryl group, an acyl group, an alkoxycarbonyl group, or a silyl group.

40. A method of catalyzing an aryldiazomethane or a vinyldiazomethane insertion reaction, said method comprising:
providing a aryldiazomethane or a vinyldiazomethane;
providing a compound according to claim 1; and
contacting the aryldiazomethane or the vinyldiazomethane with the compound according to claim 1 under conditions effective to catalyze the aryldiazomethane or vinyldiazomethane insertion reaction.

41. A method of producing a compound having the following formula (CIV):

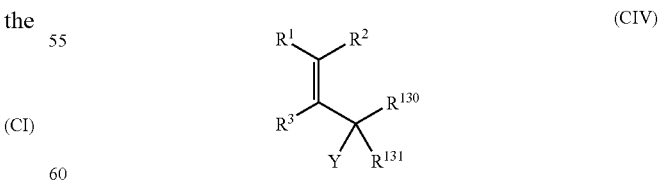

where $R^1$, $R^2$, and $R^3$ are independently selected from H, alkyl, aryl, or vinyl or where $R^1$ and $R^3$, together with the atoms to which they are bonded, form a 5-12 membered ring; where Y is an electron withdrawing group; where $R^{131}$ is H and $R^{130}$ is an alkyl group, an aryl group, an alkoxy group, an amine group, or a silyl group; or where $R^{130}$ and $R^{131}$, together with the atom to which they are bonded, form a substituted or unsubstituted cyclopropane moiety; said method comprising:

provinding a diazo compound having the formula:

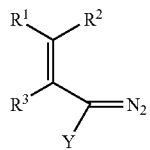

and converting the diazo compound to the compound of formula (CIV) in the presence of compound according to claim 1 and under conditions effective to produce the compound of formula (CIV).

42. A method of catalyzing an aryldiazomethane or a vinyldiazomethane cyclopropanation reaction, said method comprising:

providing a aryldiazomethane or a vinyldiazomethane;

providing a compound according to claim 1; and contacting the aryldiazomethane or the vinyldiazomethane with the compound according to claim 1 under conditions effective to catalyze the aryldiazomethane or vinyldiazomethane cyclopropanation reaction.

43. A method for generating a rhodium nitrene, said method comprising contacting a nitrene precursor with a compound according to claim 1.

44. A method of catalyzing a C—H amination reaction, said method comprising:

providing a compound comprising a C—H bond;

providing a compound according to claim 1; and contacting the compound comprising a C—H bond with the compound according to claim 1 under conditions effective to catalyze the C—H amination reaction.

\* \* \* \* \*